(12) United States Patent
Umek et al.

(10) Patent No.: US 7,935,481 B1
(45) Date of Patent: May 3, 2011

(54) SEQUENCE DETERMINATION OF NUCLEIC ACIDS USING ELECTRONIC DETECTION

(75) Inventors: Robert M. Umek, Silver Spring, MD (US); Gary Blackburn, Glendora, CA (US); Bruce D. Irvine, Glendora, CA (US); Robert H. Terbrueggen, Manhattan Beach, CA (US); Changjun Yu, Pasadena, CA (US); Jost G. Vielmetter, Altadena, CA (US)

(73) Assignee: Osmetech Technology Inc., Pasadena, CA (US)

( * ) Notice: Subject to any disclaimer, the term of this patent is extended or adjusted under 35 U.S.C. 154(b) by 1701 days.

(21) Appl. No.: 09/626,096

(22) Filed: Jul. 26, 2000

Related U.S. Application Data

(60) Provisional application No. 60/145,695, filed on Jul. 26, 1999, provisional application No. 60/190,259, filed on Mar. 17, 2000.

(51) Int. Cl.
*C12Q 1/68* (2006.01)
(52) U.S. Cl. ............................................ 435/6
(58) Field of Classification Search ............ 435/6, 91.1, 435/91.2; 439/24.3, 24.33; 536/231, 24.3
See application file for complete search history.

(56) References Cited

U.S. PATENT DOCUMENTS

| | | |
|---|---|---|
| 4,656,127 A | 4/1987 | Mundy |
| 4,683,195 A | 7/1987 | Mullis et al. |
| 4,683,202 A | 7/1987 | Mullis |
| 4,704,193 A | 11/1987 | Bowers et al. |
| 4,707,352 A | 11/1987 | Stavrianopoulos |
| 4,707,440 A | 11/1987 | Stavrianopoulos |
| 4,711,955 A | 12/1987 | Ward et al. |
| 4,713,347 A | 12/1987 | Mitchell et al. |
| 4,755,458 A | 7/1988 | Rabbani et al. |
| 4,787,963 A | 11/1988 | MacConnell |
| 4,840,893 A | 6/1989 | Hill et al. |
| 4,849,513 A | 7/1989 | Smith et al. |
| 4,851,331 A | 7/1989 | Vary et al. |
| 4,868,103 A | 9/1989 | Stavrianopoulos et al. |
| 4,876,187 A | 10/1989 | Duck et al. |
| 4,894,325 A | 1/1990 | Englehardt et al. |
| 4,943,523 A | 7/1990 | Stavrianopoulos |
| 4,945,045 A | 7/1990 | Forrest et al. |
| 4,952,685 A | 8/1990 | Stavrianopoulos |
| 4,988,617 A | 1/1991 | Landegren et al. |
| 4,994,373 A | 2/1991 | Stavrianopoulos |
| 5,002,885 A | 3/1991 | Stavrianopoulos |
| 5,011,769 A | 4/1991 | Duck et al. |
| 5,013,831 A | 5/1991 | Stavrianopoulos |
| 5,015,569 A | 5/1991 | Pontius |
| 5,082,830 A | 1/1992 | Brakel et al. |
| 5,089,112 A | 2/1992 | Skotheim et al. |
| 5,130,238 A | 7/1992 | Malek et al. |
| 5,156,810 A | 10/1992 | Ribi |
| 5,171,853 A | 12/1992 | Thorp et al. |
| 5,175,269 A | 12/1992 | Stavrianopoulos |
| 5,175,270 A | 12/1992 | Nilsen et al. |
| 5,180,968 A | 1/1993 | Bruckenstein et al. |
| 5,185,243 A * | 2/1993 | Ullman et al. ................. 435/6 |
| 5,200,051 A | 4/1993 | Cozzette et al. |
| 5,238,808 A | 8/1993 | Bard et al. |
| 5,241,060 A | 8/1993 | Engelhardt et al. |
| 5,242,828 A | 9/1993 | Bergstrom et al. |
| 5,244,560 A | 9/1993 | Kuhr |
| 5,278,043 A | 1/1994 | Bannwarth et al. |
| 5,308,754 A | 5/1994 | Kankare et al. |
| 5,312,527 A | 5/1994 | Mikkelsen et al. |
| 5,328,824 A | 7/1994 | Ward et al. |
| 5,391,272 A | 2/1995 | O'Daly et al. |
| 5,403,451 A | 4/1995 | Riviello et al. |
| 5,403,711 A | 4/1995 | Walder et al. |
| 5,409,818 A | 4/1995 | Davey et al. |
| 5,436,161 A | 7/1995 | Bergstrom et al. |
| 5,443,701 A | 8/1995 | Willner et al. |
| 5,449,767 A | 9/1995 | Ward et al. |
| 5,455,166 A | 10/1995 | Walker |
| 5,472,881 A | 12/1995 | Beebe et al. |
| 5,474,796 A | 12/1995 | Brennan |
| 5,476,928 A | 12/1995 | Ward et al. |
| 5,487,973 A | 1/1996 | Nilsen et al. |
| 5,492,806 A | 2/1996 | Drmanac et al. |
| 5,494,810 A | 2/1996 | Barany et al. |
| 5,525,464 A | 6/1996 | Drmanac et al. |
| 5,534,424 A | 7/1996 | Uhlen et al. |
| 5,545,531 A | 8/1996 | Rava et al. |

(Continued)

FOREIGN PATENT DOCUMENTS

| CA | 2 090 904 A1 | 9/1993 |
|---|---|---|

(Continued)

OTHER PUBLICATIONS

Baner, Johan et al. Signal amplification of padlock probes by rolling circle replication. 1998. Nucleic Acids Research 26:5073-5078.*

(Continued)

*Primary Examiner* — Heather Calamita
(74) *Attorney, Agent, or Firm* — Morgan, Lewis & Bockius LLP; Robin M. Silva; Tuan N. Nguyen

(57) ABSTRACT

The present invention is directed to methods and compositions for the use of self-assembled monolayers to electronically detect nucleic acids, particularly alterations such as nucleotide substitutions (mismatches) and single nucleotide polymorphisms (SNPs).

10 Claims, 24 Drawing Sheets

U.S. PATENT DOCUMENTS

| | | | |
|---|---|---|---|
| 5,547,839 A | 8/1996 | Dower et al. | |
| 5,552,270 A | 9/1996 | Khrapko et al. | |
| 5,565,322 A | 10/1996 | Heller | |
| 5,565,552 A | 10/1996 | Magda et al. | |
| 5,571,568 A | 11/1996 | Ribi et al. | |
| 5,573,906 A | 11/1996 | Bannwarth et al. | |
| 5,591,578 A | 1/1997 | Meade et al. | |
| 5,595,908 A | 1/1997 | Fawcett et al. | |
| 5,601,982 A | 2/1997 | Sargent et al. | |
| 5,605,662 A * | 2/1997 | Heller et al. | 422/68.1 |
| 5,616,464 A | 4/1997 | Albagli et al. | |
| 5,620,850 A | 4/1997 | Bamdad et al. | |
| 5,632,957 A | 5/1997 | Heller et al. | |
| 5,633,134 A * | 5/1997 | Shuber | 435/6 |
| 5,660,988 A | 8/1997 | Duck et al. | |
| 5,670,322 A | 9/1997 | Eggers et al. | |
| 5,695,940 A | 12/1997 | Drmanac et al. | |
| 5,700,667 A | 12/1997 | Marble et al. | |
| 5,705,346 A | 1/1998 | Okamoto et al. | |
| 5,705,348 A | 1/1998 | Meade et al. | |
| 5,710,028 A | 1/1998 | Eyal et al. | |
| 5,727,548 A | 3/1998 | Hill et al. | |
| 5,741,700 A | 4/1998 | Ershov et al. | |
| 5,747,255 A | 5/1998 | Brenner | |
| 5,756,050 A | 5/1998 | Ershow et al. | |
| 5,767,259 A | 6/1998 | Albagli et al. | |
| 5,770,369 A | 6/1998 | Meade et al. | |
| 5,770,721 A | 6/1998 | Ershov et al. | |
| 5,776,672 A | 7/1998 | Hashimoto et al. | |
| 5,780,224 A | 7/1998 | Collins et al. | |
| 5,780,234 A | 7/1998 | Meade et al. | |
| 5,795,453 A | 8/1998 | Gilmartin | |
| 5,824,473 A | 10/1998 | Meade et al. | |
| 5,837,832 A | 11/1998 | Chee et al. | |
| 5,837,859 A | 11/1998 | Teoule et al. | |
| 5,846,708 A | 12/1998 | Hollis et al. | |
| 5,846,717 A | 12/1998 | Brow et al. | |
| 5,849,486 A | 12/1998 | Heller et al. | |
| 5,851,772 A | 12/1998 | Mirzabekov et al. | |
| 5,854,033 A | 12/1998 | Lizasrdi | |
| 5,861,242 A | 1/1999 | Chee et al. | |
| 5,871,918 A | 2/1999 | Thorp et al. | |
| 5,874,046 A | 2/1999 | Megerle | |
| 5,888,819 A | 3/1999 | Goelet et al. | |
| 5,891,630 A | 4/1999 | Eggers et al. | |
| 5,922,617 A | 7/1999 | Wang et al. | |
| 5,925,520 A | 7/1999 | Tully et al. | |
| 5,942,388 A | 8/1999 | Willner et al. | |
| 5,942,397 A | 8/1999 | Tarlov et al. | |
| 5,945,286 A | 8/1999 | Krihak et al. | |
| 5,952,172 A | 9/1999 | Meade et al. | |
| 5,968,745 A | 10/1999 | Thorp et al. | |
| 5,972,692 A | 10/1999 | Hashimoto et al. | |
| 5,976,802 A | 11/1999 | Ansorge et al. | |
| 6,060,023 A | 5/2000 | Maracas | |
| 6,060,327 A | 5/2000 | Keen | |
| 6,066,448 A | 5/2000 | Wohlstadter et al. | |
| 6,071,699 A | 6/2000 | Meade et al. | |
| 6,087,100 A | 7/2000 | Meade et al. | |
| 6,090,545 A | 7/2000 | Wohlstadter et al. | |
| 6,096,273 A * | 8/2000 | Kayyem et al. | 422/68.1 |
| 6,096,825 A | 8/2000 | Garnier et al. | |
| 6,107,080 A | 8/2000 | Lennox | |
| 6,177,250 B1 * | 1/2001 | Meade et al. | 435/6 |
| 6,180,352 B1 | 1/2001 | Meade et al. | |
| 6,200,761 B1 | 3/2001 | Meade et al. | |
| 6,203,758 B1 | 3/2001 | Marks et al. | |
| 6,207,369 B1 | 3/2001 | Wohlstadter et al. | |
| 6,238,870 B1 | 5/2001 | Meade et al. | |
| 6,361,671 B1 | 3/2002 | Mathies et al. | |
| 6,541,617 B1 * | 4/2003 | Bamdad et al. | 536/23.1 |
| 6,686,150 B1 * | 2/2004 | Blackburn et al. | 435/6 |

FOREIGN PATENT DOCUMENTS

| | | |
|---|---|---|
| EP | 0 063 879 A2 | 11/1982 |
| EP | 0 142 301 A2 | 5/1985 |
| EP | 0 234 938 A2 | 2/1987 |
| EP | 0 229 943 B1 | 7/1987 |
| EP | 0 317 074 B1 | 5/1989 |
| EP | 0 371 437 B1 | 6/1990 |
| EP | 0 478 319 A1 | 4/1992 |
| EP | 0 599 337 A2 | 1/1994 |
| EP | 0 668 502 A2 | 8/1995 |
| EP | 0 515 615 | 9/1996 |
| JP | 238166 A | 10/1988 |
| JP | 6-41183 A2 | 2/1994 |
| WO | WO 86/05815 A1 | 10/1986 |
| WO | WO 90/05732 A1 | 5/1990 |
| WO | WO 92/10757 A1 | 6/1992 |
| WO | WO 92/15712 A1 | 9/1992 |
| WO | WO 93/10267 A1 | 5/1993 |
| WO | WO 93/22678 A2 | 11/1993 |
| WO | WO 93/25898 A1 | 12/1993 |
| WO | WO 94/22889 A1 | 10/1994 |
| WO | WO 95/00666 A1 | 1/1995 |
| WO | WO 95/00667 A1 | 1/1995 |
| WO | WO 95/00669 A1 | 1/1995 |
| WO | WO 95/05480 A2 | 2/1995 |
| WO | WO 95/05480 A3 | 2/1995 |
| WO | WO 95/15971 A2 | 6/1995 |
| WO | WO 95/34816 A1 | 12/1995 |
| WO | WO 96/06946 A1 | 3/1996 |
| WO | WO 96/40712 A1 | 12/1996 |
| WO | WO 97/01646 A2 | 1/1997 |
| WO | WO 97/27329 A1 | 7/1997 |
| WO | WO 97/27473 A1 | 7/1997 |
| WO | WO 97/31256 A3 | 8/1997 |
| WO | WO 97/13075 A1 | 9/1997 |
| WO | WO 97/41425 A1 | 11/1997 |
| WO | WO 97/444651 A1 | 11/1997 |
| WO | WO 98/04740 A1 | 2/1998 |
| WO | WO 98/12539 A1 | 3/1998 |
| WO | WO 98/20162 * | 5/1998 |
| WO | WO 98/20162 A2 | 5/1998 |
| WO | WO 98/27229 A2 | 6/1998 |
| WO | WO 98/28444 A2 | 7/1998 |
| WO | WO 98/31839 A2 | 7/1998 |
| WO | WO 98/35232 A2 | 8/1998 |
| WO | WO 98/49344 A1 | 11/1998 |
| WO | WO 98/51823 A1 | 11/1998 |
| WO | WO 98/57159 A1 | 12/1998 |
| WO | WO 99/13109 A1 | 3/1999 |
| WO | WO 99/14596 A1 | 3/1999 |
| WO | WO 99/15893 A1 | 4/1999 |
| WO | WO 99/29711 A1 | 6/1999 |
| WO | WO 99/37819 A2 | 7/1999 |
| WO | WO 98/57319 A1 | 11/1999 |
| WO | WO 99/67425 A2 | 12/1999 |

OTHER PUBLICATIONS

Bamdad, C. "A DNA self-assembled monolayer for the specific attachment of unmodified double—or single stranded DNA," Biophysical Journal, 75:1997-2003 (1988).

Hess et al., "Base Pairing Properties of Novel Transition Metal PNA Conjugates," Journal of Inorganic Biochemistry, 74:161 (1999).

Beattie et al., "Genosensor Technology," Clinical Chemistry, 39(4): 719-722 (1993).

Griffin et al., "Single-nucleotide polymorphism analysis by MALDI-TOF mass spectrometry," Trends in Biotechnology, 14(10): 77-84 (2000).

Gilles et al., "Single nucleotide polymorphic discrimination by an electronic dot blot assay on semiconductor microchips," Nature Biotechnology, 17:365-370 (1999).

O'Donnell-Maloney et al., "The development of microfabricated arrays for DNA sequencing and analysis," Trends in Biotechnology, 14(10): 401-407 (1996).

Yu et al., "Uridine-conjugated-ferrocene DNA oligonucleotides for electronic detection of nucleic acids," Abstracts of Papers. ACS National Meeting, 217(1): 76 (1999).

Alexander, V., "Design and Synthesis of Macrocyclic Ligands and Their Complexes of Lanthanides and Actinides," *Chem. Rev.* 95(2):273-342 (Mar.-Apr. 1995).

Alsfasser, R., et al., "Novel Building Blocks for Biomimetic Assemblies. Synthesis, Characterization, and Spectroscopic and Electrochemical Properties of New Bidendate Ligands Derived from Lysine and Cystine and Their Complexes with Bis(2,2'-bipyridine)ruthenium(II)," *Inorg. Chem.* 35(3):628-636 (Jan. 1996).

Arkin, M., et at, "Rates of DNA-Mediated Electron Transfer Between Metallointercalators," *Science* 273(5274):475-480 (Jul. 1996).

Bains, W., et al., "A Novel Method for Nucleic Acid Sequence Determination," *J. Theor. Biol.* 135(3):303-307 (Dec. 1988).

Barany, F., "Genetic disease detection and DNA amplification using cloned thermostable ligase," *Proc. Natl. Acad. Sci. USA* 88(1):189-193 (Jan. 1991).

Beattie, K., et al., "Advances in Genosensor Research," *Clin. Chem.* 41(5):700-706 (1995).

Bignozzi, C., et al., "A simple poly(pyridine)ruthenium(II) photosensitizer: (2,2'- bipyridine)tetracyanoruthenate(II)," *J. Am. Chem. Soc.* 108(24):7872-7873 (Nov. 1986).

Bjerrum, M., et al., "Electron transfer in ruthenium-modified proteins," *J. Bioenerg. Biomembr.* 27(3):295-302 (Jun. 1995).

Blonder, R., et al., "Application of redox enzymes for probing the antigen-antibody association at the monolayer interfaces: development of amperometric immunosensor electrodes," *Anal. Chem.* 68(18):3151-3157 (Sep. 1996).

Carlsson, C., et al., "Screening for genetic mutations," *Nature* 380(6571):207 (Mar. 1996).

Carter, M., et al., "Electrochemical investigations of the interaction of metal chelates with DNA. 3. Electrogenerated chemiluminescent investigation of the interaction of tris(1,10-phenathroline)ruthenium(II) with DNA," *Bloconjug. Chem.* 1(4):257-263 (Jul.-Aug. 1990).

Carter, P., et al., "Oxidation of DNA Haripins by Oxoruthenium(IV): Effects of Sterics and Secondary Structure," *Inorg. Chem.* 35(11):3348-3354 (May 1996).

Caruana, D. J., et al., "Enzyme-amplified amperometric detection of hybridization and of a single base pair mutation in an 18-base oligonucleotide on a 7-µm-diameter microelectrode," *J. Am. Chem. Soc.* 121(4):769-774 (Feb. 1999).

Chailapakul, O., et al., "Interactions between organized, surface-confined monolayers and liquid-phase probe molecules. 4. synthesis and characterization of nanoporous molecular assemblies: mechanism of probe penetration," *Langmuir* 11(4):1329-1340 (Apr. 1995).

Cheng, J., et al., "Selectivity and sensitivity of self-assembled thioctic acid electrodes," *Anal. Chem.* 64(17)1998-1999 (Sep. 1992).

Chiem, N., et al., "Microfluidic Systems for Clinical Diagnostics," *Transducers'97, Intl. Conf. Solid-State Sens. Actuators*, Chicago, IL (Jun. 16-19, 1997).

Clarke, P.R., et al., "Physical and chemical aspects of ultrasonic disruption of cells," *J. Acoustics Soc. Am.* 50 649-653 (1970).

Daizadeh, I., et al., "Effect of protein dynamics on biological electron transfer," *Proc. Natl. Acad. Sci. USA* 94(8):3703-3708 (Apr. 1997).

Daubendiek, S., et al., "Generation of catalytic RNAs by rolling trascription of synthetic DNA nanocircles," *Nat. Biotechnol.* 15(3):273-277 (Mar. 1997).

Delamarche, E, et al., "Immobilization of antibodies on a photoactive self-assembled monolayer on gold," *Langmuir* 12(8):1997-2006 (Apr. 1996).

Doktycz, M., et al., "Genosensors and Model Hybridization Studies," *Automation Technologies for Genome Characterization*, T. Beugelskijk (ed.), John Wiley & Sons: New York, NY, 1997, 10:205-225.

Dong, S., "Self-assembled monolayers of thiols on gold electrodes for bioelectrochemistry and biosensors," *Bioelectrochem. Bioenerg.* 42(1):7-13 (1997).

Dontha, N., et al., "Generation of biotin/avidin/enzyme nanostructures with maskless photolithography," *Anal. Chem.* 69(14):2619-2625 (Jul. 1997).

Doron, A., et al., "An Electroactive photoisomerizable monolayer-electrode: a command surface for the amperometric transduction of recorded optical signals," *Angew. Chem. Int. Ed. Engl.* 35(13 &14):1535-1538 (Jul. 1996).

Drmanac, R., el al., "Sequencing of Megabase Plus DNA Hybridization: Theory of the Method," *Genomics* 4(2):114-128 (Feb. 1989).

Duan, C., et al., "Separation-free sandwich enzyme immunoassays using microporous gold electrodes and self-assembled monolayer/immobilized capture antibodies," *Anal. Chem.* 66(9):1369-1377 (May 1994).

Ducey, M., et al., "Competitive nonseparation electrochemical enzyme binding/immunoassay (NEEIA) for small molecule detection," *Anal. Chim. Acta* 357(1&2):5-12 (Dec. 1997).

Eggers, M., et al., "Genosensors: Microfabricated Devices for Automated DNA Sequence Analysis," *Adv. DNA Sequencing Tech.* 1891:113-126 (1993).

Egholm, M., et al, "Peptide nucleic acids (PNA) Oligonucleotide Analogues with an Achiral Peptide Backbone," *J. Am. Chem. Soc.* 114(5):1895-1897 (Feb. 1992).

Elliott, C.M., et al., "Electrochemistry, spectroelectrochemistry, and photochemistry of a series of new covalently linked tris(2,2'-bipyridine)ruthenium(II)/diquat complexes," *J. Am. Chem. Soc.* 107(16):4647-4655 (Aug. 1985).

Evensen, H., et al., "Automated fluid mixing in glass cappillaries," *Rev. Scient. Instrum.* 69(2):519-526 (Feb. 1998).

Ewing, A., et al., "Electrochemical detection in microcolumn separations," *Anal. Chem.* 66(9):527A-537A (May 1994).

Fojta, M., et al., "Supercoiled DNA-modified mercury electrode: A highly sensitive tool for the detection of DNA damage," *Anal. Chim. Acta* 342(1):1-12 (Apr. 1997).

Fossum, E., "Novel Sensor Enables Low-Power, Miniaturized Imagers," *Photonics Spectra* 125-126 (Jan. 1996).

Fukui, K., et al., "Distance dependence of photoinduced electron transfer in DNA," *Angew. Chem. Int. Ed. Engl.* 37(1&2):158-161 (Feb. 1998).

Ghindilis, A., et al., "Immunosensors: electrochemical sensing and other engineering approaches," *Biosens. Bioelect.* 13(1):113-131 (Jan. 1998).

Gongora-Rubio, M.R., et al., "Overview of low temperature co-fired ceeramics tape technology for meso-system technology MsST)," *Sens. Actuators A* 89(3):222-241 (Apr. 2001).

Goodwin, D., et al., "Microwave Miniprep of Total Genomic DNA from Fungi, Plants, Protists and Animals for PCR," *BioTechniques* 15(3):437-441 (1993).

Gozel, P., et al., 'Electrokinetic resolution of amino acid enantiomers with copper(II)-aspartame support electrolyte; *Anal. Chem.* 59(1):44-49 (Jan. 1987).

Hall, D., et al., "Sensitivity of DNA-Mediated Electron Transfer to the invervening π-Stack: A Probe for the Intergrity of the DNA Base Stack," *J. Am. Chem. Soc.* 119(21):5045-5046 (May 1997).

Harrison, D., et al., "Characterization of perfluorosulfonic acid polymer coated enzyme electrodes and a miniaturized integrated potentiostat for glucose analysis in whole blood," *Anal. Chem.* 60(19):2002-2007 (Oct. 1988).

Harrison, D., et al., "Immunoassay Flow Systems )n-Chip," *Solid-State Sensor and Actuator Workshop*, Hilton Head. SC, pp. 5-8 (1996).

Hashimoto, K., et al., "DNA sensor: A novel electrochemical gene detection method using carbon electrode Immobilized DNA probes," *Supramol. Chem.* 2:265-270 (1993).

Herne, T.M., et al., "Characterization of DNA Probes Immobilized on Gold Surfaces," *J. Am. Chem. Soc.* 119(38):8918-8920 (Sep. 1987).

Hoffmann, A, et al., "Purification of his-tagged proteins in non-denaturing conditions suggests a convenient method for protein interaction studies," *Nucleic Acids Res.* 19(22):6337-6338 (Nov. 1991).

Hwang, J-T., et al., "Synthesis of 2'-Modified Oligodeoxynucleotides via On-column Conjugation," *J. Org. Chem.* 66(2):363-369 (Jan. 2002).

Hwang, J-T., et al., "Synthesis of Modified Oligodeoxyribonucleotides on a Solid Phase Support via Derivatization of a Selectively Revealed 2'-Amino-2-deoxyuridine," *Org. Lett.* 1(12):2021-2024 (Dec. 1999).

Ihara, T., et al., "Gene sensor using ferrocenyl oligonucleotide." *Chem. Commun.* 17:1609-1610 (1997).

Jiang, L., et al., "Direct electron transfer reactions of glucose oxidase immobilised at a self-assembled monolayer," *J. Chem. Soc. Chem. Commun.* 12:1293-1295 (1995).

Jonsson, U., et al., "Biosensors based on surface concentration measuring devices—The concept of surface concentration," *Prog. Colloid Polym. Sci.* 70:96-100 (1985).

Katz, E., et al., "Application of stilbene-(4,4'-diisothiocyanate)-2,2'-disulfonic acid as a bifunctional reagent for the organization of organic materials and proteins onto electrode surfaces," *J. Electroanal. Chem.* 354(1&2):129-144 (1993).

Katz, E., et al., "Electrical contact of redox enzymes with electrodes: novel approaches for amperometric biosensors," *Bioelectrochem. Bioenerg.* 42(1):95-104 (1997).

Katz, E., et al., "Electron Transfer in Self-Assembled Monolayers of N-Methyl-N'-carboxyalkyl-4-4'-bipyridinium Linked to Gold Electrodes," *Langmuir* 9(5):1392-1396 (May 1993).

Kelley, S.O., et al., "Photoinduced Electron Transfer in Ethidium-Modified DNA Duplexes: Dependence on Distance and Base Stacking," *J. Am. Chem. Soc.* 119(41):9861-9870 (Oct. 1997).

Kirschenheuter, G., et al., "An Improved Synthesis of 2'-Azido-2'-Deoxyuridine," *Tetrahedron Lett.* 35(46):8517-8520 (Nov. 1994).

Kohne, D., et al., "Room temperature method for increasing the rate of dna reassociation by many thousandfold: the phenol emulsion reassociation technique," *Biochemistry* 16(24):5329-5341 (Nov. 1977).

Kretschmann, E., et al., "Radioactive Decay of Non Radiative Surface Plasmons Excited by Light," *Z. Naturforsch.* 23A:2135-2136 (1968).

Kunitake, M., et al., "Transmembrane rectified electron transfer through π-conjugated electroactive langmuir-blodgett monolayers on gold electrodes," *Bull. Chem. Soc. Jpn.* 67(2):373-378 (1994).

Lee, S.-W., et al., "A micro cell lysis device," *Sens. Actuators A* 73(1&2):74-79 (Mar. 1999).

Li, J., et al., "Direct electron transfer to cytochrome c oxidase in self-assembled monolayers on gold electrodes", *J. Electroanal. Chem.* 416(1&2):97-104 (Nov. 1996).

Li, J., et al., "Viologen-thiol self-assembled monolayers for immobilized horseradish peroxidase at gold electrode surface," *Electrochim. Acta* 42(6):961-967 (1997).

Lion-Dagan, M., et al., "A Bifunctional Monolayer Electrode consisting of 4-Pyridyl Sulfide and Photosiomerizable Spiropyran: Photoswitchable Electrical Communication between the Electrode and Cytochrome C," *J. Chem. Soc. Chem. Commun.* 24:2741-2742 (1994).

Liu, R., et al., "Passive mixing in a three dimensional serpentine microchannel," *J. Microelectromech. Syst.* 9(2)190-196 (Jun. 2000).

Livache, T., et al., "Biosensing effects in functionafized electroconducting conjugated polymer layers: addressable DNA matrix for the detection of gene mutations," *Synth. Metals* 71:2143-2146 (1995).

Lowe, C.R., "An Introduction to the Concepts and Technology of Biosensors," *Biosensors I*, pp. 3-16 (1985).

Lysov, Y., et al., "A new method for determining the DNA nucleotide sequence by hybridization with oligonucleotides." *Doklady Biochem. Proc. Acad. Sci. USSR* 303(6):436-438 (May 1989).

Mandler, D., et al., "Applications of self-assembled monolayers in electroanalytical chemistry," *Electroanalysis* 8(3):207-213 (1996).

McGee, D., et al., "Novel nucleosides via intramolecular functionalization of 2,2'-anhydrouridine derivatives," *Tetrahedron Lett.* 37(12):1995-1998 (1996).

Michalitsch, R., et al., "Properties of self-assembled monolayers (SAMS) from thiol-functionalized oliothiophenes," *Adv. Mater.* 9(4):321-325 (Apr. 1997).

Mikkelsen, S., "Electrochemical Biosensors for DNA Sequence Detection," *Electroanalysis* 8(1):15-19 (1996).

Mir, K., et al., "Determining the influence of structure on hybridization using oligonucleotide arrays," *Nat. Biotechnol.* 17(8):788-792 (Aug. 1999).

Mirkhalaf, F., et al., "Surface spectroscopy and electrochemical characterisation of metal dithizonates covalently attached to gold by a self-assembled cysteamine monolayer," *J. Chem. Soc. Faraday Transact.* 94(9):1321-1327 (1998).

Mirsky, V., et al., "Capacitive monitoring of protein immobilization and antigen-antibody reactions on monomolecular alkylthiol films on gold electrode," *Biosens. Bioelect.* 12(9&10):977-989 (1997).

Mistler, R.E., "Tape Casting: The Basic Process for Meeting the Needs of the Electronics Industry," *Ceramic Bull.* 69(6):1022-1026 (1990).

Muller, W., "Partitioning of Nucleic Acids", Partitioning in Aqueous Two-Phase Systems, *Partitioning in Aqueous Two-Phase Systems*, Academic Press, Inc. San Diego, CA, 1995, 7:227-266.

Muller, W., et al., "DNA fractionation by two-phase partition with aid of a base specific macroligand," *Anal. Biochem.* 118(2):269-277 (Dec. 1981).

Napier, M., et al., "Modification of Electrodes with Dicarboxylate Self-Assembled Monolayers for Attachment and Detection of Nucleic Acids," *Langmuir* 13(23):6342-6344 (Nov. 1997).

Northrup, M., et al., "A Miniature analytical instrument for nucleic acids based on micromachined silicon reaction chambers," *Anal. Chem.* 70(1):918-922 (Mar. 1998).

Nyborg, W.L, "Acoustic Straining Near a Boundary," *J. Acoustics Soc. Am.* 30:329-339 (1958).

Obeng, Y., et al., "Electrogenerated Chemiluminescence. 53. Electrochemistry and Emission from Adsorbed Monolayers of a Tris(bipyridyl) ruthenium (II)- Based Surfactant on Fold and Tin Oxide Electrodes," *Langmuir* 7(1):195-201 (Jan. 1991).

Pang, D.-W., et al., "Modification of glassy carbon and gold electrodes with DNA," *J. Electroanal. Chem.* 403(1&2):183-188 (Feb. 1996).

Parikh, ., et al., "An Intrinsic relationship between molecular structure in self-assembled *n*-alkylsiloxane monolayers and deposition temperature," *J. Phys. Chem.* 98(31):7577-7590 (Aug. 1994).

Plaxco. K., et al., "The importance of being unfolded," *Nature* 386(6626):657-659 (Apr. 1997).

Potyrailo, R., et al., "Adapting selected nucleic acid ligans (aptamers) to biosensors," *Anal. Chem.* 70(16):3419-3425 (Aug. 1998).

Prezyna, L., et al., "Interation of catatonic polypeptides with electractive polypyrrole/poly(styrenesulfonate) and poly(n-methylpyrrole)/poly(styrenesulfonate) films," *Synth. Metals* 41(3):979-981 (May 1991).

Rojas, M., et al., "Molecular Recognition at the Electrode-Solution Interface, Design, Self-Assembly, and Interfacial Binding Properties of a Molecular Sensor," *J. Am. Chem. Soc.* 117(21):5883-5884 (May 1995).

Röchel, R.R., "Transmission-electron microscopic observations of freeze-etched polyacrylamide gels." *J. Chromatogr. A* 166(2):563-575 (Dec. 1978).

Sachs, S., et al., "Rates of interfacial electron transfer through conjugated spacers," *J. Am. Chem. Soc.* 119(43):10563-10564 (Oct. 1997).

Sakamoto, S., et al., "Design and synthesis of flavin conjugated peptines and assembly on a gold electrode," *J. Chem. Soc. Perkin Transact.* 2 2(11):2319-2326 (1996).

Smalley, J., et al., "Kinetics of Electron Transfer through Ferrocene-Terminated Alanethiol Monolayers Gold," *J. Phys. Chem.* 99(35):13141-13149 (Aug. 1995).

Smith, E., et al., "Corticotropin releasing factor induction of leukocyte-derived immunoreactive ACTH and endorphins," *Nature* 321(6073):881-882 (Jun. 1986).

Smith, L., et al., "Mapping and Sequencing the Human Genome: How to Proceed," *Biotechnology* 5:933-942 (1987).

Souteyrand, E., et al., "Direct detection of the hybridization of synthetic homo-oligomer DNA sequences by field effect," *J. Phys. Chem. B.* 101(15):2980-2985 (Apr. 1997).

Steinberg, S., et al., "Ion-Selective Monolayer Membranes Based upon Self-Assembling Tetradentate Ligand Monolayers on Gold Electrodes. 2. Effect of Applied Potential on Ion Binding," *J. Am. Chem. Soc.* 113(14):5176-5182 (Jul. 1991).

Steinberg, S., et al., "Ion-Selective Monolayer Membranes Based upon Self-Assembling Tetradentate Ligand Monolayers on Gold Electrodes. 3. Application as Selective Ion Sensors," *Langmuir* 8(4):1183-1187 (Apr. 1992).

Stelzle, M., et al., "On the Application of Supported Bilayers as Receptice Layers for Biosensors with Electrical Detection," *J. Phys. Chem.* 97(12):2974-2981 (Mar. 1993).

Stora, T., et al., "Metal ion trace detection by chelatro-modified gold electrode: a comparison of surface to bulk affinity," *Langmuir* 13(20):5211-5214 (Oct. 1997).

Sun, S., et al., "Preparation of active Langmuir-Blodgett films of glucose oxidase," *Langmuir* 7(4):727-737 (Apr. 1991).

Syvänen, A. C., "Detection of point mutations in human genes by the solid-phase miniseqencing method," *Clin. Chim. Acta* 226(2):225-236 (May 1994).

Takeda, H., et al., "Preparation of 1-alkynyl 2-(trimethylsityl)ethyl sulfides as thiolare anion precursors for self-assembled monolayers," *Tetrahedron Lett.* 39(22):3701-3704 (May 1998).

Terrettaz, S., et al., "Protein binding to supported lipid membranes: investigation of the cholera toxin-ganglioside interaction by simultaneous impedance spectroscopy and surface plasmon resonance," *Langmuir* 9(5):1361-1369 (May 1993).

Tominaga, M., et al., "Tuning of lipid bilayer fluidity regulates mediated electron transfer reactions of glucase oxidase immoblized on lipid bilayer films on an electrode," *Bioelectrochem. Bioenerg.* 42(1):59-62 (Apr. 1997).

Topfer, M. L., *Technology Thick-Film Microelectronics: Fabrication, Design, and Applications:Microelectronics Series*; Litton Educational Publishing, Inc.: New York, NY, 3:41-59 (1971).

Tsuneo, M., et al., "Coumarin-fluorescein pair as a new donor-acceptor set for fluorescence energy transfer study of DNA," *Tetrahedron Lett.* 41(15):2605-2608 (2000).

Walker, G.T., et al., "A Chemiluminescent DNA Probe Test Based on Strand Displacement Amplification," *Molecular Methods for Virus Dectection*, ch. 15, pp. 329-349, Academic Press, Inc.; San Diego, CA (1995).

Wallace et al., "Electron Transfer of Yeast Cytochrome C Immobilized On Sam Modified Gold Electrodes", *Book of Abstracts*, 214th ACS National Meeting, Las Vegas, NV, PHYS-326, American Chemical Society, Washington D. C. (Sep. 7-11, 1997).

Wang, J., et al., "DNA biosensor for the detection of hydrazines," *Anal. Chem.* 68(13):2251-2254 (Jul. 1996).

Wang, J., et al. "Trace measurements of nucleic acids using flow injection amperometry," *Anal. Chim. Acta* 319(3):347-352 (Feb. 1996).

Welch, T., et al., "Distribution of Metal Complexes Bound to DNA Determined by Normal Pulse Voltammetry," *J. Phys. Chem.* 100(32):13829-13836 (Aug. 1996).

Welch, T., et al., "Electron-Rich Oxoruthenium(IV) Cleavage Agents: A Zero-Order Rate Law for DNA Catalysis," *Inorg. Chem.* 36(21):4812-4821 (Oct. 1997).

Wilding P., et al., "PCR in a Silicon Microstructure," *Clin. Chem.* 40(9):1815-1818 (Sep. 1994).

Wood, J.C., et al., "Time-Frequency Transforms: A New Approach to First Heart Sound Frequency Dynamics," *IEEE Taansact. Biomed. Eng.* 39(7):730-740 (1992).

Yguerabide, J., et al., "Quantitative Flourescence Method for Continuous Measurement of DNA Hybridization Kinetics Using a Fluorescent Intercalator," *Anal. Biochem.* 228(2):208-220 (Jul. 1995).

Aizawa et al., "Integrated Molecular Systems for Biosensors," Sensors and Acuators B, B$\alpha$$ (Nos. 1/3) Part 1:1-5 (Mar. 1995).

Albers et al., "Design of Novel Molecular Wires for Realizing Long-Distance Electron Transfer," Biochemistry and Bioenergetics, 42:25-33 (1997).

Alleman, K. S., et al., "Electrochemical Rectification at a Monolayer-Modified Electrode," *J. Phys. Chem.*, 100:17050-17058 (1996).

Arkin et al., "Evidence for Photoelectron Transfer Through DNA Intercalation," *J. Inorganic Biochem. Abstracts*, 6th International Conference on Bioinorganic Chemistry, 51(1) & (2):526 (1993).

Barisci et al., "Conducting Polymer Sensors," *TRIP*, 4(9):307-311 (1996).

Baum, R. M., "Views on Biological, Long-Range Electron Transfer Stir Debate," *C&EN*, pp. 20-23 (1993).

Bechtold, R., et al., "Ruthenium-Modified Horse Heart Cytochrome *c*: Effect of pH and Ligation on the Rate of Intramolecular Electron Transfer between Ruthenium(II) and Heme(III)," *J. Phys. Chem.*, 90(16):3800-3804 (1986).

Bidan, "Electroconducting conjugated polymers: new sensitive matrices to build up chemical or electrochemical sensors. A Review.," *Sensors and Actuators*, B6:45-56 (1992).

Biotechnology and Genetics: Genetic Screening Integrated Circuit, *The Economist* (Feb. 25-Mar. 3, 1995).

Blonder et al., "Three-dimensional Redox-Active layered Composites of Au-Au, Ag-Ag and Au-Ag Collids," Chem. Commun. 1393-1394 (1998).

Boguslavsky, L. et al., "Applications of redox polymers in biosensors," *Solid State Ionics*, 60:189-197 (1993).

Bowler, B. E., et al., "Long-Range Electron Transfer in Donor (Spacer) Acceptor Molecules and Proteins," *Progress in Inorganic Chemistry: Bioinorganic Chemistry*, 38:259-322 (1990).

Brun, A. M., et al., "Photochemistry of Intercalated Quaternary Diazaaromatic Salts," *J. Am. Chem. Soc.*, 113:8153-8159 (1991).

Bumm, et al., "Are Single Molecular Wires Conducting?," *Science* 271:1705-1707 (1996).

Cantor, C.R. et al., "Report on the Sequencing by Hybridization Workshop," *Genomics*, 13:1378-1383 (1992).

Carr et al., "Novel Electrochemical Sensors for Neutral Molecules," *Chem. Commun.*, 1649-1650 (1997).

Carter et al., "Voltammetric Studies of the Interaction of Metal Chelates with DNA. 2. Tris-Chelated Complexes of Cobalt(III) and Iron(II) with 10-Phenanthroline and 2,2'-Bipridine," *J. Am. Chem. Soc.*, 11:8901-8911 (1989).

Chang, I-Jy, et al., "High-Driving-Force Electron Transfer in Metalloproteins: Intramolecular Oxidation of Ferrocytochrome *c* by $Ru(2,2'-bpy)_2(im)(His-33)^{3+}$," *J. Am. Chem. Soc.*, 113:7056-7057 (1991).

Chidsey, et al., "Coadsorption of Ferrocene-Terminated and Unsubstituted Alkanethiols on Gold Electroactive Self-Assembled Monolayers," *J. Am. Chem. Soc.*, 112:4301-4306 (1990).

Chidsey, C.E.D., et al., "Free Energy and Temperature Dependence of Electron Transfer at the Metal Electrolyte Interface," *Science*, 251:919-922 (1991).

Chrisey, et al., "Covalent attachment of synthetic DNA to self-assembled monolayer films," *Nucleic Acids Research*, 24(15):3031-3039 (1996).

Clery, "DNA Goes Electric," *Science*, 267:1270 (1995).

*Commerce Business Daily Issue* of Sep. 26, 1996 PSA#1688.

Davis, L. M., et al., Electron Donor Properties of the Antitumour Drug Amsacrine as Studied by Fluorescence Quenching of DNA-Bound, 1987.

Davis, L. M., et al., "Elements of biosensor construction," *Enzyme Microb. Technol.* 17:1030-1035 (1995).

Degani et al., "Direct Electrical Communication between Chemically Modified Enzymes and Metal Electrodes. 2. Methods for Bonding Electron-Transfer Relays to Glucose Oxidase and D-Amino-Acid Oxidase," *J. Am. Chem. Soc.* 110:2615-2620 (1988).

Degani, Y., et al., "Electrical Communication between Redox Centers of Glucose Oxidase and Electrodes via Electrostatically and Covalently Bound Redox Polymers," *J. Am. Chem. Soc.*, 111:2357-2358 (1989).

Degani, Y., et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.*, 91(6):1285-1288 (1987).

Deinhammer, R.S., et al., "Electronchemical Oxidation of Amine-containing compounds: A Route to the Surface Modification of glassy carbon electrodes," *Langmuir*, 10:1306-1313 (1994).

Dreyer, G. B., et al., "Sequence-specific cleavage of single-stranded DNA: Oligodeoxynucleotide-EDTA •Fe(II)," *Proc. Natl. Acad. Sci. USA*, 82:968-972 (1985).

Drobyshev, A. et al., "Sequence Analysis by Hybridization with Oligonucleotide Microchip: Identification of β-thalassemia Mutations," Gene, 188:45-52 (1997).

Dubiley, S. et al., "Fractionation, phosphorylation and Ligation on Oligonucleotide Microchips to Enhance Sequencing by Hybridization," Nucleic Acids Research, 25(12):2259-2265 (1997).

Durham, B., et al., "Electron-Transfer Kinetics of Singly Labeled Ruthenium(II) Polypyridine Cytochrome c Derivatives," *Advances in Chemistry Series*, 226:181-193 (1990).

Durham, B., et al., "Photoinduced Electron-Transfer Kinetics of Singly Labeled Ruthenium Bis(bipyridin) Dicarboxybipyridine Cytochrome c Derivatives," *Biochemistry*, 28:8659-8665 (1989).

Elghanian et al., "Selective Colorimetric Detection of Polynucleotides Based on the Distance-Dependent Optical Properties of Gold Nanoparticles," Science, 277:1078-1081 (1997).

Elias, H., et al., "Electron-Transfer Kinetics of Zn-Substituted Cytochrome c and Its Ru(NH$_3$)$_5$(Histidine-33) Derivative," J. Am. Chem. Soc., 110:429-434 (1988).

Farver, O., et al., "Long-range intramolecular electron transfer in azurins," Proc. Natl. Acad. Sci. USA, 86:6968-6972 (1989).

Fotin, A. et al., "Parallel Thermodynamic Analysis of Duplexes on Oligodeoxyribonucleotide Microchips," Nucleic Acids Research, 216(6):1515-1521 (1998).

Fox, M. A., et al., "Light-Harvesting Polymer Systems," C&EN, pp. 38-48 (Mar. 15, 1993).

Fox, L. S., et al., "Gaussian Free-Energy Dependence of Electron-Transfer Rates in Iridium Complexes," Science, 247:1069-1071 (1990).

Francois, J-C., et al., "Periodic Cleavage of Poly(dA) by Oligothymidylates Covalently Linked to the 1,10-Phenanthroline-Copper Complex," Biochemistry, 27:2272-2276 (1988).

Friedman, A. E., et al., "Molecular 'Light Switch' for DNA: Ru(bpy)$_2$(dppz)$^{2+}$," J. Am. Chem. Soc., 112:4960-4962 (1990).

Fromherz, P., et al., "Photoinduced Electron Transfer in DNA Matrix from Intercalated Ethidium to Condensed Methylviologen," J. Am. Chem. Soc., 108:5361-5362 (1986).

Gardner, et al., "Application of conducting polymer technology in microsystems," Sensors and Actuators, A51:57-66 (1995).

Gregg, B. A., et al., "Redox Polymer Films Containing Enzymes. 1. A Redox-Conducting Epoxy Cement: Synthesis, Characterization, and Electrocatalytic Oxidation of Hydroquinone," J Phys. Chem., 95:5970-5975 (1991).

Gregg, B. A., et al., "Cross-linked redox gels containing glucose oxidase for amperometric biosensor applications," Anal. Chem., 62:258-263 (1990).

Guschin, D. et al., "Manual Manufacturing of Oligonucleotide, DNA, and Protein Microchips," Analytical Biochemistry, 250:203-211 (1997).

Guschin, D. et al., "Oligonucleotide Microchips as Genosensors for Determinative and Environmental Studies in Microbiology," 63(6):2397-2402 (1997).

Hashimoto, et al., "Sequence-Specific Gene Detection with a Gold Electrode Modified with DNA Probes and an Electrochemically Active Dye," Anal. Chem. 66:3830-3833 (1994).

Hegner, et al., "Immobilizing DNA on gold via thiol modification for atomic force microscopy imaging in buffer solutions," FEBS 336(3):452-456 (1993).

Heller, A., "Electrical Wiring of Redox Enzymes," Acc. Chem. Res., 23:128-134 (1990).

Heller et al., "Fluorescent Energy Transfer Oligonucleotide Probes," Fed. Proc. 46(6):1968 (1987) Abstract No. 248.

Heller, A., et al., "Amperometric biosensors based on three-dimensional hydrogel-forming epoxy networks," Sensors and Actuators, 13-14:180-183 (1993).

Ho "DNA-Mediated Electron Transfer and Application to 'Biochip' Development," Abstract. Office of Naval Research (Report Date: Jul. 25, 1991) 1-4, RR04106.

Hobbs et al., "Polynucleotides Containing 2'-Amino-2'deoxyribose and 2'-Azido-2'-deoxyriose," Biochemistry, 12(25):5138-5145 (1973).

Hsung, et al., "Thiophenol Protecting Groups for the Palladium-Catalyzed Heck Reaction: Efficient Syntheses of Conjugated Arylthiols," Tetrahedron Letters. 36(26):4525-4528 (1995).

Hsung, et al., "Synthesis and Characterization of Unsymmetric Ferrocene-Terminated Phenylethynyl Oligomers," Organometallics, 14:4808-4815 (1995).

Jenkins et al., A Sequence-Specific Molecular Light Switch: Tebhering of an Oligonucleotide to a Dipyridophenazine Complex of Ruthenium (II), J. Am. Chem. Soc., 114:8736-8738 (1992).

Johnston et al., "Trans-Dioxorhenium(V)-Mediated Electrocatalytic Oxidation of DNA at Indium Tin-Oxide Electrodes: Voltammetric Detection of DNA Cleavage in Solution," Inorg. Chem., 33:6388-6390 (1994).

Kamat et al., J. Phys. chem., 93(4):1405-1409 (1989). Abstract.

Katritzky, et al., "Pyridylethylation—A New Protection Method for Active Hydrogen Compounds," Tetrahedron Letters,25(12):1223-1226 (1984).

Kelley, S.O. and J.K. Barton, "Electrochemistry of Methylene Blue Bound to a DNA-Modified Electrode," Bioconjugate Chem., 8:31-37 (1997).

Kojima et al., "A DNA Probe of Ruthenium Bipyridine Complex Using Photocatalytic Activity," Chemistry Letter, pp. 1889-1982 (1989).

Korri-Youssoufi et al., "Toward Bioelectronics: Specific DNA Recognition Based on an Oligonucleotide-Functionalized Polypyrrole," J Am. Chem. Soc., 119(31):7388-7389 (1997).

Laviron, E., "A.C. Polarography and Faradaic Impedance of Strongly Adsorbed Electroactive Species. Part I: Theoretical and Experimental Study of a Quasi-Reversible Reaction in the Case of a Langmuir Isotherm," J. Electroanal. Chem., 97:135-149 (1979).

Laviron, E., "A.C. Polarography and Faradaic Impedance of Strongly Adsorbed Electoactive Species. Part III: Theoretical Complex Plane Analysis for a Surface Redox Reaction," J. Electroanal. Chem., 105:35-42 (1979).

Lee, et al., "Direct Measurement of the Forces Between Complementary Strands of DNA," Science, 266:771-773 (1994).

Lenhard, J.R., et al., "Part VII Covalent Bonding of a Reversible-Electrode Reactanbt to Pt Electrodes Using an organosilane Reagent" J. Electronal. Chem., 78:195-201 (1977).

Lincoln et al., "Shorting Circuiting the Molecular Wire," J. Am. Chem. Soc., 119(6)1454-1455 (1997).

Lipkin "Identifying DNA by the Speed of Electrons," Science News, 147(8):117 ( 1995).

Livshits, M. et al., "Theoretical Analysis of the Kinetics of DNA Hybridization with Gel-Immobilized Oligonucleotides," Biophysical Journal, 71:2795-2801 (1996).

Maskos, et al., "Oligonucleotide hybridisations on glass supports: a novel linker for oligonucleotide synthesis and hybridisation properties of oligonucleotides synthesised in situ," Nucleic Acids Research, 20(7):1679-1684 (1992).

McGee, et al., "2'-Amino-2'-deoxyuridine via an Intramolecular Cyclization of a Trichloroacetimidate," J. Org. Chem., 61:781-785 (1996).

Meade, T. J., et al., "Electron Transfer through DNA: Site-Specific Modification of Duplex DNA with Ruthenium Donors and Acceptors," Angew Chem. Int. Ed. Engl., 34:352-354 (1995).

Meade, T. J., "Driving-Force Effects on the Rate of Long-Range Electron Transfer in Ruthenium-Modified Cytochrome c," J. Am. Chem. Soc., 111:4353-4356 (1989).

Mestel, "'Electron Highway' Points to Identity of DNA," New Scientist, p. 21 (1995).

Millan, K.M. and Mikkelsen, S.R., "Sequence-Selective Biosensor for DNA Based on Electroactive Hybridization Indicators," Anal. Chem., 65:2317-2323 (1993).

Millan, K.M., et al., "Covalent Immobilization of DNA onto Glassy Carbon Electrodes," Electroanalysis, 4(10):929-932 (1992).

Millan, et al., "Voltammetric DNA Biosensor for Cystic Fibrosis Based on a Modified Carbon Paste Electrode," Anal. Chem., 66:2943-2948 (1994).

Miller, C., "Absorbed ω-Hydroxy Thiol Monolayers on Gold Electrodes: Evidence for Electron Tunneling to Redox Species in Solution," J. Phys. Chem., 95:877-886 (1991).

Mirkin et al., "A DNA-based Method for Ratioally Assembling Nonoparticles into Macroscopic Materials," Nature, 382:607-609 (1996).

Mirzabekov, A. et al., "Dna Sequencing by Hybridization—a Megasequencing Method and a Diagnostic Tool," Tibtech, 12:27-32 (1994).

Mitchell et al., "Programmed Assembly of DNA Functionalized Quantum Dots," J. Am. Chem. Soc., 121:8122-8123 (1999).

Mucic et al., "Synthesis and Characterization of DNA with Ferrocenyl Groups Attached to their 5'-Termini: Electrochemical Characterization of a Redox-Active Nucleotide Monolayer," Chem. Commun., pp. 555-557 (1996).

Mucic et al., "DNA-Directed Synthesis of Binary Nanoparticle Network Materials," J. Am. Chem. Soc., 120:12674-12675 (1998).

Murphy, C. J., et al., "Long-Range Photoinduced Electron Transfer Through a DNA Helix," Science, 262:1025-1029 (1993).

Orellana, G., et al., "Photoinduced Electron Transfer Quenching of Excited Ru(II) Polypyridyls Bound to DNA: The Role of the Nucleic Acid Double Helix," Photochemistry and Photobiology, 54(4):499-509 (1991).

Palecek, "From Polarography of DNA to Microanalysis with Nucleic Acid-Modified Electrodes," Electroanalysis. 8(1):7-14 (1996).

Parinov, S., "DNA Sequencing by Hybridization to microchip octa- and Decanucleotides Extended by Stacked Pentanucleotides," Nucleic Acids Research, 24(15):2998-3004 (1996).

Paterson, "Electric Genes: Current Flow in DNA Could Lead to Faster Genetic Testing," Scientific American, 33 (May 1995).

Proudnikov, D. "Immobilization of DNA in Polyacrylamide Gel for the manufacture of DNA and DNA-Oligonucleotide Microchips," Analytical Biochemistry, 259:34-41 (1998).

Proudnikov, D. et al., "Chemical Methods of DNA and RNA Fluorescent Labeling," Nucleic Acids Research, 24(22):4535-4542 (1996).

Purugganan, M.D., et al., Accelerated Electron Transfer Between Metal Complexes Mediated by DNA, Science, 241:1645-1649 (1988).

Reimers et al., "Toward Efficient Molecular Wires and Switches: the Brooker Ions," Biosystems, 35:107-111 (1995).

Rhodes, D. and A. Klug, "Helical Periodicity of DNA Determined by Enzyme Digestion," Nature, 286:573-578 (1980).

Risser, S. M., et al., "Electron Transfer in DNA: Predictions of Exponential Growth and Decay of Coupling with Donor-Acceptor Distance," J. Am. Chem. Soc., 115(6):2508-2510 (1993).

Sato, Y., et al., "Unidirectional Electron transfer at Self-Assembled Monolayers of 11-Ferrocenyl-1-undecanethiol on Gold," Bull. Chem. Soc. Jpn., 66(4): 1032-1037 (1993).

Satyanarayana, S., et al., "Neither γ- nor Λ-Tris(phenanthroline)ruthenium(II) Binds to DNA by Classical Intercalation," Biochemistry, 31(39):9319-9324 (1992).

Schreiber, et al., "Bis(purine) Complexes of trans-a$_2$Pt$^{II}$: Preparation and X-ray Structures of Bis(9-methyladenine) and Mixed 9-Methyladenine, 9-Methylguanine Complexes and Chemistry Relevant to Metal-Modified Nucelobase Triples and Quartets," J. Am. Chem. Soc. 118:4124-4132 (1996).

Schuhmann, W., et al., "Electron Transfer between Glucose Oxidase and Electrodes via Redox Mediators Bound with Flexible Chains to the Enzyme Surface," J. Am. Chem. Soc., 113:1394-1397 (1991).

Schumm, et al., "Iterative Divergent/Convergent Approach to Linear Conjugated Oligomers by Successive Doubling of the Molecular Length: A Rapid Route to a 128 Å-Long Potential Molecular Wire," Angew. Chem. Int. Ed. Engl., 33(11):1360-1363 (1994).

Sigal et al., "A Self-Assembled Monolayer for the Binding and Study of Histidine-Tagged Proteins by Surface Plasmon Resonance," Anal. Chem., 68(3):490-497 (1996).

Sloop et al., "Metalloorganic labels for DNA sequencing and mapping," New. J. Chem., 18:317-326 (1994).

Southern, et al., "Arrays of complementary oligonucleotides for analysing the hybridisation behaviour of nucleic acids," Nucleic Acids Research, 22(8):1368-1373 (1994).

Storhoff et al., "One-Pot Colorimetric Differentiation of Polynucleotides with Single Base Imperfections Using Gold Nanoparticles Probes," J. Am. Chem. Soc., 120:1959-1964 (1998).

Strobel, S. A., et al., "Site-Specific Cleavage of a Yeast chromosome by Oligonucleotide-Directed Triple-Helix Formation," Science, 249:73-75 (1990).

Su, et al., "Interfacial Nucleic Acid Hybridization Studied by Random Primer $^{32}$P Labelling and Liquid-Phase Acoustic Network Analysis," Analytical Chemistry, 66(6):769-777 (1994).

Telser, J., et al., "DNA Oligomers and Duplexes Containing a Covalently Attached Derivative of Tris(2,2'-bipyridine)ruthenium(II): Synthesis and Characterization by Thermodynamic and Optical Spectroscopic Measurements," J. Am. Chem. Soc., 111:7221-7226 (1989).

Telser, J., et al., "DNA Duplexes Covalently Labeled at Two Sites: Synthesis and Characterization by Steady-State and Time-Resolved Optical Spectroscopies," J. Am. Chem. Soc., 111:7226-7232 (1998).

Timofeev, E. et al., "Regioselective Immobilization of Short Oligonucleotides to Acrylic Copolymer Gel," Nucleic Acids Research, 24(16): 3142-3148 (1996).

Timofeev, E. et al., "Methidium Intercalator Inserted into Synthetic Oligonucleotides," Tetrahedron Letters, 37(47):8467-8470 (1996).

Tour, "Conjugated Macromolecules of Precise Length and Constitution. Organic Synthesis for the Construction of Nanoarchitectures,"Chem. Rev., 96:537-553 (1996).

Tour, et al., "Self-Assembled Monolayers and Multilayers of Conjugated Thiols, α-ξ-Dithiols, and Thioacetyl-Containing Adsorbates. Understanding Attachments between Potential Molecular Wires and Gold Surfaces," J. Am. Chem. Soc., 117:9529-9534 (1995).

Tullius, T.D. and B.A. Dombroski, "Iron(II) EDTA Used to Measure the Helical Twist Along Any DNA :Molecule," Science, 230:679-681 (1985).

Turro, N. J., et al., "Molecular Recognition and Chemistry in Restricted Reaction Spaces. Photophysics and Photoinduced Electron Transfer on the Surfaces of Micelles, Dendrimers, and DNA," Acc. Chem. Res., 24:332-340 (1991).

Turro, N., et al. "Photoelectron Transfer Between Molecules Adsorbed in Restricted Spaces," Photochem. Convers. Storage Sol. Energy, Proc. Int. Conf., 8th, pp. 121-139 (1990).

Uosake, K., et al., "A Self-Assembled Monolayer of Ferrocenylalkane Thiols on Gold as an Electron Mediator for the Reduction of Fe(III)-EDTA in Solution," Electrochemica Acta., 36(11/12):1799-1801 (1991).

Van Ness, J., et al., "A Versatile Solid Support System for Oligodeoxynucleotide Probe-Based Hybridization Assays," Nucleic Acids Research, 19(12):3345-3350 (1991).

Velev et al., "In Situ Assembly of Colloidal Particles into Miniaturized Biosensors," The ACS Journal of Surfaces and Colloids, Langmuir, 15(11):3693-3698 (1999).

Watson et al., "Hybrid Nanoparticles with Block Copolymer Shell Structures," J. Am. Chem. Soc., 121:462-463 (1999).

Weber, et al., "Voltammetry of Redox-Active Groups Irreversibly Adsorbed onto Electrodes. Treatment Using the Marcus Relation between Rate and Overpotential," Anal. Chem., 66:3164-3172 (1994).

Williams, et al., "Studies of oligonucleotide interactions by hybridisation to arrays: the influence of dangling ends on duplex yield," Nucleic Acids Research, 22(8):1365-1367 (1994).

Winkler, J. R., et al., "Electron Transfer in Ruthenium-Modified Proteins," Chem. Rev., 92:369-379 (1992).

Xu, et al., "Immobilization and Hybridization of DNA on an Aluminum(III) Alkanebisphosphonate Thin Film with Electrogenerated Chemiluminescent Detection," J. Am. Chem. Soc., 117:2627-2631 (1995).

Xu, et al., "Immobilization of DNA on an Aluminum(III) alkaneobisphosphonate Thin Film with Electrogenerated Chemiluminescent Detection," J. Am. Chem. Soc., 116:8386-8387 (1994).

Yang, et al., "Growth and Characterization of Metal(II) Alkaneobisphosphonate Multilayer Thin Films on Gold Surfaces," J. Am. Chem. Soc., 115:11855-11862 (1993).

Yershov, G. et al., "DNA Analysis and Diagnostics on Oligonucleotide Microchips," Proc. Natl. Acad. Sci. USA, 93:4913-4918 (1996).

Zhou, et al., "Fluorescent Chemosensors Based on Energy Migration in Conjugated Polymers: The Molecular Wire Approach to Increased Sensitivity," J. Am. Chem. Soc., 117:12593-12602 (1995).

Baner et al., "Signal amplification of padlock probes by rolling circle replication," Nucleic Acids Research, 26(22):5073-5078 (1998).

* cited by examiner

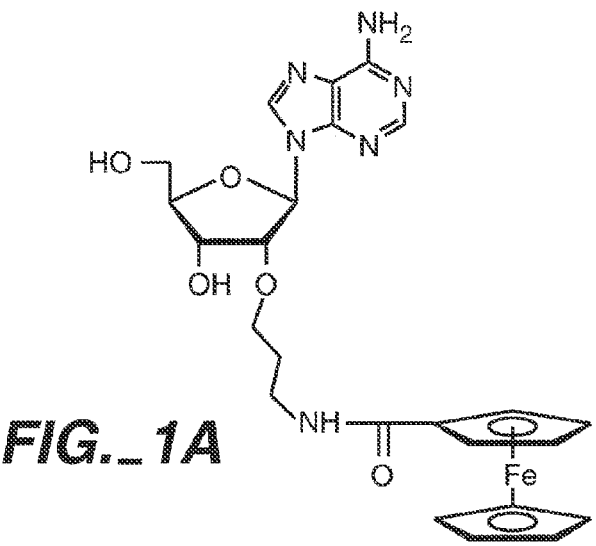
FIG._1A
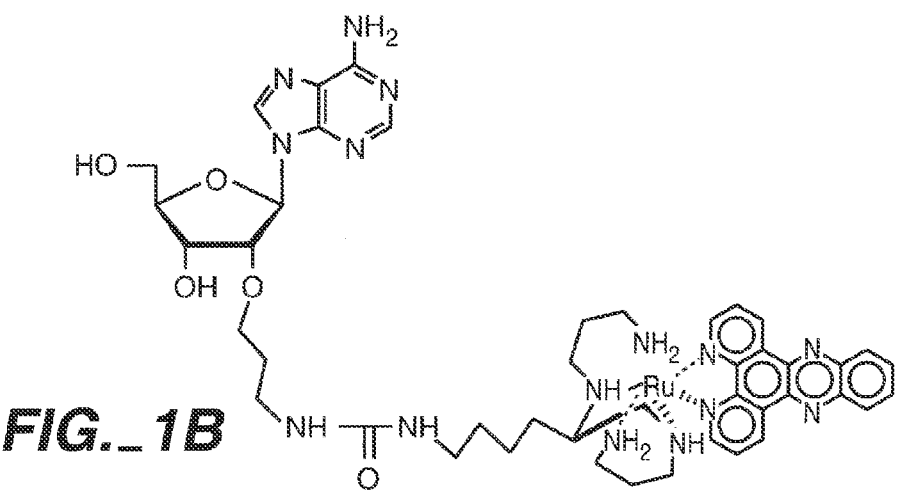
FIG._1B
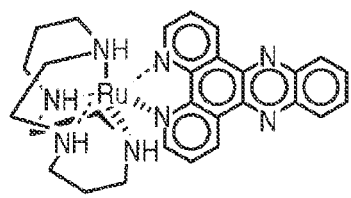
FIG._1C
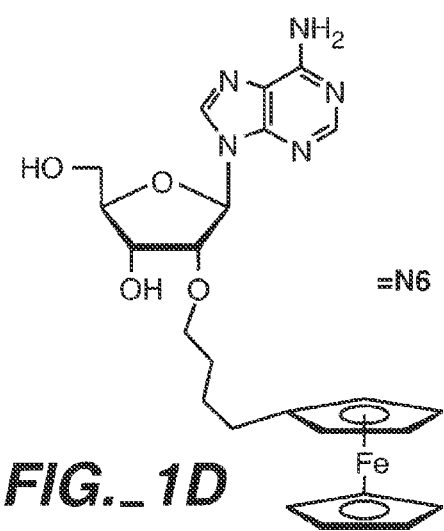
FIG._1D

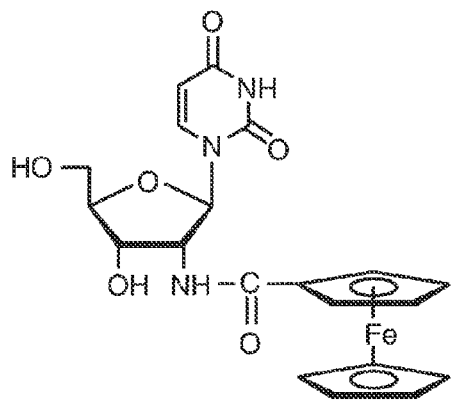
*FIG._1E*
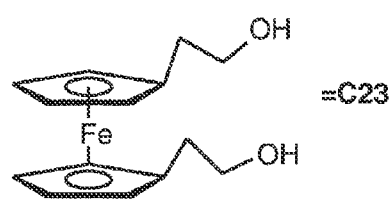
*FIG._1F*
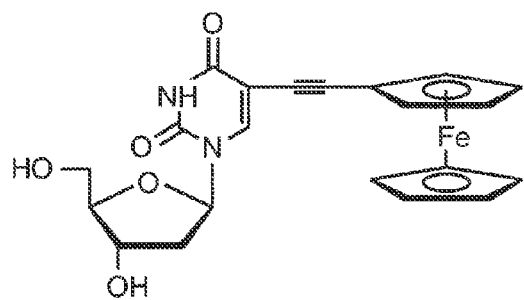
*FIG._1G*
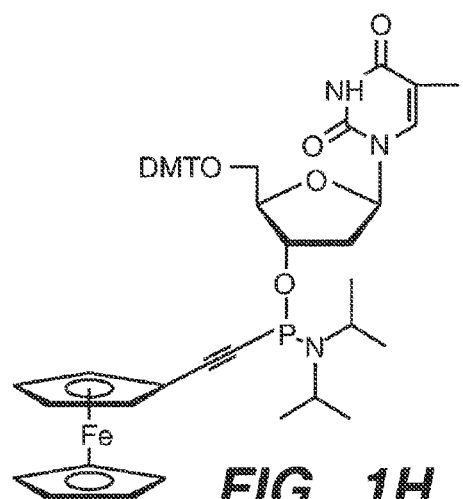
*FIG._1H*
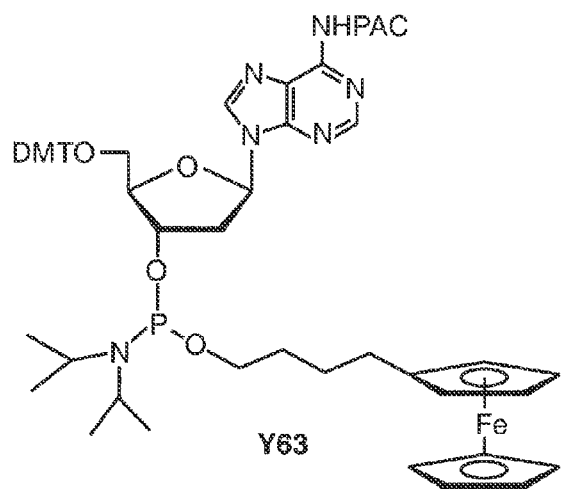
*FIG._1I*
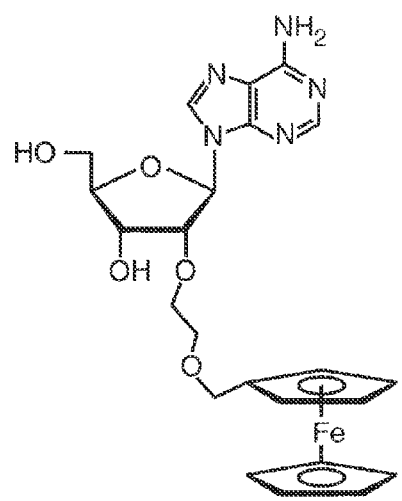
*FIG._1J*

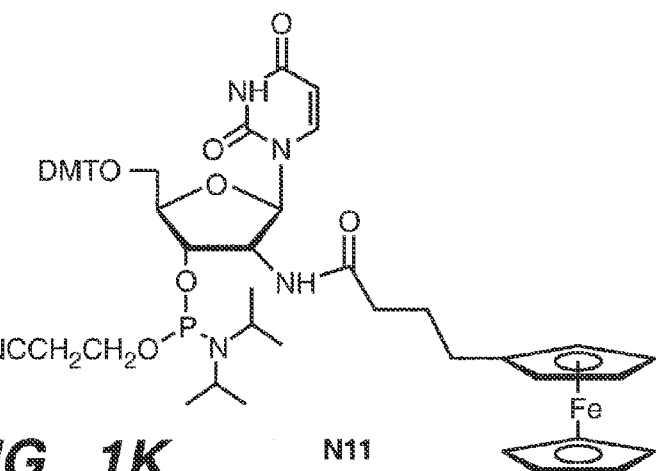
FIG._1K
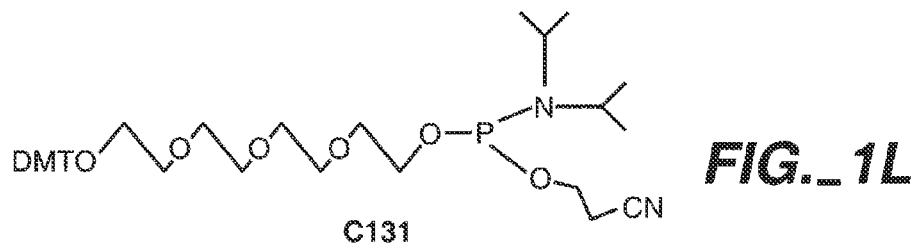
FIG._1L
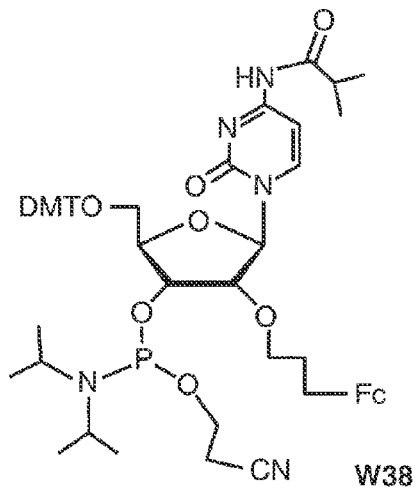
FIG._1M
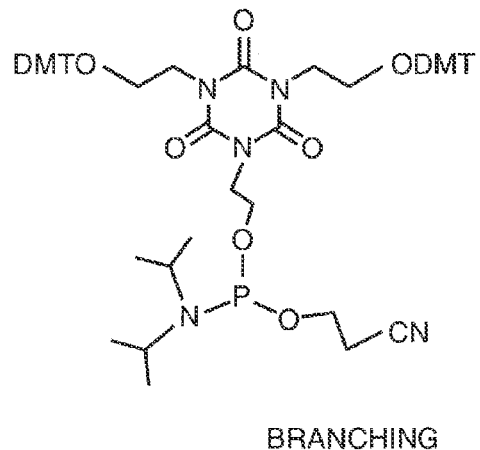
FIG._1N
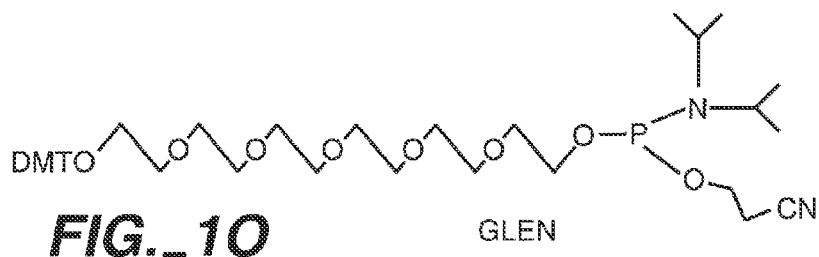
FIG._1O

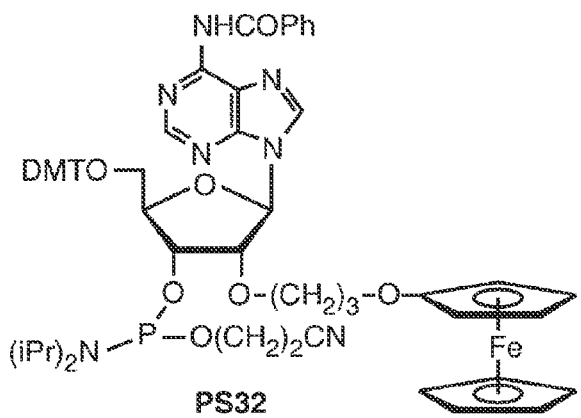
FIG._1P
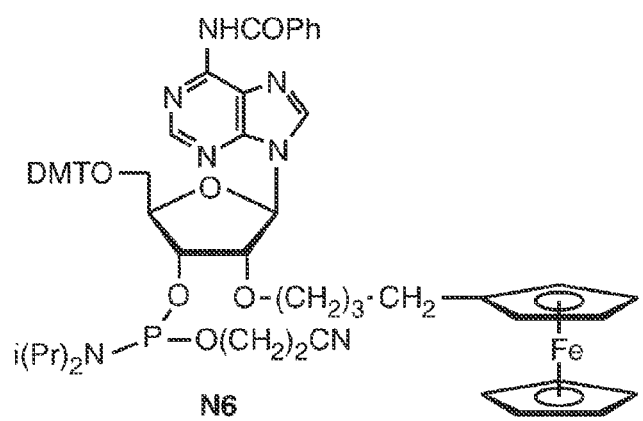
FIG._1Q
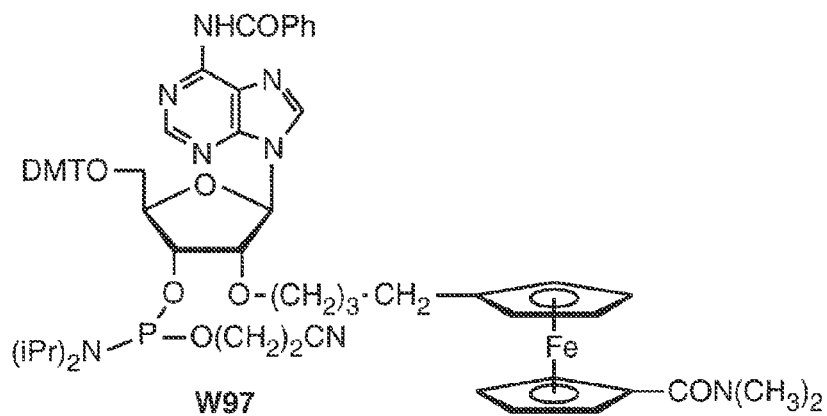
FIG._1R

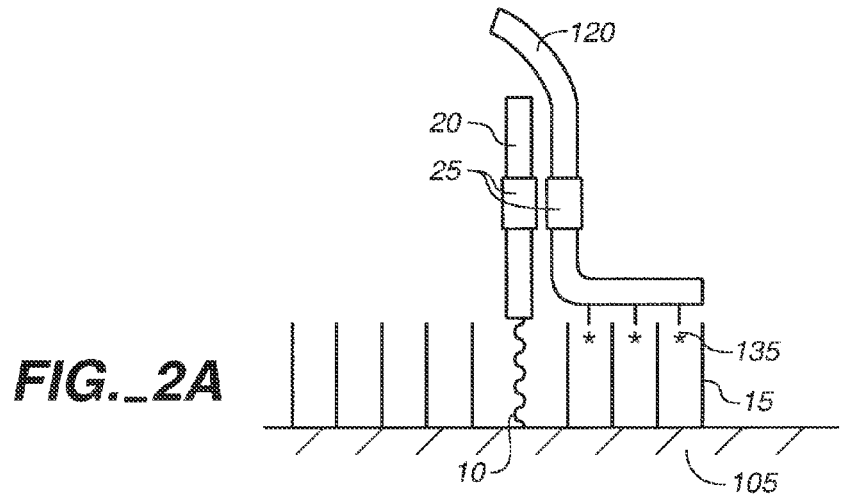
FIG._2A
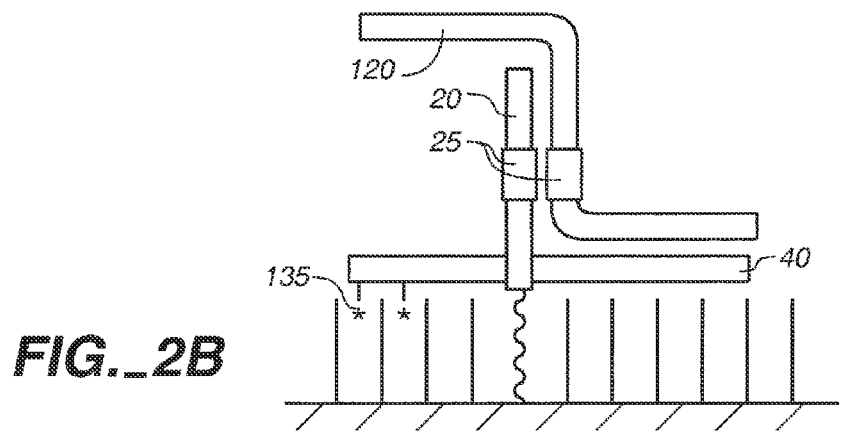
FIG._2B
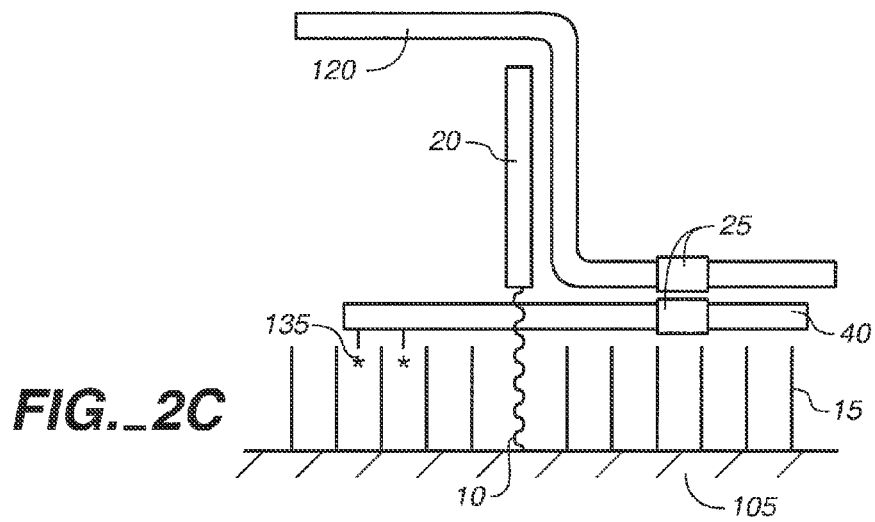
FIG._2C

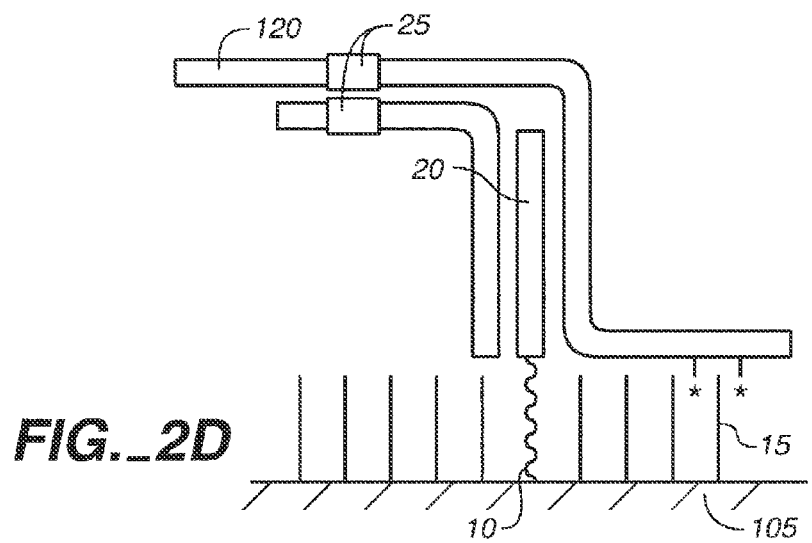
FIG._2D
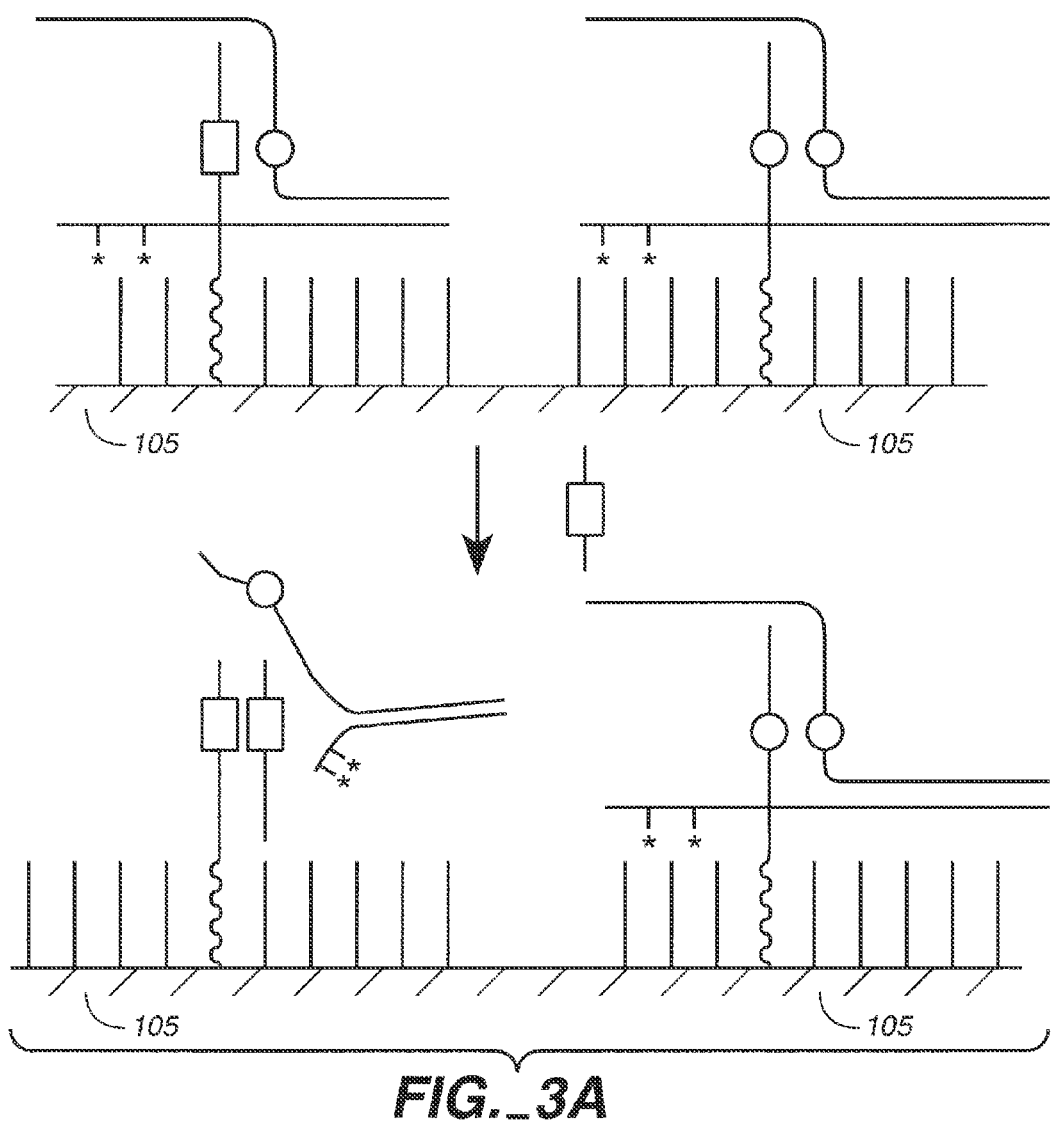
FIG._3A

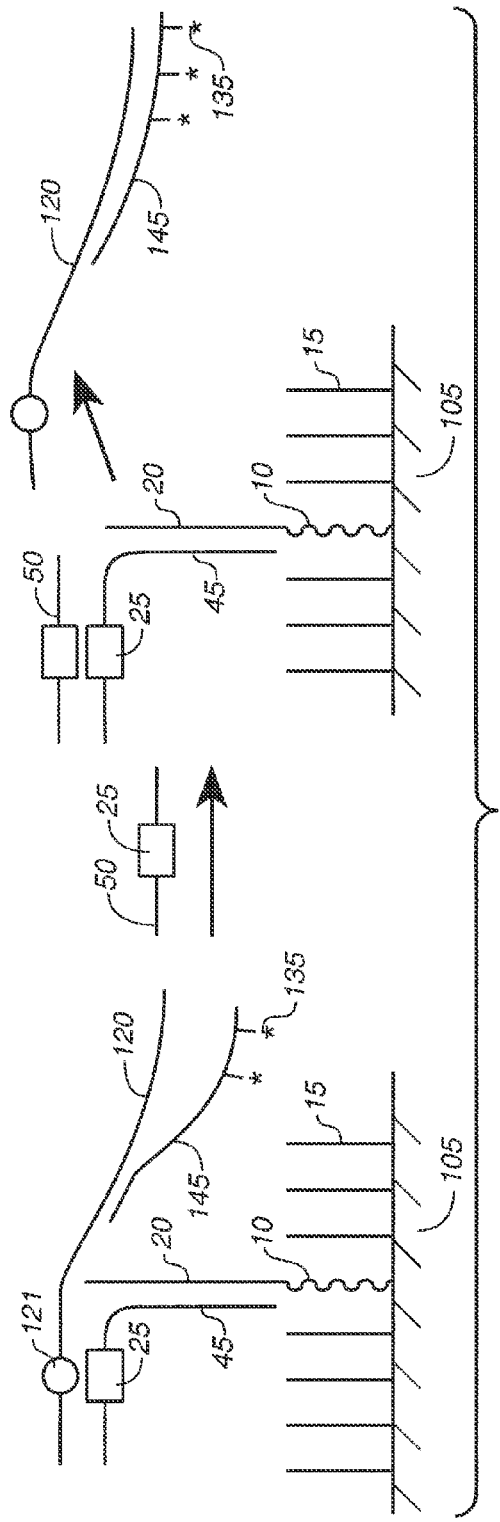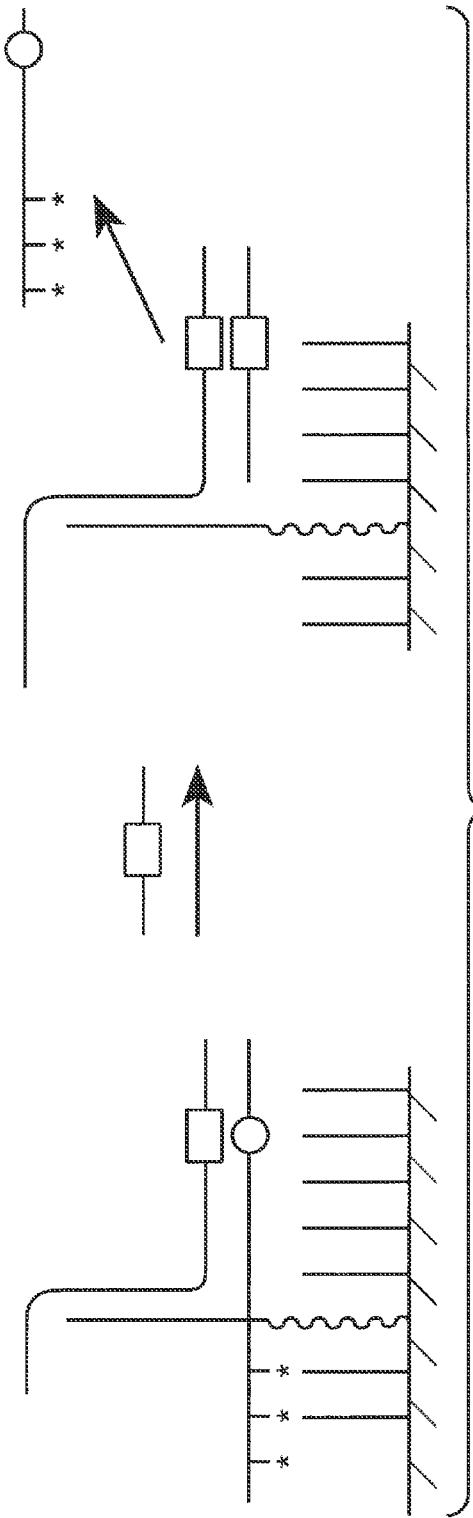
FIG._3B
FIG._3C

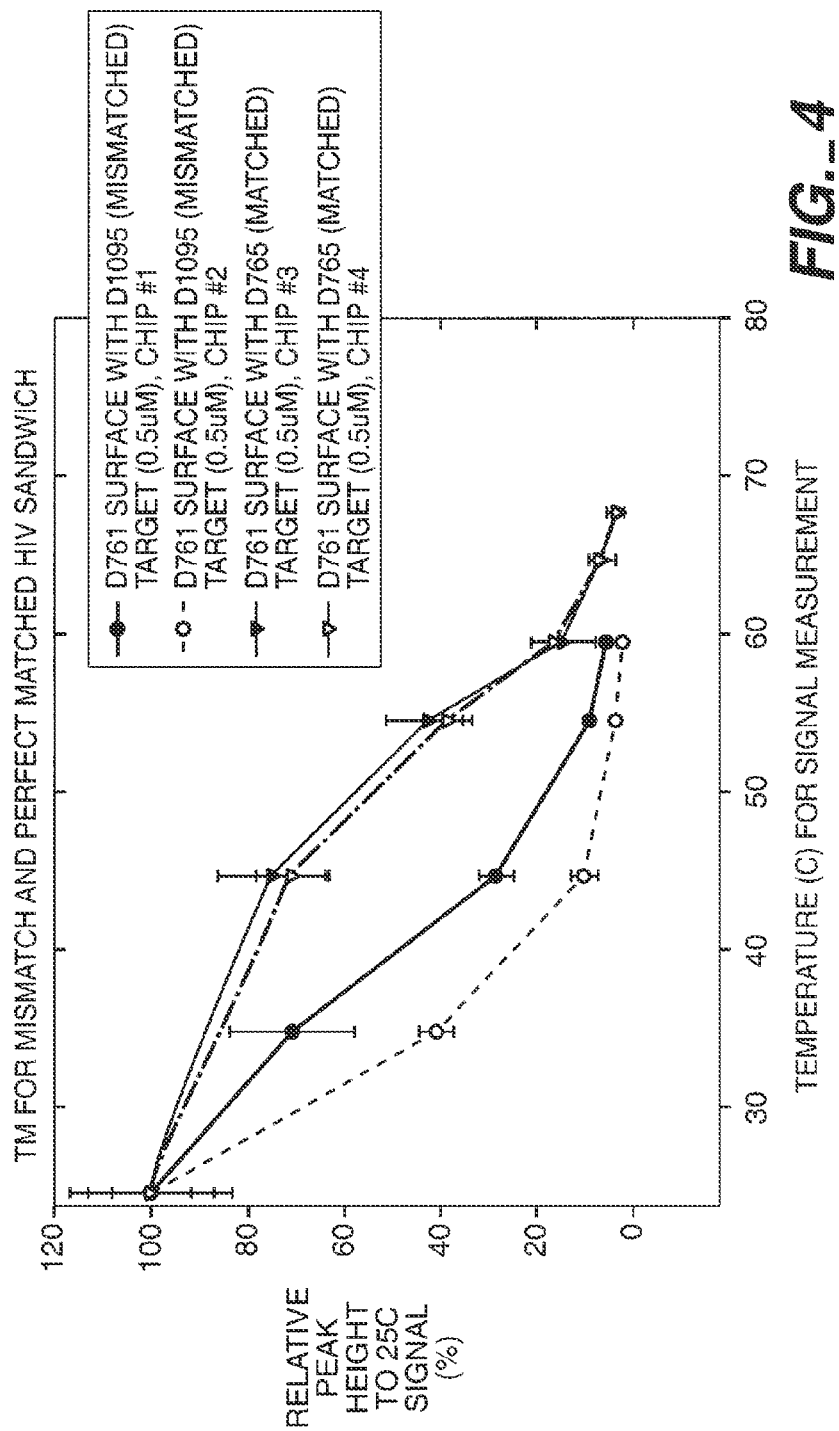

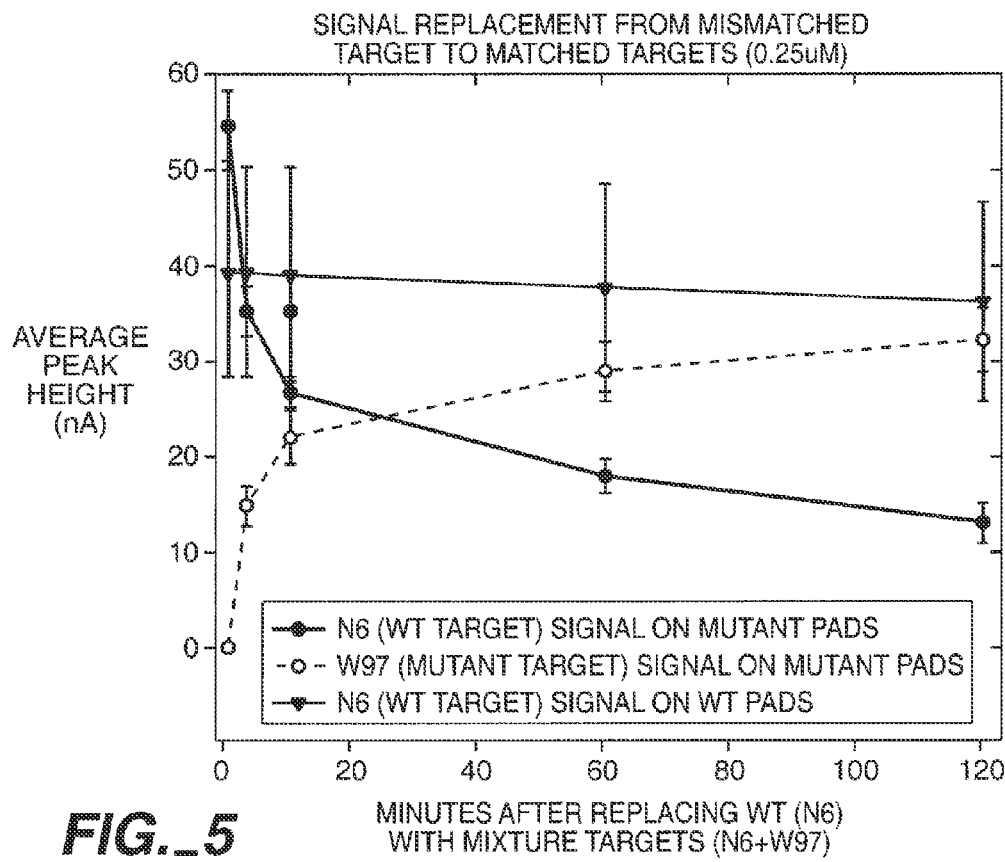
FIG._5
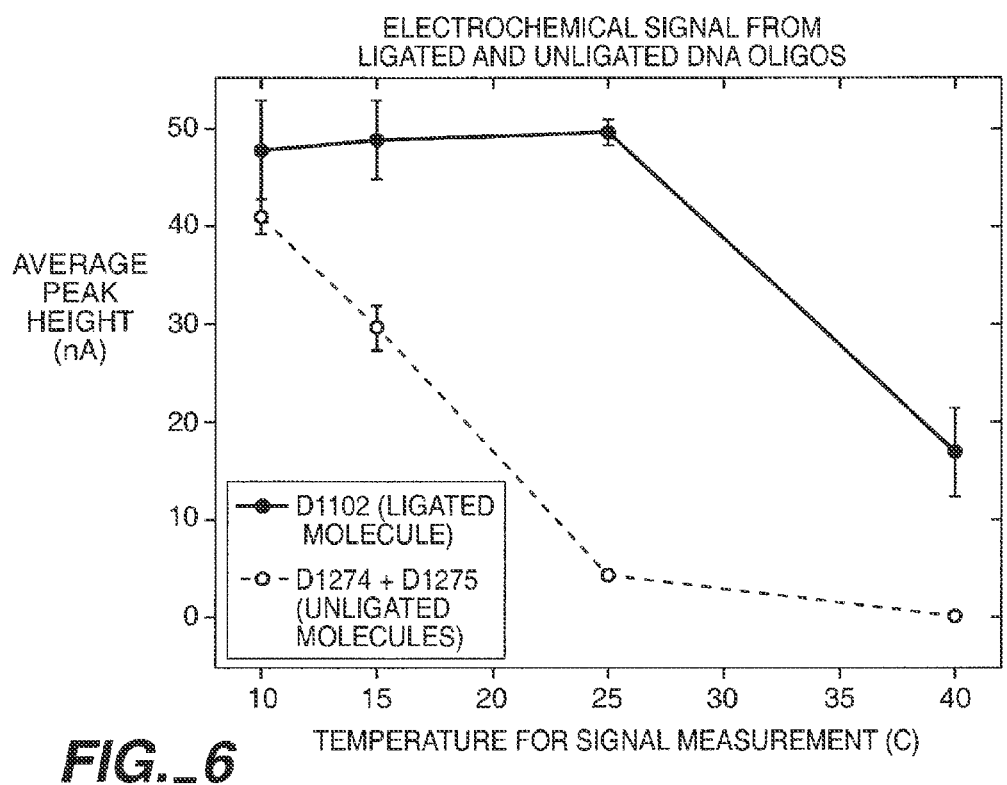
FIG._6

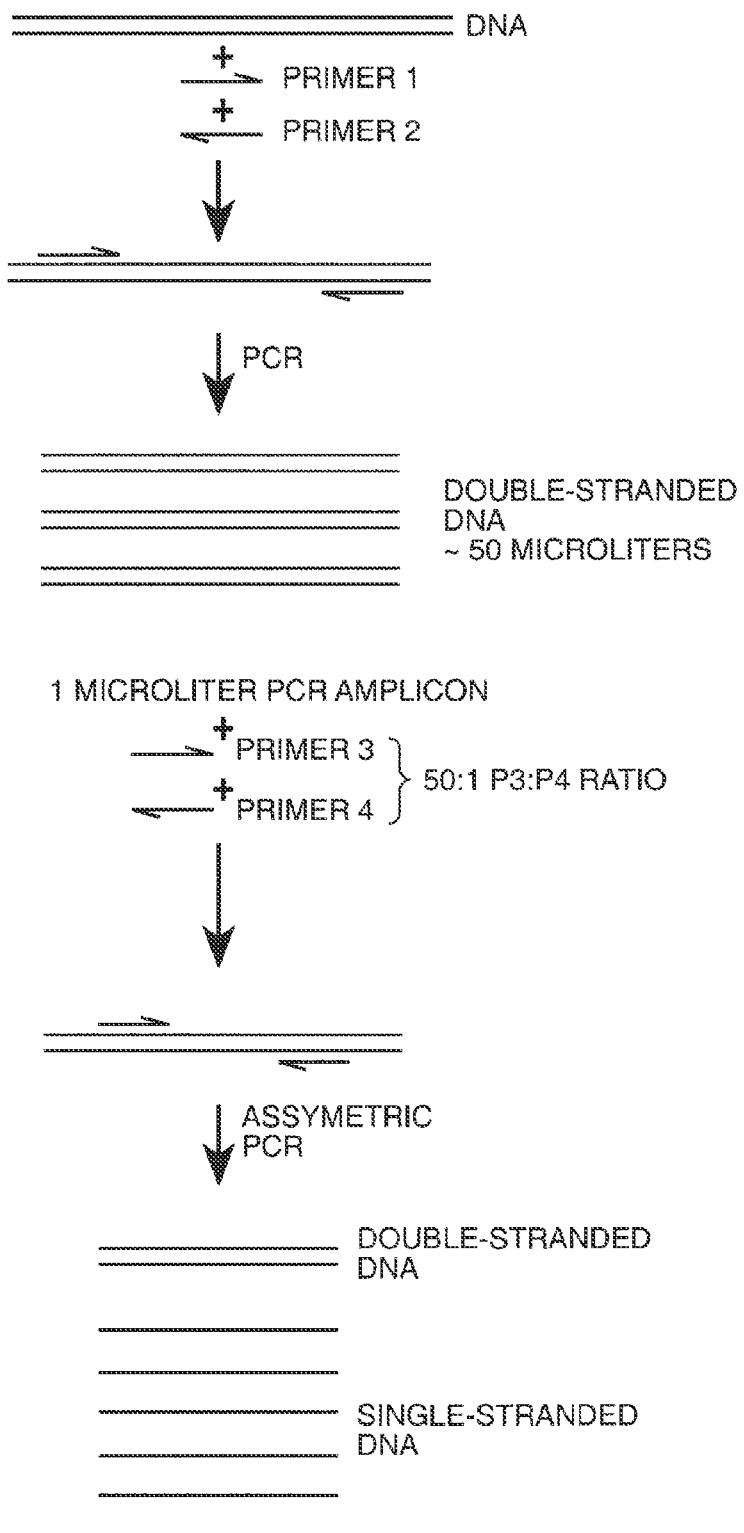
FIG._7

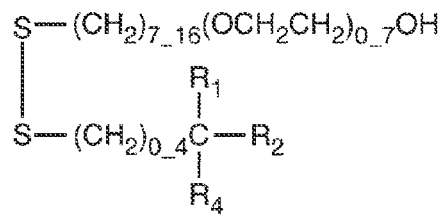
R₁, R₂, AND R₃: H, CH₃, t-BUTYL, CYCLOALKYL, CH₂OH, CH₂NH₂, CONH₂, COOH, CH₂OPO₃²⁻, AROMATIC, ADAMANTYL
*FIG._8A*
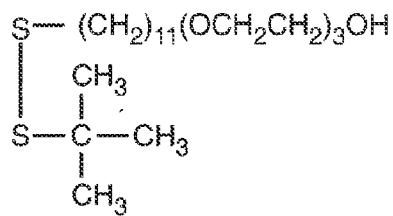 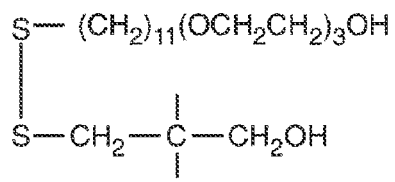
*FIG._8B*
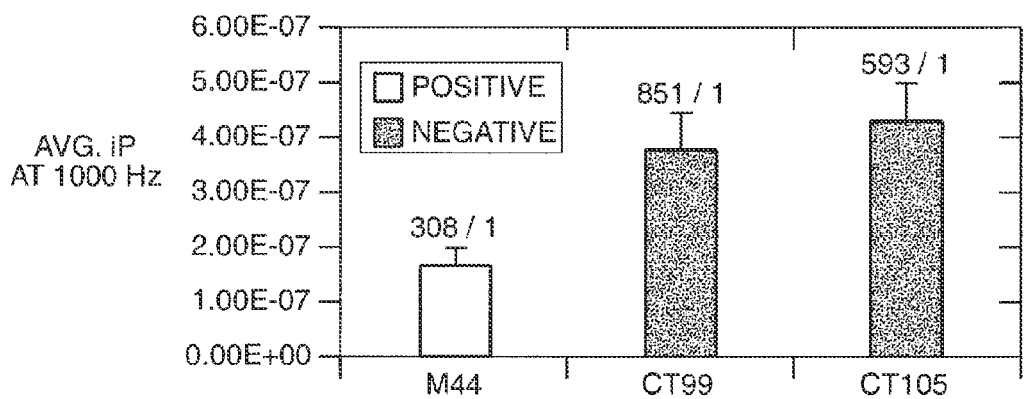
*FIG._8C*

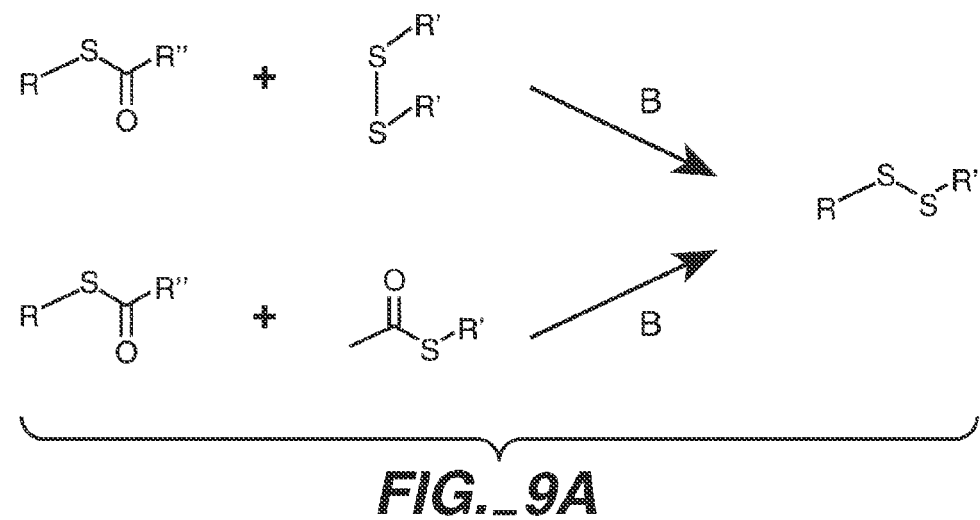
*FIG._9A*
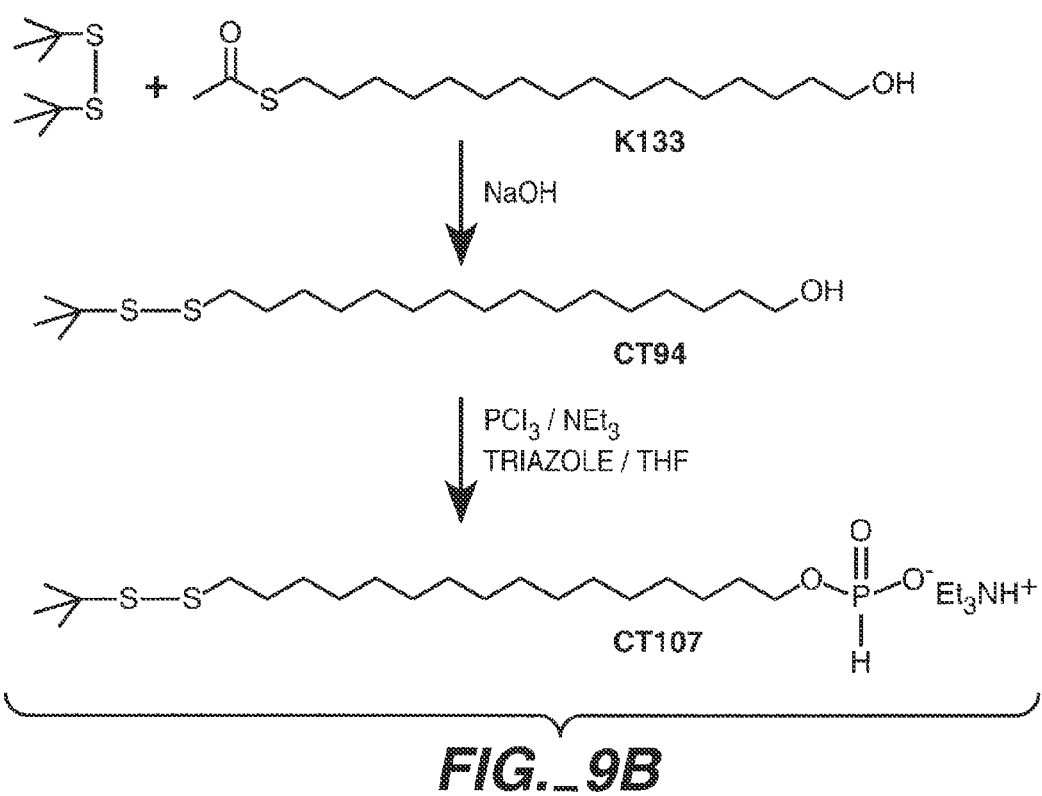
*FIG._9B*

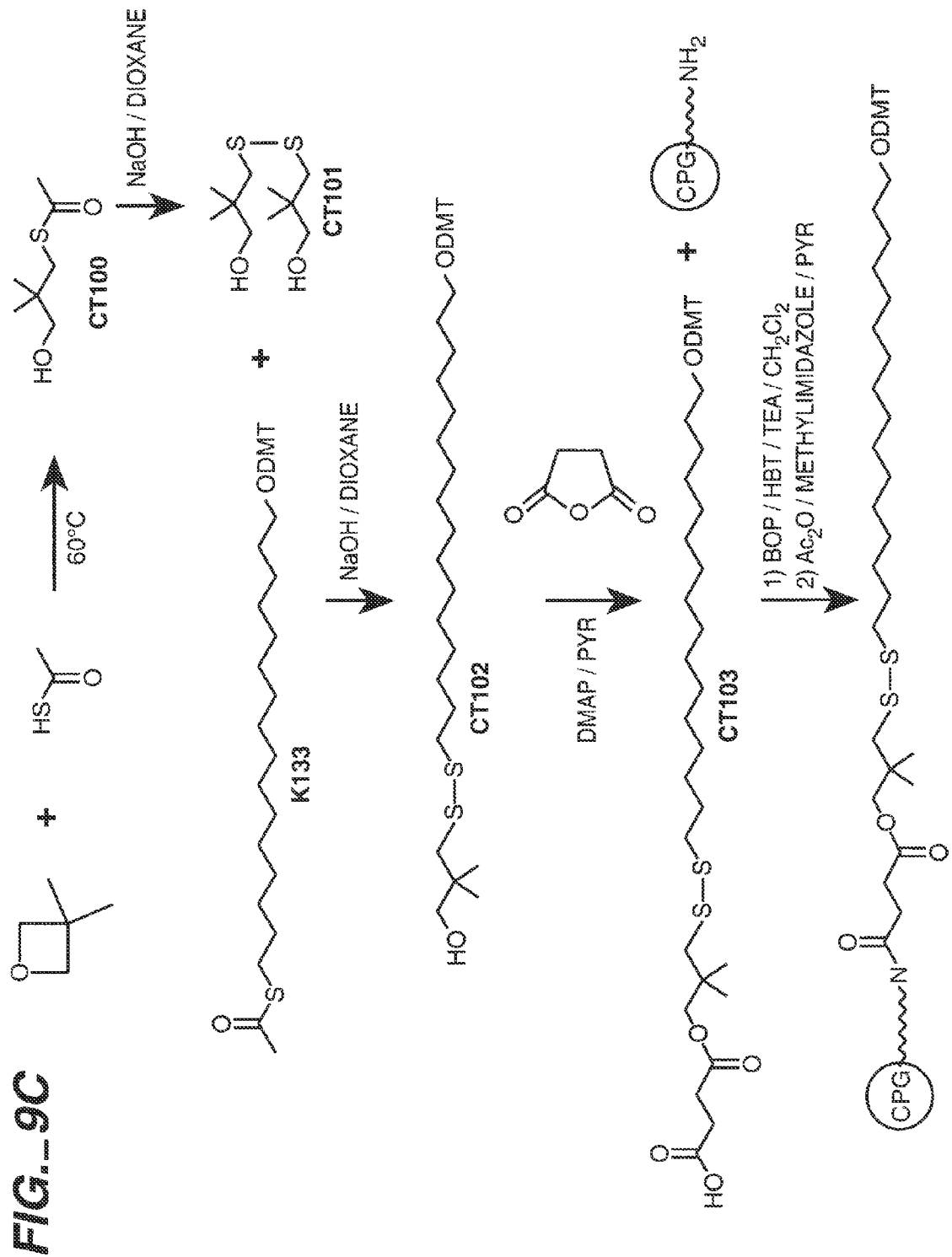
FIG._9C

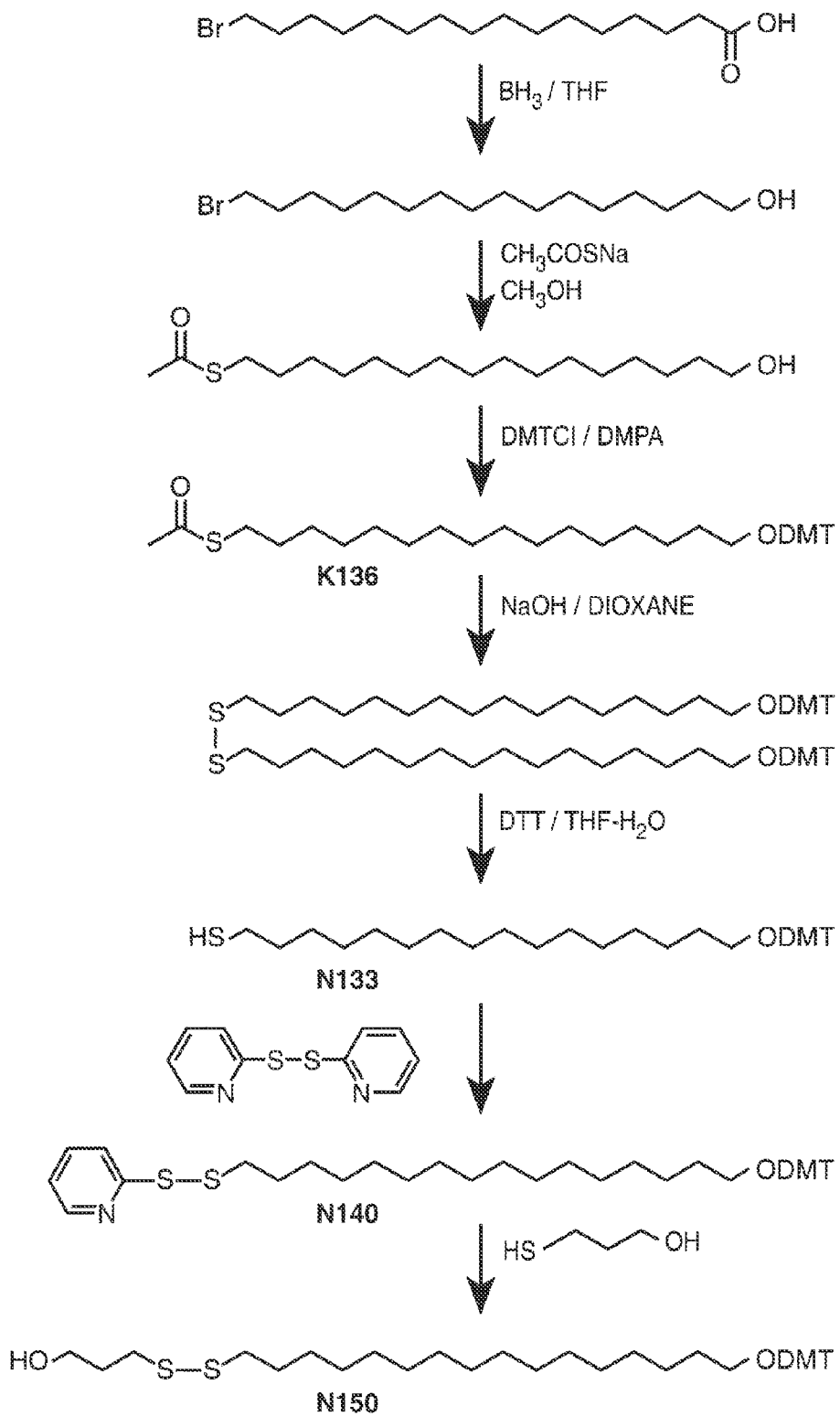
FIG._9D-1

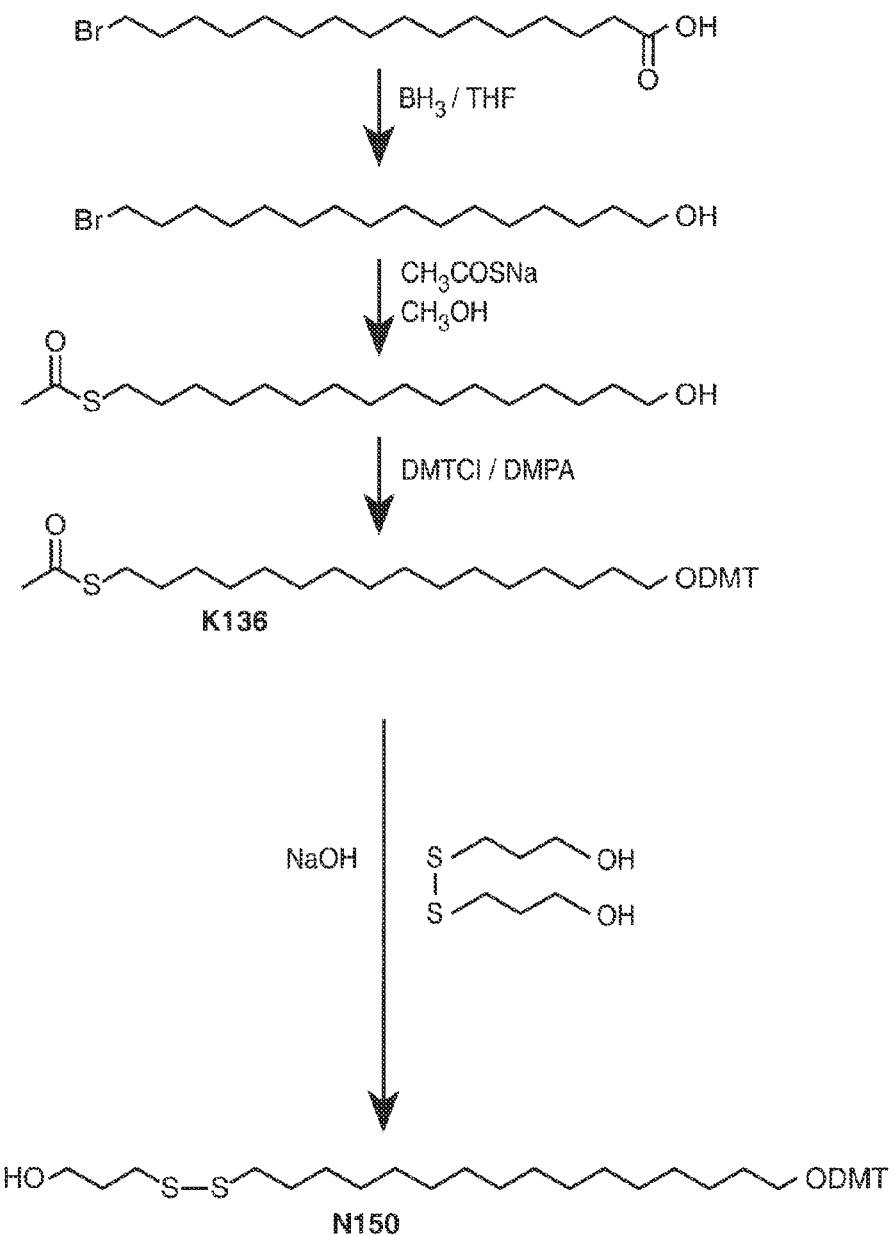
FIG._9D-2

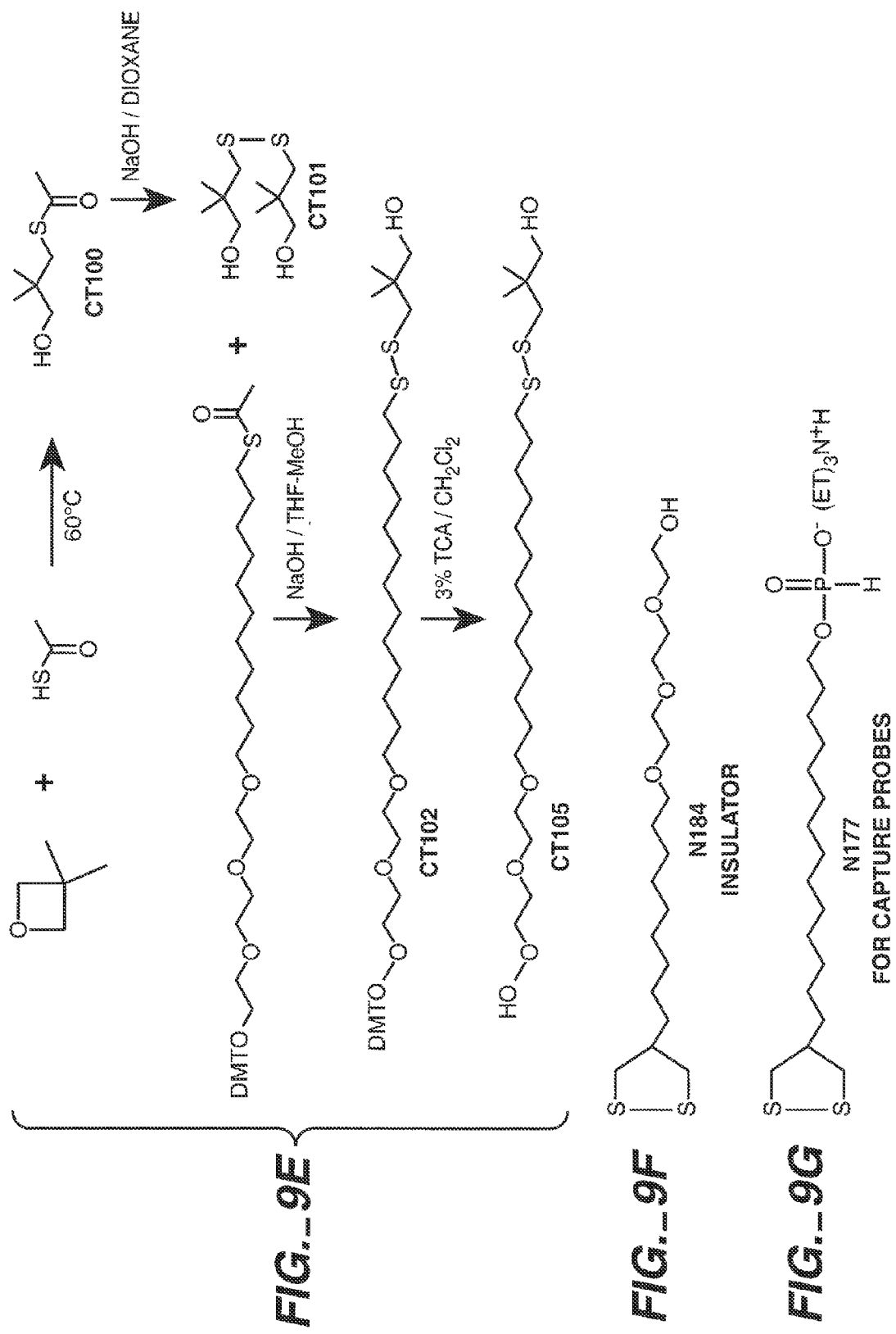
FIG._9E
FIG._9F
FIG._9G

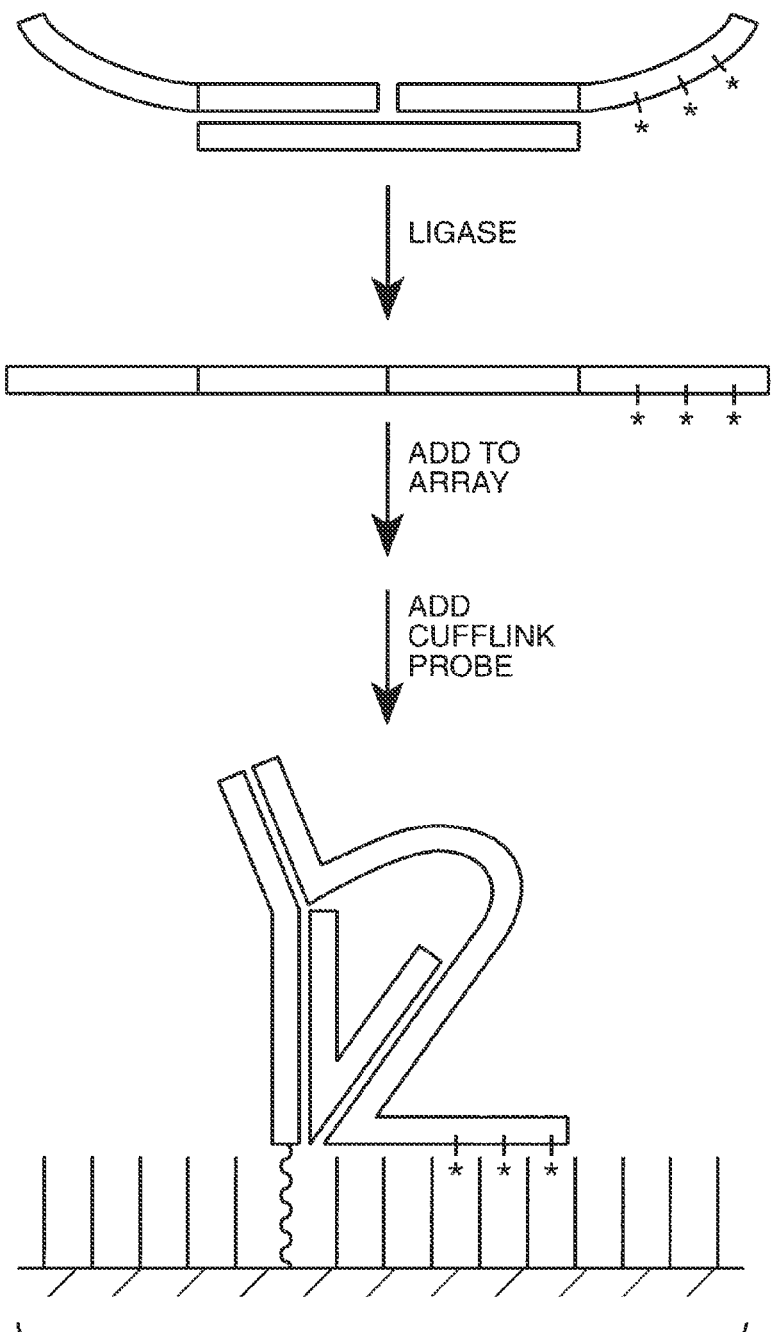
FIG._10

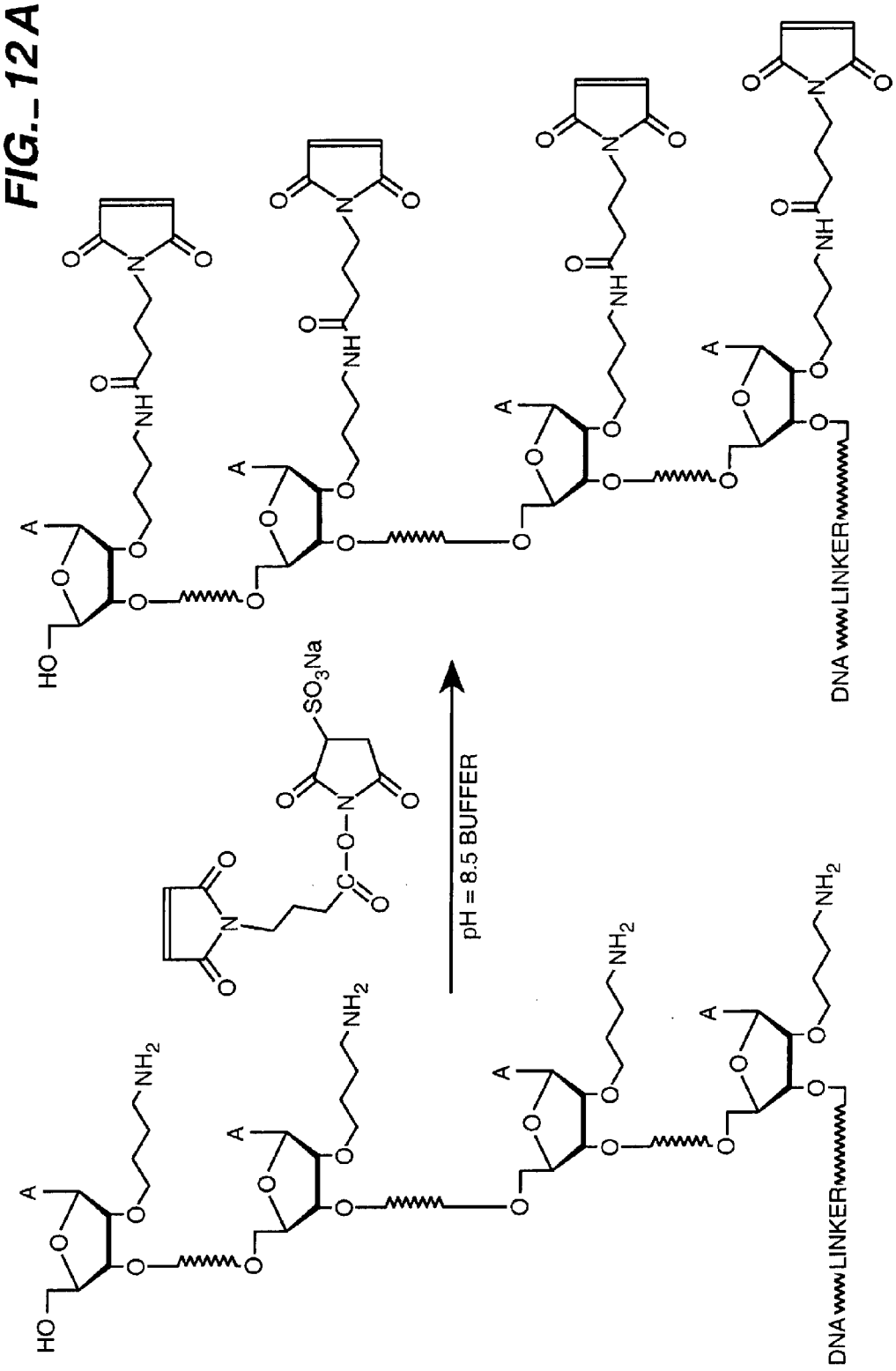
FIG._12A

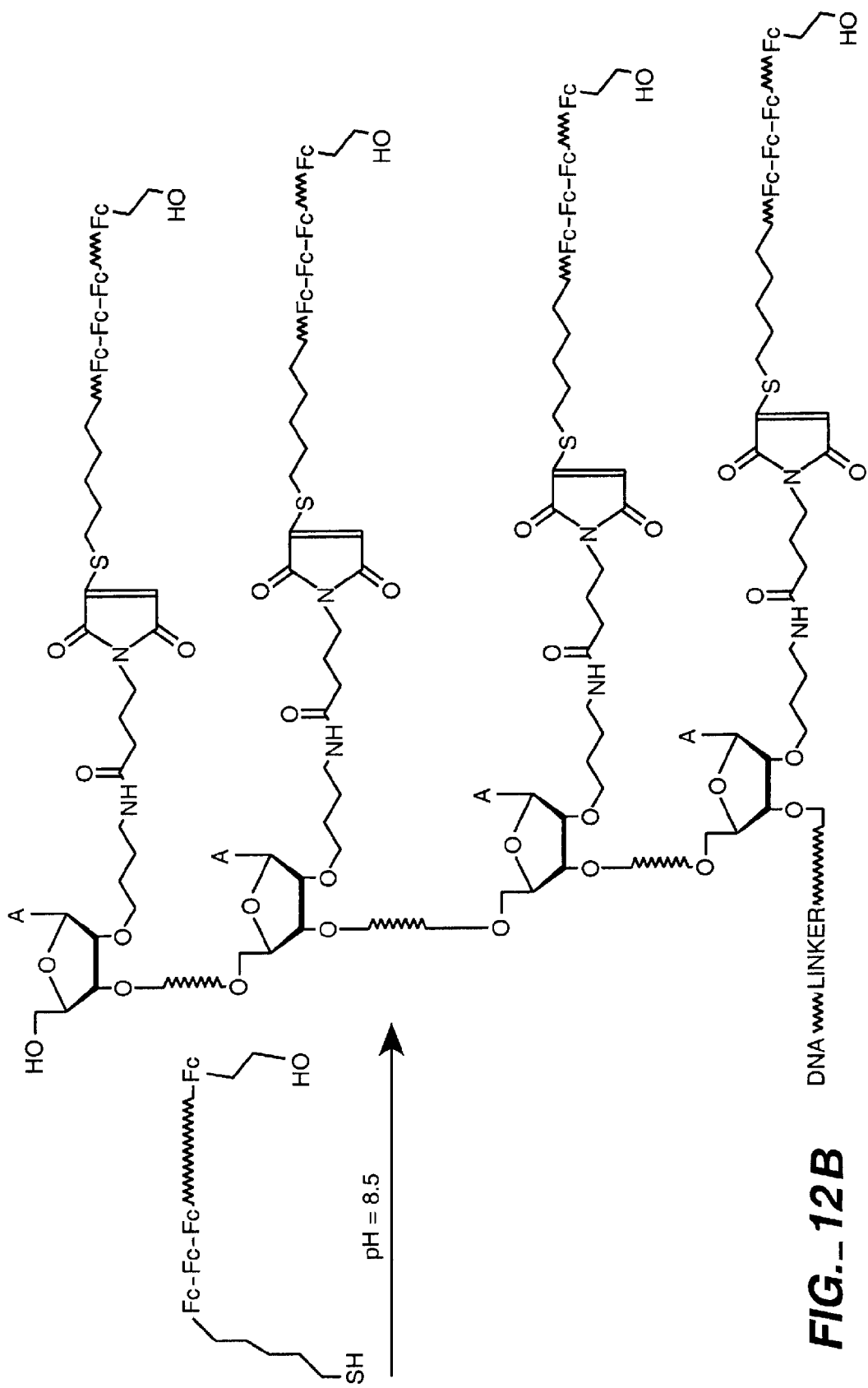
FIG._12B

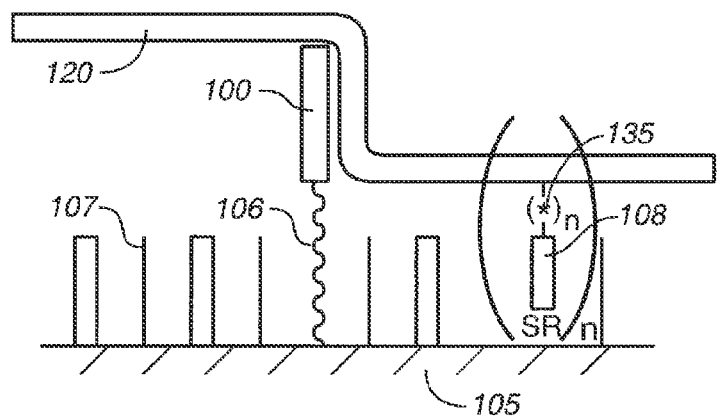
FIG._13A
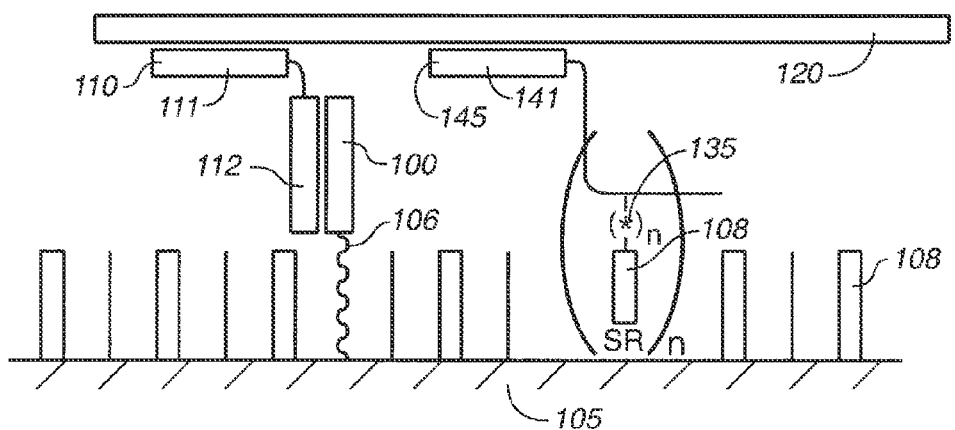
FIG._13B

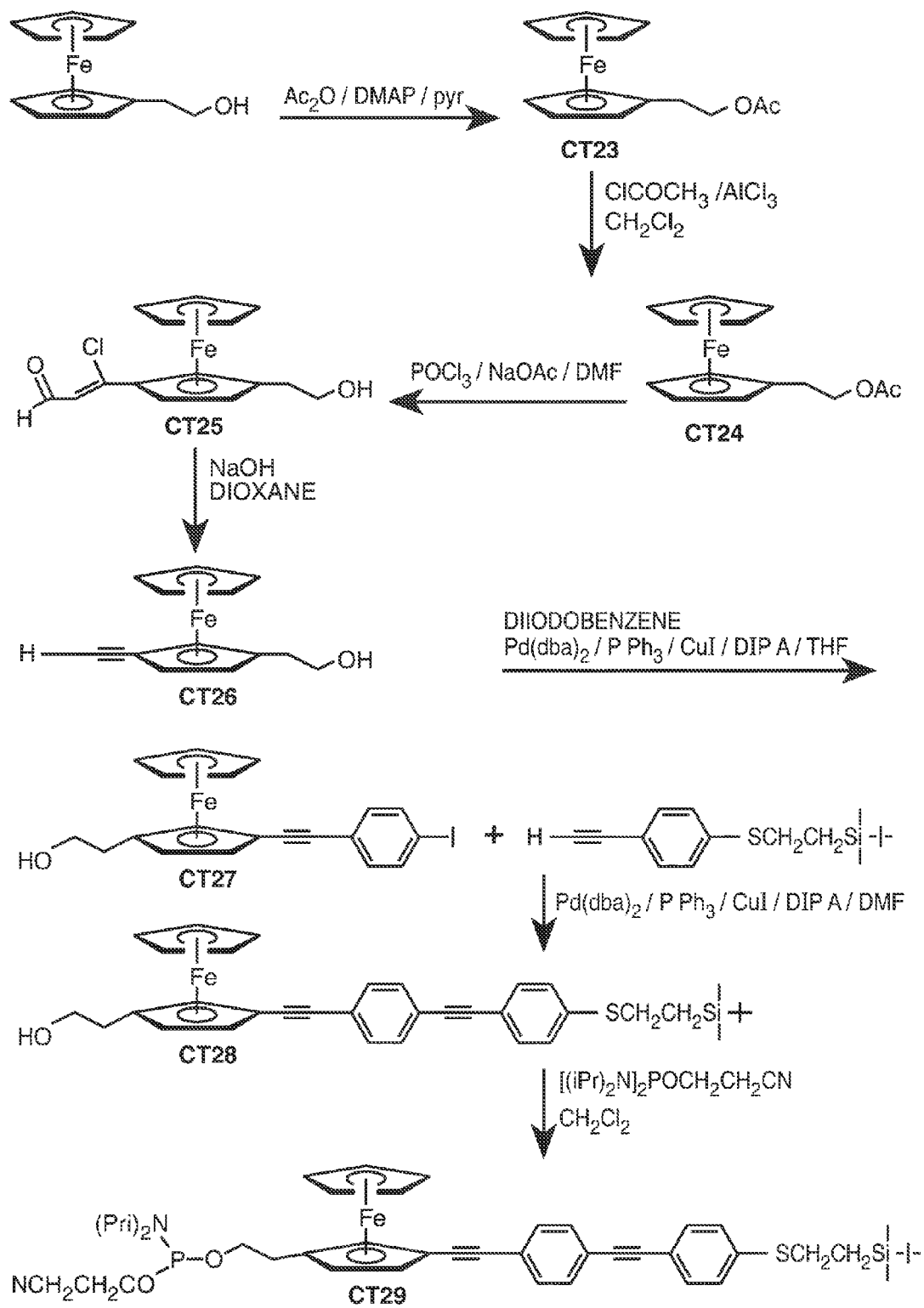
FIG._14

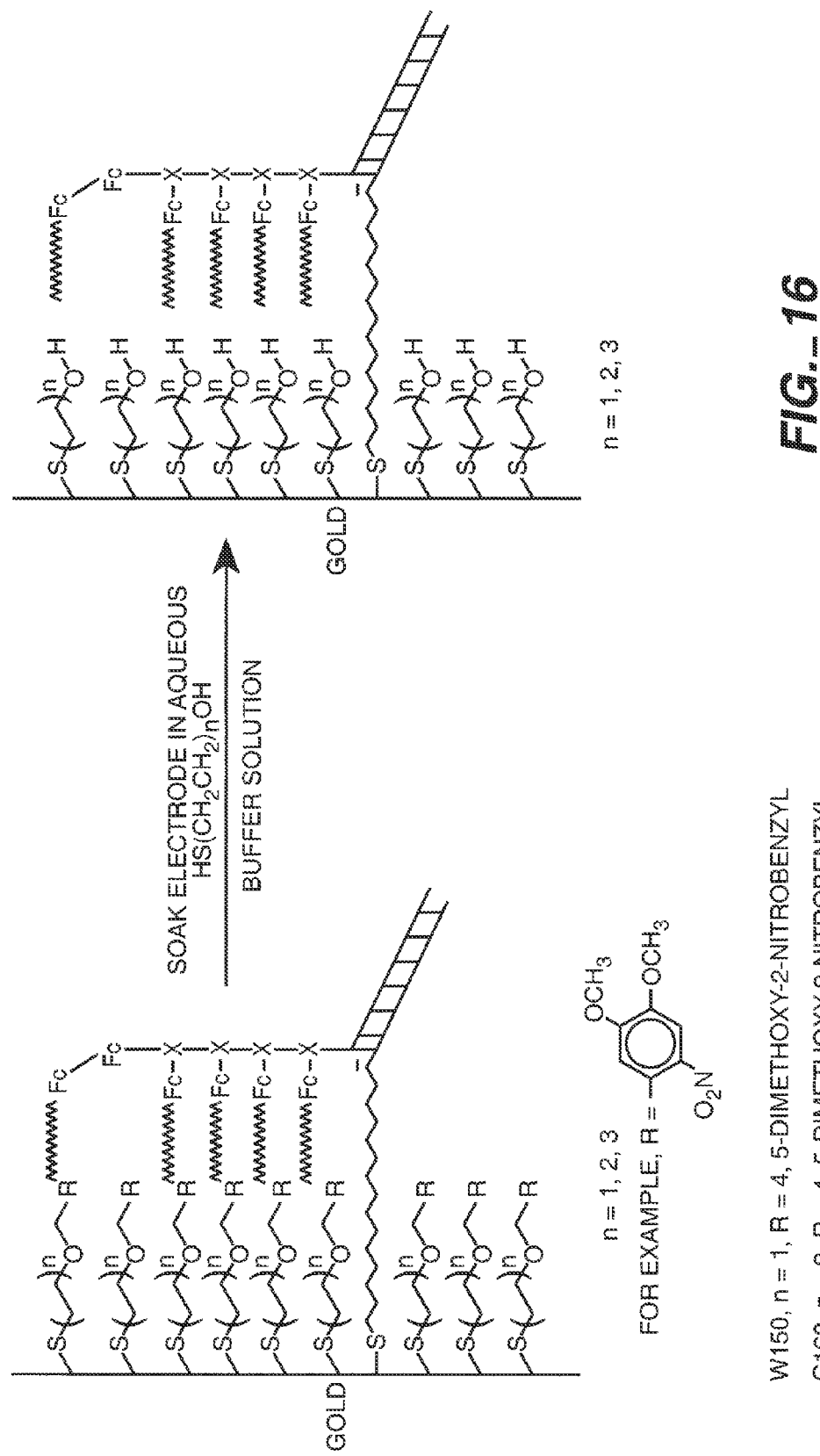
FIG._16

SEQUENCE DETERMINATION OF NUCLEIC ACIDS USING ELECTRONIC DETECTION

This is an application claiming the benefit of the filing date under 35 U.S.C. 119(e) of 60/145,695, filed Jul. 26, 1999, and 60/190,259, filed Mar. 17, 2000.

FIELD OF THE INVENTION

The present invention is directed to methods and compositions for the use of self-assembled monolayers to electronically detect nucleic acids, particularly alterations such as nucleotide substitutions (mismatches) and single nucleotide polymorphisms (SNPs).

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48-51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41-47 (1993)).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art.

There are a variety of particular techniques that are used to detect sequence, including mutations and SNPs. These include, but are not limited to, OLA (as well as a variation, rolling circle amplification), Invader™, single base extension methods, allelic PCR, and competitive probe analysis (e.g. competitive sequencing by hybridization; see below).

Oligonucleotide ligation amplification ("OLA", sometimes referred to herein as the ligation chain reaction (LCR)) involves the ligation of two smaller probes into a single long probe, using the target sequence as the template. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; WO 97/31256 and WO 89/09835, all of which are incorporated by reference.

A variation of OLA which can also be used for genotyping is termed "rolling circle amplification". Rolling circle amplification utilizes a single probe that hybridizes to a target such that upon ligation of the two termini of the probe, a circular probe is formed. A primer and a polymerase is added such that the primer sequence is extended. As the circular probe has no terminus, the polymerase repeatedly extends the circular probe resulting in concatamers of the circular probe. As such, the probe is amplified. Rolling-circle amplification is generally described in Baner et al. (1998) Nuc. Acids Res. 26:5073-5078; Barany, F. (1991) Proc. Natl. Acad. Sci. USA 88:189-193; Lizardi et al. (1998) Nat. Genet. 19:225-232; Zhang et al., Gene 211:277 (1998); and Daubendiek et al., Nature Biotech. 15:273 (1997); all of which are incorporated by reference in their entirety.

Invader™ technology is based on structure-specific nucleases that cleave nucleic acids in a site-specific manner. Two probes are used: an "invader" probe and a "signalling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

Single base extension methods can also be used for genotyping. Single base extension utilizes a polymerase and differentially labeled dNTPs; see WO 92/15712, EP 0 371 437 B1, EP 0317 074 B1; Pastinen et al., Genome Res. 7:606-614 (1997); Syvänen, Clinica Chimica Acta 226:225-236 (1994); and WO 91/13075).

An additional method is allelic PCR. As described in Newton et al., Nucl. Acid Res. 17:2503 (1989), hereby expressly incorporated by reference, allelic PCR allows single base discrimination based on the fact that the PCR reaction does not proceed well if the terminal 3'-nucleotide is mismatched, assuming the DNA polymerase being used lacks a 3'-exonuclease proofreading activity.

PCT applications WO 95/15971, PCT/US96/09769, PCT/US97/09739, PCT US99/01705, WO96/40712 and WO98/20162, all of which are expressly incorporated by reference, describe novel compositions comprising nucleic acids containing electron transfer moieties, including electrodes, which allow for novel detection methods of nucleic acid hybridization.

Accordingly, it is an object of the present invention to provide methods for determining the sequence of nucleic acids utilizing electrochemical detection.

SUMMARY OF THE INVENTION

In accordance with the above objects, the present invention provides compositions comprising a first nucleic acid comprising a first ETM with a first redox potential and a second nucleic acid comprising a second ETM with a second redox potential. The first and second redox potentials are different. The sequences of the nucleic acids can be the same or different, and in a preferred embodiment, they differ by only one base. The compositions may further comprise additional nucleic acids, also with unique redox potentials.

In an additional aspect, the present invention comprises compositions comprising a substrate with a plurality of array locations, each array location comprising a covalently attached capture probe, and a plurality of competimers. Each competimer hybridizes to either (1) a capture probe; (2) a first portion of a capture extender probe; or (3) a first portion of a label probe. The array locations may comprise electrodes.

In a further aspect, the present invention provides methods of detecting the presence of a target sequence in a sample comprising providing an array comprising a plurality of capture probes covalently attached to a solid support. The array is contacted with the sample under conditions wherein at least one assay complex comprising a target sequence, a capture probe and a detectable label is formed. The array is contacted with a plurality of competimers, and the presence or absence of the detectable label is detected as an indication of the presence or absence of said target sequence. The competimers can be added with the sample or after the formation of the assay complex.

In an additional aspect, the invention provides methods for detecting the presence of a target sequence comprising providing an assay complex comprising a target sequence and a capture probe covalently attached to an electrode, wherein the assay complex comprises at least one ETM, and detecting the presence or absence of the ETM at least two different temperatures.

In a further aspect, the present invention provides methods for determining the identification of a nucleotide at a detection position in a target sequence comprising adding a target sequence to an array comprising a plurality of array locations, each array location comprising a capture probe differing by at least a single nucleotide at the position that will hybridize to the detection position of the target, such that at least one assay complex comprising said target sequence, said capture probe, and a covalently attached ETM is formed. The presence or absence of the ETM is determined at least two different temperatures.

In an additional aspect, the present invention provides methods for determining the identification of a nucleotide at a detection position in a target sequence. The target sequence comprises, 5' to 3', a first target domain comprising an overlap domain comprising at least a nucleotide in the detection position, and a second target domain contiguous with the detection position. The methods comprise hybridizing a first probe to the first target domain, and hybridizing a second probe to the second target domain, wherein the second probe comprises a detection sequence that does not hybridize with the target sequence. If the second probe comprises a base that is perfectly complementary to the detection position, a cleavage structure is formed. A cleavage enzyme is provided that will cleave the cleavage structure, releasing the detection sequence, and an assay complex is formed comprising the detection sequence, a capture probe covalently attached to an electrode, and at least one ETM. The presence or absence of the ETM is detected as an indication of the formation of the cleavage structure. The base at the detection position can then be identified.

In a further aspect, the methods of the invention provide for determining the identification of a nucleotide at a detection position in a target sequence. The target sequence comprises a first target domain comprising the detection position and a second target domain adjacent to the detection position. The methods comprise hybridizing a first ligation probe to the first target domain, and hybridizing a second ligation probe to the second target domain, wherein if the second ligation probe comprises a base that is perfectly complementary to the detection position a ligation structure is formed. A ligation enzyme is provided that will ligate the first and the second ligation probes to form a ligated probe. An assay complex is formed with the ligated probe, a capture probe covalently attached to an electrode, and at least one ETM, and the presence or absence of the ETM is detected as an indication of the formation of the ligation structure. The base at the detection position can then be identified.

In an additional aspect, the methods are directed to methods of determining the identification of a nucleotide at a detection position in a target sequence. The target sequence comprises a first target domain directly 5' adjacent to the detection position. The method comprises providing an assay complex comprising the target sequence, a capture probe covalently attached to an electrode, and an extension primer hybridized to the first target domain of the target sequence. A polymerase enzyme and a plurality of dNTPs each comprising a covalently attached ETM with a unique redox potential are provided, under conditions whereby if one of the dNTPs basepairs with the base at the detection position, the extension primer is extended by the enzyme to incorporate a dNTP comprising an ETM, which is then detected to determine the identity of the base at the detection position.

In a further aspect, the invention provides surfaces comprising a self-assembled monolayer (SAM) comprising at least one photocleavable species.

In an additional aspect, the invention provides surfaces comprising a SAM comprising a first species comprising insulators and a second species comprising a electroconduit forming species (EFS).

In a further aspect, the invention provides methods of detecting the presence of a target analyte in a sample comprising adding the target analyte to an electrode comprising a first SAM forming species comprising a capture binding ligand and at least a second SAM forming species, to form a hybridization complex comprising the target analyte and the capture binding ligand. Then, a third SAM forming species is added that replaces the second SAM forming species. The method further comprises forming an assay complex comprising the target analyte, the capture binding ligand, and at least one electron transfer moiety (ETM) and detecting the presence or absence of the ETM as an indication of the presence or absence of the target analyte.

In an additional aspect, the invention provides methods of detecting a target analyte in a sample comprising binding a target analyte to an electrode comprising a covalently attached capture binding ligand and binding a solution binding ligand to the target analyte, wherein the solution binding ligand comprises a first portion that will bind to a target analyte and a directly or indirectly attached recruitment linker comprising a first portion comprising at least one conductive oligomer comprising at least one ETM. The presence of the ETM is detected using said electrode as an indication of the presence of the target analyte.

In a further aspect, the invention provides methods of adding at least one ETM to a nucleic acid comprising providing a nucleic acid comprising a first functional group, providing at least one ETM with a second functional group, and joining the first and the second functional groups to form a covalent attachment.

BRIEF DESCRIPTION OF THE DRAWINGS

FIGS. 1A-1R depict a number of different compositions of the invention; the results are shown in Example 1 and 2 of PCT US99/01703, hereby expressly incorporated by reference. FIG. 1A depicts I, also referred to as P290. FIG. 1B depicts II, also referred to as P291. FIG. 1C depicts III, also referred to as W31. FIG. 1D depicts IV, also referred to as N6. FIG. 1E depicts V, also referred to as P292. FIG. 1F depicts II, also referred to as C23. FIG. 1G depicts VII, also referred to as C15. FIG. 1H depicts VIII, also referred to as C95. FIG. 1I depicts Y63. FIG. 1J depicts another compound of the invention. FIG. 1K depicts N11. FIG. 1L depicts C131, with a phosphoramidite group and a DMT protecting group. FIG. 1M depicts W38, also with a phosphoramidite group and a DMT protecting group. FIG. 1N depicts the commercially available moiety that enables "branching" to occur, as its incorporation into a growing oligonucleotide chain results in addition at both the DMT protected oxygens. FIG. 1O depicts glen, also with a phosphoramidite group and a DMT protecting group, that serves as a non-nucleic acid linker. FIGS. 1A to 1G and 1J are shown without the phosphoramidite and protecting groups (i.e. DMT) that are readily added.

FIGS. 2A, 2B, 2C and 2D depict several preferred embodiments for mismatch detection using temperature. FIG. 2 depicts the use of an electrode 105 with a self-assembled monolayer 15 comprising passivation agents and a capture probe 20 attached via an attachment linker 10. The capture probe 20 has an interrogation position 25 that may comprise a mismatch with the detection position on the target sequence 120. FIG. 2A depicts the target sequence 120 comprising the ETMs 135; FIG. 2B depicts the use of a label probe 40 with the ETMs 135. As will be appreciated by those in the art, amplification probes, label extender probes, etc. can also be used. FIG. 2C utilizes a label probe 40 with the detection position 25. Again, amplification probes, label extender probes, etc. can also be used. FIG. 2D utilizes a capture extender probe 45 comprising the interrogation position 25.

FIGS. 3A and 3B depict two embodiments of the "competimer" invention. In FIG. 3A, the use of a competimer to determine perfect matches is shown. A substrate 1 with two electrodes 105 is shown; to the first is bound a capture probe comprising interrogation position 25 that does not match the detection position 121 of the target 120. The other capture probe has an interrogation position 25 that does perfectly match the detection position of the target. In the absence of the competimer, the target sequence:imperfect capture probe is stable enough to exist. However, in the presence of the competimer 50, the target is driven off the imperfect match in favor of competimer binding. In FIG. 3B, the target sequence 120 comprising the detection position 121 is hybridized to a capture extender probe 45 with interrogation position 25, which does not perfectly match the detection position. The capture extender probe 45 is hybridized to the capture probe 20 attached via an attachment linker 10. The addition of competimer 50 with interrogation position 25 that now does perfectly match the interrogation position 25 drives off the imperfectly bound target with its bound label probe 145. FIG. 3C is similar to 3B, except that the detection position is within the label probe recognition sequence.

FIG. 4 depicts the Tm curve results from Example 2.

FIG. 5 depicts some results from Example 4. After mixed (wild-type and mutant) oligo is placing the wild type oligo buffer, the mismatched hybridization (filled circle) is replaced by perfect matched hybridization (open circle).

FIG. 6 depicts some results from Example 5.

FIG. 7 depicts a nested set of primers for a PCR/APCR reaction.

FIGS. 8A, 8B and 8C depict some useful disulfide embodiments. FIG. 8A depicts a general class, FIG. 8B depicts two embodiments that were used to generate the data shown in FIG. 8C.

FIGS. 9A, 9B, 9C, 9D, 9E, 9F and 9G depict the synthesis of some disulfide embodiments. FIG. 9A depicts the general synthesis; with R, R' and R" being C1 to C20 alkyl or aromatic derivatives and B being any base such as HaOH, KOH, LiOH or MOR, with M being a metal. FIG. 9B shows the synthesis of H-phosphonate, FIGS. 9C and 9D show the synthesis of the CPG derivative, and FIG. 9E shows the synthesis of the insulator. 9F and 9G depict some cyclic disulfide embodiments.

FIG. 10 depicts the "cufflink" configuration.

FIG. 11B depicts a preferred embodiment.

FIGS. 12A and 12B depict a post-synthesis addition of detectable labels, in this case ETMs, to nucleic acids.

FIGS. 13A and 13B depict the use of labeling moieties comprising ETMs and a conductive oligomer, for association with or attachment to the electrode. These embodiments utilize thiols for attachment, although as will be appreciated by those in the art, the moiety will depend on the surface. R can be hydrogen or a protecting group.

FIG. 14 depicts a synthetic scheme for the labeling moieties of FIG. 13.

FIG. 16 depicts the displacement reaction for replacing one SAM with another.

DETAILED DESCRIPTION OF THE INVENTION

Figure 11A:
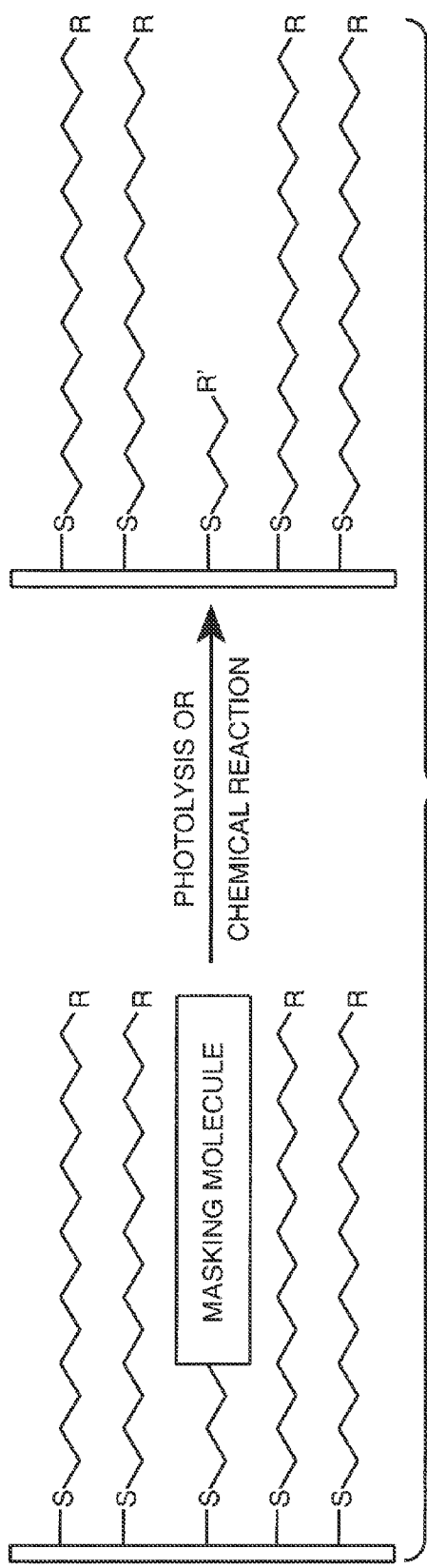
FIGS. 11A and 11B depict a schematic representation of the formation of electroconduits using cleavable species, including photocleavable and chemically cleavable.

The present invention is directed to methods of determining the sequence of a target nucleic acid at a particular position, using electrochemical detection on an electrode. The invention preferably includes the detection (and optionally quantification) of differences or variations of sequences (e.g. SNPs) using electrode arrays for detection of the variation.

As is known in the art, there are a number of techniques that can be used to detect or determine the identity of a base at a particular location in a target nucleic acid, including, but not limited to, the use of temperature, competitive hybridization of perfect and imperfect probes to the target sequence, sequencing by synthesis, for example using single base extension techniques (sometimes referred to as "minisequencing"), the oligonucleotide ligase amplification (OLA) reaction, rolling circle amplification (RCA), allelic PCR, competitive hybridization and Invader™ technologies. In addition, the present invention is directed to a novel invention that capitalizes on novel properties of surface-bound arrays, and uses "competimers" to reduce non-specific binding.

All of these techniques rely on the formation of assay complexes on a surface, frequently an electrode, as a result of hybridization of a target sequence (either the target sequence of the sample or a sequence generated in the assay) to a capture probe on the surface. As is more fully outlined herein, this may be direct or indirect (e.g. through the use of sandwich type systems) hybridization. The assay complex further comprises at least one electron transfer moiety (ETM), that is also either directly or indirectly attached to the target. Once the assay complexes are formed, the presence or absence of the ETMs are detected as is described below and in U.S. Pat. Nos. 5,591,578; 5,824,473; 5,770,369; 5,705,348 and 5,780,234; U.S. Ser. Nos. 08/911,589; 09/135,183; 09/306,653; 09/134,058; 09/295,691; 09/238,351; 09/245,105 and 09/338,726; and PCT applications WO98/20162; WO 00/16089; PCT US99/01705; PCT US99/01703; PCT US00/10903 and PCT US99/10104, all of which are expressly incorporated herein by reference in their entirety.

Many of these methods require a primer nucleic acid (which may include the ETM labels as well as the use of nucleic acid analogs) that is hybridized to the target sequence to form a hybridization complex, and an enzyme is added that in some way modifies the primer to form a modified primer; generally, the occurrence of the modification depends on the presence or absence of a particular sequence, thus allowing sequence differentiation. For example, OLA requires two primers that hybridize (either directly adjacently or separated by one or more bases) to the target sequence and a ligase; Invader™ requires two primers and a cleavage enzyme; etc. Thus, in general, a target nucleic acid is added to a reaction mixture that comprises the necessary amplification components, and a modified primer is formed, which is then either detected as an indication that the variation is present or not, or queried to determine the identity of the base at the position of interest.

In general, the modified primer is incorporated into an assay complex that comprises a label, such as an electron transfer moiety (ETM), which is either incorporated by an enzyme, present on the original primer, or added via a label probe. As required, the unreacted primers can be removed in a variety of ways, as will be appreciated by those in the art, although in many embodiments this is not required. The hybridization complex is then optionally disassociated, and the modified primer is added to an electrode as is generally described herein and in the cited applications. Usually, the electrodes comprise capture probes that will hybridize to the modified primers although as outlined herein, a variety of configurations, including sandwich assays, can be used. Detection proceeds via detection of the ETM label as an indication of the presence, absence or amount of the target sequence.

The methods of the invention find particular use in genotyping assays, i.e. the detection of particular nucleotides at specific positions, although as will be appreciated by those in the art, amplification and/or quantification need not necessarily occur to do genotyping.

Accordingly, the present invention provides compositions and methods for detecting the presence or absence of target nucleic acid sequences in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.; As will be appreciated by those in the art, virtually any experimental manipulation may have been done on the sample.

The present invention provides compositions and methods for detecting the presence or absence of target nucleic acid sequences in a sample. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or ETM attachment, an analog structure may be used. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The compositions and methods of the invention are directed to the detection of target sequences. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of a reaction such as a detection sequence from an Invader™ reaction, a ligated probe from an OLA reaction, an extended probe from an SBE reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe or a portion of capture extender probe, a second target domain may hybridize to a portion of an amplifier probe, a label probe, or a different capture or capture extender probe, etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

As is more fully outlined below, the target sequence comprises a position for which sequence information is desired, generally referred to herein as the "detection position". In a preferred embodiment, the detection position is a single nucleotide, although in some embodiments, it may comprise a plurality of nucleotides, either contiguous with each other or separated by one or more nucleotides. By "plurality" as used herein is meant at least two. As used herein, the base which basepairs with the detection position base in a hybrid is termed the "interrogation position".

In a preferred embodiment, the methods of the invention are used to detect pathogens such as bacteria. In this embodiment, preferred target sequences include rRNA, as is generally described in U.S. Pat. Nos. 4,851,330; 5,288,611; 5,723,597; 6,641,632; 5,738,987; 5,830,654; 5,763,163; 5,738,989; 5,738,988; 5,723,597; 5,714,324; 5,582,975; 5,747,252; 5,567,587; 5,558,990; 5,622,827; 5,514,551; 5,501,951; 5,656,427; 5,352,579; 5,683,870; 5,374,718; 5,292,874; 5,780,219; 5,030,557; and 5,541,308, all of which are expressly incorporated by reference.

If required, the target sequence is prepared using known techniques. For example, the sample may be treated to lyse the cells, using known lysis buffers, electroporation, etc., with purification and/or amplification as needed, as will be appreciated by those in the art. Suitable amplification techniques are outlined in PCT US99/01705, hereby expressly incorporated by reference. In addition, techniques to increase the amount or rate of hybridization can also be used; see for example WO 99/67425, hereby incorporated by reference.

In general, current SNP detection methods utilize a first amplification step such as PCR to amplify the patient's nucleic acids. In a preferred embodiment, a step in the methods of the invention include a step to produce an excess of one strand over the other. As will be appreciated by those in the art, a variety of methods can be used, including, but not limited to, asymmetric polymerase chain reaction (APCR), an exonuclease method and the capture of the non-target strand.

In a preferred embodiment, asymmetric polymerase chain reaction (APCR) is used to enhance the production of the single stranded nucleic acid fragment used as the target sequence for detection as outlined herein. Traditional APCR techniques produces a single stranded bias by using the primers in a ratio of 5 to 1, although a variety of ratios ranging from 2:1 to 100:1 can be used as well.

In a preferred embodiment, a novel nested primer method is used to amplify the patient sample. In this embodiment, an enhancement of target production is achieved using a two step process: a first symmetric PCR step, using a 1:1 ratio of primers, followed by the addition (preferably to the same reaction) of a second APCR step, using a ratio of 50:1 (again, with ratios of from about 2:1 to over 100:1 being useful). Alternatively, these reactions may be done in two steps as well. This has been shown to result in a 3-6 fold increase over a one step APCR reaction.

In a preferred embodiment, the asymmetric amplification step is accomplished using an exonuclease that can selectively degrade one strand. For example, Lambda exonuclease is a 5' to 3' exonuclease that selectively digests the phosphorylated strand of double stranded DNA. This strand can be generated during amplification when one of the primers comprises a 5' terminal phosphate group. Incorporation of this phosphorylated primer into the amplicon allows lambda exonuclease to digest specifically one strand, leaving single stranded nucleic acid as the product. As will be appreciated by those in the art, the amplification reaction can be any reaction that utilizes a 5' terminal phosphate group; a variety of these techniques are described in WO 99/37819, hereby incorporated by reference. Preferred embodiments utilize PCR as the reaction.

In a preferred embodiment, PCR is done using a primer with a capture tag to allow the removal of one strand. For example, by using a biotin-labeled primer in the PCR (or other amplification method) reaction, followed by the use of a separation step, for example the addition of streptavidin beads to the reaction mixture at an elevated temperature, single-stranded nucleic acid is made. As is known in the art, any number of binding pairs can be used, including antigens and antibodies; see for example the list in WO 98/12430, hereby incorporated by reference.

Accordingly, the compositions and methods of the present invention are used to identify the nucleotide(s) at a detection position within the target sequence.

In a preferred embodiment, variations in temperature are used to determine either the identity of the nucleotide(s) at the detection position or the presence of a mismatch. As a preliminary matter, the use of temperature to determine the presence or absence of mismatches in double stranded hybrids comprising a single stranded target sequence and a probe is well known. As is known in the art, differences in the number of hydrogen bonds as a function of basepairing between perfect matches and mismatches can be exploited as a result of their different Tms (the temperature at which 50% of the hybrid is denatured). Accordingly, a hybrid comprising perfect complementarity will melt at a higher temperature than one comprising at least one mismatch, all other parameters being equal. (It should be noted that for the purposes of the discussion herein, all other parameters (i.e. length of the hybrid, nature of the backbone (i.e. naturally occurring or nucleic acid analog), the assay solution composition and the composition of the bases, including G-C content are kept constant). However, as will be appreciated by those in the art, these factors may be varied as well, and then taken into account.)

It should be noted in this context that "mismatch" is a relative term and meant to indicate a difference in the identity of a base at a particular position, termed the "detection position" herein, between two sequences. In general, sequences that differ from wild type sequences are referred to as mismatches. However, particularly in the case of SNPs, what constitutes "wild type" may be difficult to determine as multiple alleles can be relatively frequently observed in the population, and thus "mismatch" in this context requires the artificial adoption of one sequence as a standard. Thus, for the purposes of this invention, sequences are referred to herein as "perfect match" and "mismatch".

The methods and compositions of the invention have a particular utility in that repeated assays (i.e. initiation and electrochemical detection of the ETMs of the assay complexes) may be done on a single surface or array. That is, detection systems relying on fluorescence frequently are limited in the number of times an assay complex can be detected, as photobleaching of the fluors used for the detection becomes a problem. Generally only a single assay is run on an assay complex. Thus, when mismatch detection using temperature is done, several different assays (i.e. different chips) must be run to generate a temperature curve. This has the disadvantage of chip-to-chip or assay-to-assay variability. In addition, fluorescent labels also give signals when they are not bound to the surface; thus a wash step is required. However, the compositions of the present invention allow repeated detection; in fact, as outlined below, when AC systems are used, the assay complex may be assayed hundreds or thousands of times to take a single data point; thus, a single assay complex may be assayed a number of times, including at a plurality of temperatures. This allows the generation of hybridization kinetics curves, for example to generate a temperature curve on a single assay complex, thus allowing mismatch detection. In addition, the present invention allows measurements at multiple temperatures, and therefore all the Tm's on an array can be different. This is in contrast to fluorescent labels, where all the Tms in an array must be closely matched.

Thus, in a preferred embodiment, the invention provides methods of generating hybridization kinetics curves in an assay for the presence of a target sequence in a sample. By "hybridization kinetics curve" herein is generally meant a plot of percentage hybridization of a two nucleic acids versus time or temperature, although as will be appreciated by those in the art, other properties may be plotted to generate a kinetics curve. What is important is that the present invention allows multiple data points to be collected from a single array, under a wide variety of conditions, thus allowing the generation of additional information about a sample. These methods comprise contacting the sample with an array with capture probes as outlined herein. At least one hybridization complex is formed, comprising at least the target and the capture probe. The hybridization complex further comprises a label, such as an ETM; this can be accomplished in a variety of ways as outlined herein, including the use of a label probe, or the incorporation of the label into the target itself. Thus an assay complex is formed. The detection of the label (i.e. the presence of the target sequence) is done a number of times; that is, a plurality of measurements are made. In a preferred embodiment, the method does not remove labels that are not part of the complex between each measurement. This can be done at a variety of different experimental conditions; for example, the measurements may be done at different temperatures, different reagent or buffer concentrations (e.g. increasing stringency conditions), etc.

As will be appreciated by those in the art, mismatch detection using temperature may proceed in a variety of ways.

In a preferred embodiment, a temperature gradient is run using a single type of probe, to be contrasted with the use of a plurality of probes that are labeled with different detectable labels, as described below.

That is, as is shown in FIG. 2, a hybrid between a target sequence and a secondary probe that may contain a mismatch at the detection position is formed. As is outlined in the Figure, the secondary probe may be a capture probe (FIGS. 2A and 2B), a capture extender probe (2D) or a label probe (2C). In general, systems that release the target from the surface as a result of mismatch (2A, 2B and 2D) are preferred as the background (e.g. non-specific binding) may decrease.

Generally, the assay complexes are formed at a Tm below the Tm of a mismatch:target hybrid. The temperature is slowly raised, and data points taken at a plurality of temperatures (or, as outlined herein, at a plurality of different conditions). By "plurality" as used herein is meant at least two. In this context, preferred pluralities include 2, 3, 4, 5, 6, 7, 8, 9 or 10 or more different temperatures. Preferred increments are 5° C., with 25° C., 30° C., 35° C., 40° C., 45° C., 50° C., 55° C. and 60° C. all being preferred. In some embodiments, lower temperatures can also be used, such as 10° C., 15° C. and 15° C. In a preferred embodiment, the temperatures span the Tm of the hybrid in question, although this may not be required in some instances. Thus, for example, if a mismatch melts at 45° C. and a perfect match melts at 55° C., running the assays at 40 or 45° and 50° can distinguish between the mismatch and the match.

In addition, as will be appreciated by those in the art, it is also possible to run a single experiment above the Tm of the mismatch. That is, the formation of an assay complex, as detected by the presence or absence of the ETMs in an assay complex as is more fully outlined below, above the Tm of the mismatch indicates that the probe comprises perfect complementarity at the detection position. In a preferred embodiment, a plurality of probes are used to identify the base at the detection position. In this embodiment, each different probe comprises a different detection label and a different base at the position that will hybridize to the detection position of the target sequence (herein referred to as the interrogation position) such that differential hybridization will occur. In this embodiment, the assays may be run either isothermally or as a function of temperature, as is generally outlined above. That is, since all other parameters being equal, a perfectly complementary probe will be more stable and presumably have a slower off rate than a probe comprising a mismatch at any particular temperature. Accordingly, by using different probes, each with a different base at the interrogation position and each with a different label, the identification of the base at the detection position is elucidated. These differences can be amplified by using different temperatures.

Alternatively, as will be appreciated by those in the art, the same result can be accomplished a single ETM label and 4 different electrode pads. In this embodiment, each pad comprises a capture probe with a different base at the interrogation position. Using either alterations in temperature or competimers (as described below), the identification of the base at the detection position can be done.

Thus, in a preferred embodiment, the invention provides a plurality of probes each with at least one ETM with a unique redox potential. This is analogous to the "two color" or "four color" idea of competitive hybridization, and is also analogous to sequencing by hybridization. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

As is more fully outlined below, a variety of ETMs find use in the invention. In this embodiment, the redox potentials of the different ETMs are chosen such that they are distinguishable in the assay system used. By "redox potential" (sometimes referred to as $E_O$) herein is meant the voltage which must be applied to an electrode (relative to a standard reference electrode such as a normal hydrogen electrode) such that the ratio of oxidized and reduced ETMs is one in the solution near the electrode. In a preferred embodiment, the redox potentials are separated by at least 100 mV, although differences either less than this or greater than this may also be used, depending on the sensitivity of the system, the electrochemical measuring technique used and the number of different labels used. In a particularly preferred embodiment, derivatives of ferrocene are used; for example, ETMs may be used comprising ferrocene without ring substituents or with the addition of an amine or an amide, a carboxylate, etc.

In a preferred embodiment, each probe of the probe set has a different base at the interrogation position and a different covalently attached ETM. Thus, sets of two probes (for example, when a SNP may exist as one of two different bases), three probes (when an allele comprises 3 different bases) or four probes (to determine the identity of the base at the detection position) can be used. By adding the set of probes to the target sequence and detecting which ETM is present, the identity of the base at the detection position is determined.

In a preferred embodiment, all of the other positions of the probes used in this embodiment are the same; that is, in some embodiments it is preferable to use probes that have all other components equal (e.g. both the length of the probes as well as the non-interrogation bases) to allow good discrimination. This is particularly preferred for SNP discovery. In other embodiments, it may be desirable to alter other components, in order to maximize discrimination at the detection position. In techniques relying on the competitive hybridization of perfect match probes and mismatch probes, a variety of unique techniques may be used to maximize the discrimination of the probes by incorporating certain features into the probes.

As a preliminary matter, the strand that gives the most favorable difference for Tm differences should be chosen; G/T is chosen over C/A and G/A over C/T mismatches, for example. Similarly, preferred embodiments generally utilize probes that have the interrogation base in the middle of the probe, rather than towards one of the ends. However, as outlined herein, the shifting of the interrogation position within the probe can be used to maximize discrimination in some embodiments.

For example, in a preferred embodiment, the perfect match/mismatch discrimination of the probes may be enhanced by changing the binding affinities of bases at and near the mismatch position. For example, sequences that have G-C pairs adjacent to the detection position (or within 3 bases) can hinder good discrimination of match/mismatch. By choosing substitutions in these areas, better discrimination is achieved. For example, this may be done to either destabilize the base pairing in the detection position, or preferably to stabilize the base pairing in the detection position while destabilizing the base pairs in the positions adjacent to the detection position. Base substitutions reduce the number of hydrogen bonds to only two or less hydrogen bonds per base pair without disturbing the stacking structure of the double strand in the area. The amount of destabilization will depend on the chemical nature of the substitution, the number of substitutions and the position of the substitutions relative to the detection position. The local strand destabilization has to be balanced against the loss of specificity of the probe. These substitutions can be either naturally occurring or synthetic base analogs.

For example, base analogs that enhance the strength of base pairing include isodeoxyguanosine (isodG), which pairs with C, and 5-methy isodeoxycytidine (5-Me-isodC) which pairs with G.

Similarly, base analogs that can frequently destabilize base pairing are known. These generally fall into three categories. Degenerate bases such as 2'-deoxyinosine and 2'-deoxynebularine exhibit low, unequal hydrogen bonding to all for bases. Other degenerate bases base pair with only subsets of bases: 6H, 8H-3,4-dihydropyrimido[4,5-c][1,2]oxazin-7-one (dP), base pairs with purines only, and 2-amino-6-methoxyamino purine (dK) base pairs with pyrimidines only. Alternatively, there are some universal bases such as 3-nitropyrrole and 5-nitrondole and exhibit low unequal hydrogen boding to all for bases. In addition, mismatched bases (either naturally occurring or analogs) can also be used, as long as it is not too destabilizing.

As will be appreciated by those in the art, these base analogs may be incorporated into either the probes, or, when an amplification step of the target sequence is utilized, into the target and/or the probes.

In a preferred embodiment, the interrogation base is changed to a base analog. In some embodiments, the most difficult mismatch to discriminate is a G:T or G:U mismatch, as the Tm decrease is the smallest; G:T and G:U pairs still have two potential hydrogen bonds. Thus, when for example the SNP of interest involves a G/A difference, it can be difficult to distinguish between these. In order to enhance the destabilization of the G:T or G:U mismatch, alternative bases can be used. For example, 2-thiothymidine or 2-thiouridine have been reported to hybridize to A better than to T or U putatively because the 2-thio groups do not participate hydrogen bond. See for example Connolly et al., Nucleic Acid Res. 17:4957 (1989); Ishikawa et al., Bioorg. & Med. Chem. Lett. 1:523 (1991); Kuimelis et al., Nucleic Acid Res. 22:1429 (1991), all of which are expressly incorporated herein by reference. Thus, the introduction of these thiolated bases can stabilize A:T or A:dU pairs and destabilize G:T or G:U mismatches.

Furthermore, in a preferred embodiment, the discrimination of the interrogation probes can be altered by altering the length of the probes. For example, as noted above, certain mismatches, such as G/A differences, can be difficult due to the stability of G:T mispairings. By decreasing the standard probe length from 15-25 basepairs to 10-15 basepairs, increased discrimination may be done.

In addition, good probe design may also allow enhanced discrimination at the detection position. For example, as outlined above, G-T mismatches can be the most difficult to evaluate; thus, in situations where a G-T mismatch must be evaluated, shorter probes can be used.

Similarly, mismatch detection using the present invention may be maximized in sandwich assay formats that rely on assay complexes comprising a target, a capture probe and a label probe. In this embodiment, better discrimination is seen when the capture probe and the label probe hybridize to the target at domains separated by at least 2 or more bases. Discrimination may be further maximized by designing the system such that the Tm of the label probe is only slightly greater than that of the capture probe.

In addition, additional discrimination of the system can be accomplished through the choice of the ETM associated with each probe. That is, in any given SAM system, some of the ETMs associate with the SAM better than others. Therefore, when additional discrimination is needed, the choice of the ETM on each probe can help. For example, in some monolayers comprising insulators (M44) and conductive oligomers (H6), the W97 molecule depicted herein is somewhat less stable than N6 over the monolayer, and this fact can be exploited.

Similarly, the length of the probes can help the discrimination; generally probes of 15-20 are used, with 17mers being particularly preferred for room temperature genotyping.

In addition, the use of multiple potential ETMs allows for gene expression monitoring in systems that compare two or more samples. In this embodiment, a specific selection of nucleic acids derived from two or more distinct sources are detected (preferably quantitatively) and compared between the sources with respect to the abundance of individual nucleic acids. In a preferred embodiment, nucleic acid (particularly mRNA) from anis y number of organisms or cell lines can be examined; for example, cells from disease states (e.g. cancerous cells) may be compared with normal cells. Similarly, the effects of drugs, drug candidates, other compounds or different experimental conditions can be assessed: cells in the presence and absence of the compound or under different conditions (changes in temperature, pH, etc.) can be compared. Alternatively, different biological samples from different locations or times can be compared: for example, water, soil, air, clinical, tissue or forensic samples can be compared.

In this embodiment, a first sample is labeled with ETMs with a first redox potential and a second sample is labeled with ETMs with a second redox potential. As described herein, this labeling may be done in several ways. For example, the primers used in an amplification step may comprise the ETMs. Alternatively, labeled nucleotides are used during the amplification. Alternatively, the use of primers comprising "tags" that will hybridize to label probes; different samples utilize different tags, and thus different signaling probes. The samples can be mixed and added to an array, analyzed in parallel, or in any number of assay formats as is known in the art.

In a preferred embodiment, the identification of the nucleotide at the detection position is done using enzymatic processes which rely on complementarity to proceed. That is, several processes which are used in amplification reactions (see for example PCT US99/01705, hereby incorporated by reference) such as Invader™ technology or OLA, rely on perfect complementarity for the reaction to proceed. By using probes that at the interrogation position either are perfectly complementary to the detection position or not, the identity of the base at the detection position may be determined.

In a preferred embodiment, the oligonucleotide ligation amplification (OLA) is used to determine the identity of the base at the detection position. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, and U.S. Ser. Nos. 60/078,102 and 60/073,011, all of which are incorporated by reference.

This method is based on the fact that certain ligation enzymes will ligate two probes together, if they are hybridized to a target strand and if perfect complementarity exists at the two bases being ligated together. Thus, in this embodiment, the target sequence comprises a contiguous first target domain comprising the detection position and a second target domain adjacent to the detection position. That is, the detection position is "between" the rest of the first target domain and the second target domain. A first ligation probe is hybridized to the first target domain and a second ligation probe is hybridized to the second target domain. If the first ligation probe has a base perfectly complementary to the detection position base, and the adjacent base on the second probe has perfect complementarity to its position, a ligation structure is formed such that a ligase enzyme will ligate the two probes together to form a ligated probe. If this complementarity does not exist, no ligation structure is formed and the ligase enzyme does not ligate the probes together to an appreciable degree. This may be done using heat cycling, to allow the ligated probe to be denatured off the target sequence such that it may serve as a template for further reactions.

The ligated probe is then detected as is generally outlined below. As will be appreciated by those in the art, this may occur in a variety of ways. In a preferred embodiment, one of the probes comprises at least one covalently attached ETM, and the other probe comprises a sequence that is used to hybridize either directly or indirectly (i.e. through the use of a capture extender probe) to a capture probe on an electrode. Thus, only if both components are present will a signal be generated; this can eliminate the need for removing unligated probes from the system. Alternatively, unligated probes can be removed or washed away, for example using a binding step, etc. For example, the capture probe can hybridize to the second ligation probe or to a first portion of a capture extender probe. The capture extender probe comprises a first portion that hybridizes to the capture probe and a second portion that hybridizes to the second ligation probe. Other variations will be appreciated by those in the art.

Alternatively, rather than have the probe directly labeled with an ETM, sandwich systems are used; for example, the probe comprises a sequence to which a label probe will bind. Other embodiments utilize amplifier probes, label extender probes, etc. as outlined below.

As will be appreciated by those in the art, the ligation reaction may be done in solution, generating a plurality of ligated probes. These then may be added to a detection electrode as outlined herein; again, preferred embodiments utilize the separation of the ETM label and the capture sequences on different probes. Thus, the unligated probes comprising the ETM will not be captured on the surface. Alternatively, the reaction may be done on a surface, with the capture of the target sequence and then the recruitment of the probe comprising the label (or a probe to which a label probe will bind) to the target sequence. Generally, this embodiment utilizes a thermal step to drive off unligated probes such that only the longer ligated probes will remain on the surface. Similarly, the capture probe itself can be used as a ligation probe, with its terminus comprising the detection position. Upon the addition of the target sequence and a second ligation probe, a ligation structure is formed. A label probe (or other probes) can be added as well. Again, this embodiment may require the use of a thermal step to ensure that the target sequence does not remain on the surface unless ligation has occurred.

As will be appreciated by those in the art, these techniques may be done for the two strands of a double-stranded target sequence. The target sequence is denatured, and two sets of probes are added: one set as outlined above for one strand of the target, and a separate set (i.e. third and fourth primer robe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

Again, as outlined above, the detection of the OLA reaction can occur directly, in the case where one or both of the primers comprises at least one ETM, or indirectly, using sandwich assays, through the use of additional probes; that is, the ligated probes can serve as target sequences, and detection may utilize amplification probes, capture probes, capture extender probes, label probes, and label extender probes, etc.

In a preferred embodiment the signal amplification technique is RCA. Rolling-circle amplification is generally described in Baner et al. (1998) *Nuc. Acids Res.* 26:5073-5078; Barany, F. (1991) *Proc. Natl. Acad. Sci. USA* 88:189-193; Lizardi et al. (1998) *Nat. Genet.* 19:225-232; Zhang et al., Gene 211:277 (1998); and Daubendiek et al., Nature Biotech. 15:273 (1997); all of which are incorporated by reference in their entirety.

In general, RCA may be described as follows. First, as is outlined in more detail below, a single RCA probe is hybridized with a target nucleic acid. Each terminus of the probe hybridizes adjacently on the target nucleic acid (or alternatively, there are intervening nucleotides that can be "filled in" using a polymerase and dNTPs, as outlined herein) and the OLA assay as described above occurs. That is, only if a perfect complementarity exists will the ligation occur. When ligated, the probe is thus circularized while hybridized to the target nucleic acid. Addition of a primer, a polymerase and dNTPs results in extension of the circular probe. However, since the probe has no terminus, the polymerase continues to extend the probe repeatedly. Thus results in amplification of the circular probe. This very large concatemer can be detected intact, as described below, or can be cleaved in a variety of ways to form smaller amplicons for detection as outlined herein.

Accordingly, in an preferred embodiment, a single oligonucleotide is used both for OLA and as the circular template for RCA (referred to herein as a "padlock probe" or a "RCA probe" (RCP)). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent (either directly or indirectly, as outlined herein) to the first domain. Hybridization of the probe to the target nucleic acid results in the formation of a hybridization complex. Ligation of the "primers" (which are the discrete ends of a single oligonucleotide, the RCA probe) results in the formation of a modified hybridization complex containing a circular probe i.e. an RCA template complex. That is, the oligonucleotide is circularized while still hybridized with the target nucleic acid. This serves as a circular template for RCA. Addition of a primer, a polymerase and the required dNTPs to the RCA template complex results in the formation of an amplified product nucleic acid. Following RCA, the amplified product nucleic acid is detected as outlined herein. This can be accomplished in a variety of ways; for example, the polymerase may incorporate labelled nucleotides; a labeled primer may be used, or alternatively, a label probe is used that is substantially complementary to a portion of the RCA probe and comprises at least one label is used.

Accordingly, the present invention provides RCA probes (sometimes referred to herein as "rolling circle probes (RCPs) or "padlock probes" (PPs)). The RCPs may comprise any number of elements, including a first and second ligation sequence, a cleavage site, a priming site, a capture sequence, nucleotide analogs, and a label sequence.

In a preferred embodiment, the RCP comprises first and second ligation sequences. As outlined above for OLA, the ligation sequences are substantially complementary to adjacent domains of the target sequence. The domains may be directly adjacent (i.e. with no intervening bases between the 3' end of the first and the 5' of the second) or indirectly adjacent, with from 1 to 100 or more bases in between.

In a preferred embodiment, the RCPs comprise a cleavage site, such that either after or during the rolling circle amplification, the RCP concatamer may be cleaved into amplicons. In some embodiments, this facilitates the detection, since the amplicons are generally smaller and exhibit favorable hybridization kinetics on the surface. As will be appreciated by those in the art, the cleavage site can take on a number of forms, including, but not limited to, the use of restriction sites in the probe, the use of ribozyme sequences, or through the use or incorporation of nucleic acid cleavage moieties.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA (or in some cases, during the reaction), the product nucleic acid is contacted with the appropriate restriction endonuclease. This results in cleavage of the product nucleic acid into smaller fragments. The fragments are then hybridized with the capture probe that is immobilized resulting in a concentration of product fragments onto the detection electrode. Again, as outlined herein, these fragments can be detected in one of two ways: either labelled nucleotides are incorporated during the replication step, for example either as labeled individual dNTPs or through the use of a labeled primer, or an additional label probe is added.

In a preferred embodiment, the restriction site is a single-stranded restriction site chosen such that its complement occurs only once in the RCP.

In a preferred embodiment, the cleavage site is a ribozyme cleavage site as is generally described in Daubendiek et al., Nature Biotech. 15:273 (1997), hereby expressly incorporated by reference. In this embodiment, by using RCPs that encode catalytic RNAs, NTPs and an RNA polymerase, the resulting concatamer can self cleave, ultimately forming monomeric amplicons.

In a preferred embodiment, cleavage is accomplished using DNA cleavage reagents. For example, as is known in the art, there are a number of intercalating moieties that can effect cleavage, for example using light.

In a preferred embodiment, the RCPs do not comprise a cleavage site. Instead, the size of the RCP is designed such that it may hybridize "smoothly" to many capture probes on a surface. Alternatively, the reaction may be cycled such that very long concatamers are not formed.

In a preferred embodiment, the RCPs comprise a priming site, to allow the binding of a DNA polymerase primer. As is known in the art, many DNA polymerases require double stranded nucleic acid and a free terminus to allow nucleic acid synthesis. However, in some cases, for example when RNA polymerases are used, a primer may not be required (see Daubendiek, supra). Similarly, depending on the size and orientation of the target strand, it is possible that a free end of the target sequence can serve as the primer; see Baner et al., supra.

Thus, in a preferred embodiment, the padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

In a preferred embodiment, the primer may comprise the covalently attached ETMs.

In a preferred embodiment, the RCPs comprise a capture sequence. A capture sequence, as is outlined herein, is substantially complementary to a capture probe, as outlined herein.

In a preferred embodiment, the RCPs comprise a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

In a preferred embodiment, the RCPs comprise nucleotide analogs. For example, since it may be desirable to incorporate ETMs at specific locations within the amplicon (for example, at a cluster of 8-10 ETMs in a 20-30 basepair stretch, to allow optimal signaling and configuration of the detection hybridization complex), unique bases may be incorporated into the RCP. As is known in the art, isocytosine is a nucleoside analog that will only basepair with isoguanine, as is generally described in U.S. Pat. No. 5,681,702, hereby incorporated by reference in its entirety. By utilizing either isoC or isoG in the RCP, deoxy-isoC or deoxy-isoG labeled with an ETM can be added to the pool of nucleotides, resulting in the incorporation of ETMs at predetermined, specific locations.

In a preferred embodiment, the RCP/primer sets are designed to allow an additional level of amplification, sometimes referred to as "hyperbranching" or "cascade amplification". As described in Zhang et al., supra, by using several priming sequences and primers, a first concatamer can serve as the template for additional concatamers. In this embodiment, a polymerase that has high displacement activity is preferably used. In this embodiment, a first antisense primer is used, followed by the use of sense primers, to generate large numbers of concatamers and amplicons, when cleavage is used.

Thus, the invention provides for methods of detecting using RCPs as described herein. Once the ligation sequences of the RCP have hybridized to the target, forming a first hybridization complex, the ends of the RCP are ligated together as outlined above for OLA. The RCP primer is added, if necessary, along with a polymerase and dNTPs (or NTPs, if necessary).

The polymerase can be any polymerase as outlined herein, but is preferably one lacking 3' exonuclease activity (3' exo−). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

Thus, in a preferred embodiment the OLA/RCA is performed in solution followed by restriction endonuclease cleavage of the RCA product. The cleaved product is then applied to an array as described herein. The incorporation of an endonuclease site allows the generation of short, easily hybridizable sequences. Furthermore, the unique capture sequence in each rolling circle padlock probe sequence allows diverse sets of nucleic acid sequences to be analyzed in parallel on an array, since each sequence is resolved on the basis of hybridization specificity.

Again, these copies are subsequently detected by one of two methods; either hybridizing a label probe comprising ETMs which is complementary to the circular target or via the incorporation of ETM-labeled nucleotides in the amplification reaction. The label is detected a described herein.

In a preferred embodiment, the polymerase creates more than 100 copies of the circular DNA. In more preferred embodiments the polymerase creates more than 1000 copies of the circular DNA; while in a most preferred embodiment the polymerase creates more than 10,000 copies or more than 50,000 copies of the template.

The amplified circular DNA sequence is then detected by methods known in the art and as described herein. Detection is accomplished by hybridizing with a labeled probe. The probe is labeled directly or indirectly. Alternatively, labeled nucleotides are incorporated into the amplified circular DNA product. The nucleotides can be labeled directly, or indirectly as is further described herein.

The RCA as described herein finds use in allowing highly specific and highly sensitive detection of nucleic acid target sequences. In particular, the method finds use in improving the multiplexing ability of DNA arrays and eliminating costly sample or target preparation. As an example, a substantial savings in cost can be realized by directly analyzing genomic DNA on an array, rather than employing an intermediate PCR amplification step. The method finds use in examining genomic DNA and other samples including mRNA.

In addition the RCA finds use in allowing rolling circle amplification products to be easily detected by hybridization to probes in a solid-phase format. An additional advantage of the RCA is that it provides the capability of multiplex analysis so that large numbers of sequences can be analyzed in parallel. By combining the sensitivity of RCA and parallel detection on arrays, many sequences can be analyzed directly from genomic DNA.

In a preferred embodiment, OLA or RCP systems are designed to take on a particular configuration, as depicted in FIG. 10, sometimes referred to as a "cufflink" configuration. In this embodiment, the first ligation probe has a sequence that will hybridize to a first portion of the capture probe, and a target-specific sequence; the second ligation probe has a target-specific sequence, a "cufflink" sequence, and a recruitment linker comprising ETMs. Once the ligation occurs, and the ligated sequence is added to the array, a cufflink probe is added that comprises a first portion that hybridizes to a second portion of the capture probe, and a portion that hybridizes to the cufflink sequence. The cufflink probe then brings the recruitment linker and thus the ETMs into closer proximity to the electrode, providing for good signalling.

In a preferred embodiment, Invader™ technology is used to determine the identity of the base at the detection position. In general, Invader™ techniques rely on the use of structure-specific nucleases, where the structure can be formed as a result of the presence or absence of a mismatch. These structures are formed from two probes (the "invader probe" and the "signalling probe") hybridizing adjacently to two target domains of a target sequence at a detection position: the invader probe to the first domain and the signalling probe to the second domain. The signalling probe comprises a portion of at least one nucleotide that is complementary to the first domain as well, at the detection position, and thus overlaps with the invader probe, and a portion that is non-complementary to the first domain. The presence of this overlap forms a structure that a nuclease will recognize and cleave, freeing the non-complementary signalling portion. However, if no overlap exists, because the signalling probe does not contain a perfect match to the detection position, the structure is not formed and no cleavage occurs. Thus, cleavage is also sequence specific.

Accordingly, the present invention provides methods of determining the identity of a base at the detection position of a target sequence. In this embodiment, the target sequence comprises, 5' to 3', a first target domain comprising an overlap domain comprising at least a nucleotide in the detection position, and a second target domain contiguous with the detection position. A first probe is hybridized to the first target domain of the target sequence. A second probe, comprising a first portion that hybridizes to the second target domain of the target sequence and a second portion that does not hybridize to the target sequence, is hybridized to the second target domain. If the second probe comprises a base that is perfectly complementary to the detection position a cleavage structure is formed. The addition of a cleavage enzyme, such as is described in U.S. Pat. Nos. 5,846,717; 5,614,402; 5,719,029; 5,541,311 and 5,843,669, all of which are expressly incorporated by reference, results in the cleavage of the detection sequence from the signalling probe. This then can be used as a target sequence in an assay complex.

As above, as will be appreciated by those in the art, the Invader™ reaction may be done in solution, generating a plurality of detection sequences. These then may be added to a detection electrode as outlined herein.

As will be appreciated by those in the art, these techniques may be done for the two strands of a double-stranded target sequence. The target sequence is denatured, and two sets of probes are added: one set as outlined above for one strand of the target, and a separate set (i.e. third and fourth primer robe nucleic acids) for the other strand of the target. In a preferred embodiment, the first and third probes will hybridize, and the second and fourth probes will hybridize, such that amplification can occur.

Again, as outlined above, the detection of the Invader™ reaction can occur directly, in the case where the detection sequence comprises at least one ETM, or indirectly, using sandwich assays, through the use of additional probes; that is, the detection sequences can serve as target sequences, and detection may utilize amplification probes, capture probes, capture extender probes, label probes, and label extender probes, etc.

In a preferred embodiment, single base extension (SBE; sometimes referred to as "minisequencing") is used to determine the identity of the base at the detection position. Briefly, SBE is a technique that utilizes an extension primer that hybridizes to the target nucleic acid immediately adjacent to the detection position. A polymerase (generally a DNA polymerase) is used to extend the 3' end of the primer with a nucleotide analog labeled with an ETM as described herein. A nucleotide is only incorporated into the growing nucleic acid strand if it is complementary to the base in the target strand at the detection position. The nucleotide is derivatized such that no further extensions can occur, so only a single nucleotide is added. Once the labeled nucleotide is added, detection of the ETM proceeds as outlined herein.

As will be appreciated by those in the art, the determination of the base at the detection position can proceed in several ways. In a preferred embodiment, the reaction is run with all four nucleotides, each with a different label, e.g. ETMs with different redox potentials, as is generally outlined herein. Alternatively, a single label is used, by using four electrode pads as outlined above or sequential reactions; for example, dATP can be added to the assay complex, and the generation of a signal evaluated; the dATP can be removed and dTTP added, etc.

The reaction is initiated by introducing the assay complex comprising the target sequence (i.e. the array) to a solution comprising a first nucleotide analog. By "nucleotide analog" in this context herein is meant a deoxynucleoside-triphosphate (also called deoxynucleotides or dNTPs, i.e. dATP, dTTP, dCTP and dGTP), that is further derivatized to be chain terminating. The nucleotides may be naturally occurring, such as deoxynucleotides, or non-naturally occurring. Preferred embodiments utilize dideoxy-triphosphate nucleotides (ddNTPs). Generally, a set of nucleotides comprising ddATP, ddCTP, ddGTP and ddTTP is used.

In addition, as will be appreciated by those in the art, the single base extension reactions of the present invention allow the precise incorporation of modified bases into a growing nucleic acid strand. Thus, any number of modified nucleotides may be incorporated for any number of reasons, including probing structure-function relationships (e.g. DNA:DNA or DNA:protein interactions), cleaving the nucleic acid, crosslinking the nucleic acid, incorporate mismatches, etc.

In addition to a first nucleotide, the solution also comprises an extension enzyme, generally a DNA polymerase. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase. If the NTP is complementary to the base of the detection position of the target sequence, which is adjacent to the extension primer, the extension enzyme will add it to the extension primer at the interrogation position. Thus, the extension primer is modified, i.e. extended, to form a modified primer, sometimes referred to herein as a "newly synthesized strand". If desired, the temperature of the reaction can be adjusted (or cycled) such that amplification occurs, generating a plurality of modified primers.

As will be appreciated by those in the art, the configuration of the SBE system can take on several forms. As for the LCR reaction, the reaction may be done in solution, and then the newly synthesized strands, with the base-specific ETM labels, can be detected. For example, they can be directly hybridized to capture probes that are complementary to the extension primers, and the presence of the ETM then detected, using either "mechanism-1" or "mechanism-2" systems as described herein.

Alternatively, the reaction may be done on a surface by capturing the target sequence and then running the SBE reaction. Similarly, the capture probe itself can be used as the extension probe, with its terminus being directly adjacent to the detection position. Upon the addition of the target sequence and the SBE reagents, the modified primer is formed comprising an ETM, and then detected.

In a preferred embodiment, the method used to detect the base at the detection position is allelic PCR, referred to herein as "aPCR". As described in Newton et al., Nucl. Acid Res. 17:2503 (1989), hereby expressly incorporated by reference, allelic PCR allows single base discrimination based on the fact that the PCR reaction does not proceed well if the terminal 3'-nucleotide is mismatched, assuming the DNA polymerase being used lacks a 3'-exonuclease proofreading activity. Accordingly, the identification of the base proceeds by using allelic PCR primers (sometimes referred to herein as aPCR primers) that have readout positions at their 3' ends. Thus the target sequence comprises a first domain comprising at its 5' end a detection position.

In general, aPCR may be briefly described as follows. A double stranded target nucleic acid is denatured, generally by raising the temperature, and then cooled in the presence of an excess of a aPCR primer, which then hybridizes to the first target strand. If the readout position of the aPCR primer basepairs correctly with the detection position of the target sequence, a DNA polymerase (again, that lacks 3'-exonuclease activity) then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus aPCR steps are denaturation, annealing and extension. The particulars of aPCR are well known, and include the use of a thermostable polymerase such as Taq I polymerase and thermal cycling.

Accordingly, the aPCR reaction requires at least one aPCR primer, a polymerase, and a set of dNTPs. As outlined herein, the primers may comprise the label, or one or more of the dNTPs may comprise a label.

In a preferred embodiment, the invention provides novel methods and compositions for nucleic acid assays on solid supports. Without being bound by theory, it appears that when nucleic acids are hybridized to surface probes, the relatively high concentration of negative charge at the surface provides a "destabilizing environment", similar to the introduction of heat, that allows the discrimination of perfect and imperfect complementarity in the presence of an excess of perfect complementary probes. That is, when a first capture probe is a perfect match to a target sequence and a second capture probe comprises a single basepair change at the interrogation position, at temperatures below the Tm of the mismatch, both hybrids will form. However, the addition of an excess of a probe (herein termed a "competimer") that matches the second capture probe at the interrogation position, drives off the mismatch-bound target sequence in favor of competimer binding. Essentially, this is a reduction in binding of sequences having imperfect complementarity; this can be considered to be a reduction in non-specific binding. This does not appear to be the case in solution based systems; again, without being bound by theory, this appears to be the result in a difference in "off rate" as a function of the destabilizing environment. As shown in the Examples, this allows a significant reduction in the binding of mismatched nucleic acids to surfaces.

The general idea is shown in FIG. 3. FIG. 3A depicts a surface with two capture probes, each differing by a single base at the interrogation position, one of which is "perfect" as compared to the target sequence and one that contains a mismatch. In the absence of the competimer, the target binds to both capture probes. Upon addition of the competimer, the competimer drives off the target containing the mismatch leaving the perfect hybrid intact. As will be appreciated by those in the art, this can be configured in a variety of ways. As shown in FIG. 3B, a capture extender can be used. Alternatively, as shown in FIG. 3C, the detection position can be queried using different label probes. As will be appreciated by those in the art, other configurations (e.g. using amplifier probes, label extender probes, etc.) are also possible. What is important is that the competimer be directed to the region of the target sequence comprising the detection position.

Accordingly, the present invention provides compositions comprising substrates with a plurality of array locations. By "substrate" or "solid support" or other grammatical equivalents herein is meant any material that can be modified to contain discrete individual sites appropriate for the attachment or association of nucleic acids. Suitable substrates include metal surfaces such as gold, electrodes as defined below, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, and a variety of other polymers.

The substrate includes array locations. By "array locations" or "pads" or "sites" herein meant a location on the substrate that comprises a covalently attached nucleic acid probe.

The compositions further comprise a plurality of competimers. By "competimer" herein is meant a nucleic acid that is substantially complementary to a nucleic acid for which specificity is desired to be more stable than a mismatch. As outlined herein, this can take on a number of forms. The competimer must be substantially complementary to its target. By "substantially complementary" herein is meant that the competimers are sufficiently complementary to hybridize under normal reaction conditions. In a preferred embodiment, the competimers are perfectly complementary to its target. However, depending on how close the different target sequences are, different levels of complementarity may be used. For example, for SNP analysis, the target sequences are generally identical save for the detection position, and thus to utilize competimers they must be perfectly complementary. However, for non-related targets, it is only important that the competimer have a higher stability in a duplex than the nucleic acid being replaced. Therefore, in this embodiment, it may be possible to utilize competimers that do not exhibit perfect complementarity to their targets.

In a preferred embodiment, as is depicted in FIGS. 3A and 3B, the competimer is complementary to either a capture probe or to a portion of a capture extender probe. That is, in a preferred embodiment when the target sequence hybridizes directly to a capture probe, the competimers are complementary to the capture probe. However, if a capture extender probe is used as outlined herein, the capture extender probe has a first portion that hybridizes to the target sequence and a second portion that hybridizes to the capture probe. In this instance, the competimer will hybridize to the first portion of the capture probe.

In a preferred embodiment, as is depicted in FIG. 3C, the competimer is complementary to the label probe binding region (sometimes referred to herein as the label probe recognition sequence) of the target sequence.

The competimers of the invention may be added at any time during the assay. In a preferred embodiment, the competimers are added after the formation of the assay complex, and thus serve to "drive off" imperfect binding. This may be done with or without a wash step. Alternatively, the competimers can be added prior to or during the formation of the assay complex. In this embodiment, depending on the use of the array and the detection sensitivity, it is important to note that the competimer is also competing with the target for binding, and thus the amount of surface bound target may decrease.

All of the above compositions and methods are directed to the determination of the identification of the base at one or more detection positions within a target nucleic acid. The detection systems of the present invention are based on the incorporation of an electron transfer moiety (ETM) into an assay complex as the result of target analyte binding.

In general, there are two basic detection mechanisms. In a preferred embodiment, detection of an ETM is based on electron transfer through the stacked n-orbitals of double stranded nucleic acid. This basic mechanism is described in U.S. Pat. Nos. 5,591,578, 5,770,369, 5,705,348, and PCT US97/20014 and is termed "mechanism-1" herein. Briefly, previous work has shown that electron transfer can proceed rapidly through the stacked n-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected.

Alternatively, the ETM can be detected, not necessarily via electron transfer through nucleic acid, but rather can be directly detected on an electrode comprising a SAM; that is, the electrons from the ETMs need not travel through the stacked π orbitals in order to generate a signal. As above, in this embodiment, the detection electrode preferably comprises a self-assembled monolayer (SAM) that serves to shield the electrode from redox-active species in the sample. In this embodiment, the presence of ETMs on the surface of a SAM, that has been formulated to comprise slight "defects" (sometimes referred to herein as "microconduits", "nanoconduits" or "electroconduits") can be directly detected. This basic idea is termed "mechanism-2" herein. Essentially, the electroconduits allow particular ETMs access to the surface. Without being bound by theory, it should be noted that the configuration of the electroconduit depends in part on the ETM chosen. For example, the use of relatively hydrophobic ETMs allows the use of hydrophobic electroconduit forming species, which effectively exclude hydrophilic or charged ETMs. Similarly, the use of more hydrophilic or charged species in the SAM may serve to exclude hydrophobic ETMs.

It should be noted that these defects are to be distinguished from "holes" that allow direct contact of sample components with the detection electrode. As is more fully outlined below, the electroconduits can be generated in several general ways, including but not limited to the use of rough electrode surfaces, such as gold electrodes formulated on PC circuit boards; or the inclusion of at least two different species in the monolayer, i.e. using a "mixed monolayer", at least one of which is a electroconduit-forming species (EFS). Thus, upon binding of a target analyte, a soluble binding ligand comprising an ETM is brought to the surface, and detection of the ETM can proceed, putatively through the "electroconduits" to the electrode. Essentially, the role of the SAM comprising the defects is to allow contact of the ETM with the electronic surface of the electrode, while still providing the benefits of shielding the electrode from solution components and reducing the amount of non-specific binding to the electrodes. Viewed differently, the role of the binding ligand is to provide specificity for a recruitment of ETMs to the surface, where they can be directly detected.

Thus, in either embodiment, as is more fully outlined below, an assay complex is formed that contains an ETM, which is then detected using the detection electrode.

Accordingly, the present invention provides methods and compositions useful in the detection of nucleic acids. As will be appreciated by those in the art, the compositions of the invention can take on a wide variety of configurations. As is more fully outlined below, preferred systems of the invention work as follows. A target nucleic acid sequence is attached (via hybridization) to an electrode comprising a monolayer, generally including conductive oligomers. This attachment can be either directly to a capture probe on the surface, or indirectly, using capture extender probes. In some embodiments, the target sequence itself comprises the ETMs. Alternatively, a label probe is then added, forming an assay complex. The attachment of the label probe may be direct (i.e. hybridization to a portion of the target sequence), or indirect (i.e. hybridization to an amplifier probe that hybridizes to the target sequence), with all the required nucleic acids forming an assay complex. As a result of the hybridization of the first portion of the label probe, the second portion of the label probe, the "recruitment linker", containing the ETMs is brought into spatial proximity to SAM surface on the electrode, and the presence of the ETM can then be detected electronically.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture ligands to many thousands can be made. Generally, the array will comprise from two to as many as 100,000 or more, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

Thus, in a preferred embodiment, the compositions comprise an electrode. By "electrode" herein is meant a composition, which, when connected to an electronic device, is able to sense a current or charge and convert it to a signal. Alternatively an electrode can be defined as a composition which can apply a potential to and/or pass electrons to or from species in the solution. Thus, an electrode is an ETM as described herein. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the SAMs comprising conductive oligomers and nucleic acids bound to the inner surface. This allows a maximum of surface area containing the nucleic acids to be exposed to a small volume of sample.

In a preferred embodiment, the detection electrodes are formed on a substrate. In addition, the discussion herein is generally directed to the formation of gold electrodes, but as will be appreciated by those in the art, other electrodes can be used as well. The substrate can comprise a wide variety of materials, as will be appreciated by those in the art, with printed circuit board (PCB) materials being particularly preferred. Thus, in general, the suitable substrates include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), GETEK (a blend of polypropylene oxide and fiberglass), etc.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

In some embodiments, glass may not be preferred as a substrate.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

The substrates can be part of a larger device comprising a detection chamber that exposes a given volume of sample to the detection electrode. Generally, the detection chamber ranges from about 1 mL to 1 ml, with about 10 µL to 500 µL being preferred. As will be appreciated by those in the art, depending on the experimental conditions and assay, smaller or larger volumes may be used.

In some embodiments, the detection chamber and electrode are part of a cartridge that can be placed into a device comprising electronic components (an AC/DC voltage source, an ammeter, a processor, a read-out display, temperature controller, light source, etc.). In this embodiment, the interconnections from each electrode are positioned such that upon insertion of the cartridge into the device, connections between the electrodes and the electronic components are established.

Detection electrodes on circuit board material (or other substrates) are generally prepared in a wide variety of ways. In general, high purity gold is used, and it may be deposited on a surface via vacuum deposition processes (sputtering and evaporation) or solution deposition (electroplating or electroless processes). When electroplating is done, the substrate must initially comprise a conductive material; fiberglass circuit boards are frequently provided with copper foil. Frequently, depending on the substrate, an adhesion layer between the substrate and the gold in order to insure good mechanical stability is used. Thus, preferred embodiments utilize a deposition layer of an adhesion metal such as chromium, titanium, titanium/tungsten, tantalum, nickel or palladium, which can be deposited as above for the gold. When electroplated metal (either the adhesion metal or the electrode metal) is used, grain refining additives, frequently referred to in the trade as brighteners, can optionally be added to alter surface deposition properties. Preferred brighteners are mixtures of organic and inorganic species, with cobalt and nickel being preferred.

In general, the adhesion layer is from about 100 Å thick to about 25 microns (1000 microinches). The If the adhesion metal is electrochemically active, the electrode metal must be coated at a thickness that prevents "bleed-through"; if the adhesion metal is not electrochemically active, the electrode metal may be thinner. Generally, the electrode metal (preferably gold) is deposited at thicknesses ranging from about 500 Å to about 5 microns (200 microinches), with from about 30 microinches to about 50 microinches being preferred. In general, the gold is deposited to make electrodes ranging in size from about 5 microns to about 5 mm in diameter, with about 100 to 250 microns being preferred. The detection electrodes thus formed are then preferably cleaned and SAMs added, as is discussed below.

Thus, the present invention provides methods of making a substrate comprising a plurality of gold electrodes. The methods first comprise coating an adhesion metal, such as nickel or palladium (optionally with brightener), onto the substrate. Electroplating is preferred. The electrode metal, preferably gold, is then coated (again, with electroplating preferred) onto the adhesion metal. Then the patterns of the device, comprising the electrodes and their associated interconnections are made using lithographic techniques, particularly photolithographic techniques as are known in the art, and wet chemical etching. Frequently, a non-conductive chemically resistive insulating material such as solder mask or plastic is laid down using these photolithographic techniques, leaving only the electrodes and a connection point to the leads exposed; the leads themselves are generally coated.

The methods continue with the addition of SAMs. In a preferred embodiment, drop deposition techniques are used to add the required chemistry, i.e. the monolayer forming species, one of which is preferably a capture ligand comprising species. Drop deposition techniques are well known for making "spot" arrays. This is done to add a different composition to each electrode, i.e. to make an array comprising different capture ligands. Alternatively, the SAM species may be identical for each electrode, and this may be accomplished using a drop deposition technique or the immersion of the entire substrate or a surface of the substrate into the solution.

Thus, in a preferred embodiment, the electrode comprises a monolayer, comprising electroconduit forming species (EFS). As outlined herein, the efficiency of target analyte binding (for example, oligonucleotide hybridization) may increase when the analyte is at a distance from the electrode. Similarly, non-specific binding of biomolecules, including the target analytes, to an electrode is generally reduced when a monolayer is present. Thus, a monolayer facilitates the maintenance of the analyte away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accessibility to the electrode.

By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. A majority of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer.

In general, the SAMs of the invention can be generated in a number of ways and comprise a number of different components, depending on the electrode surface and the system used. For "mechanism-1" embodiments, preferred embodiments utilize two monolayer forming species: a monolayer forming species (including insulators or conductive oligomers) and a conductive oligomer species comprising the capture binding ligand, although as will be appreciated by those in the art, additional monolayer forming species can be included as well. For "mechanism-2" systems, the composition of the SAM depends on the detection electrode surface. In general, two basic "mechanism-2" systems are described; detection electrodes comprising "smooth" surfaces, such as gold ball electrodes, and those comprising "rough" surfaces, such as those that are made using commercial processes on PC circuit boards. In general, without being bound by theory, it appears that monolayers made on imperfect surfaces, i.e. "rough" surfaces, spontaneously form monolayers containing enough electroconduits even in the absence of EFS, probably due to the fact that the formation of a uniform monolayer on a rough surface is difficult. "Smoother" surfaces, however, may require the inclusion of sufficient numbers of EFS to generate the electroconduits, as the uniform surfaces allow a more uniform monolayer to form. Again, without being bound by theory, the inclusion of species that disturb the uniformity of the monolayer, for example by including a rigid molecule in a background of more flexible ones, causes electroconduits. Thus "smooth" surfaces comprise monolayers comprising three components: an insulator species, a EFS, and a species comprising the capture ligand, although in some circumstances, for example when the capture ligand species is included at high density, the capture ligand species can serve as the EFS. "Smoothness" in this context is not measured physically but rather as a function of an increase in the measured signal when EFS are included. That is, the signal from a detection electrode coated with monolayer forming species is compared to a signal from a detection electrode coated with monolayer forming species including a EFS. An increase indicates that the surface is relatively smooth, since the inclusion of a EFS served to facilitate the access of the ETM to the electrode. It should also be noted that while the discussion herein is mainly directed to gold electrodes and thiol-containing monolayer forming species, other types of electrodes and monolayer-forming species can be used.

It should be noted that the "electroconduits" of mechanism-2 systems do not result in direct contact of sample components with the electrode surface; that is, the electroconduits are not large pores or holes that allow physical access to the electrode. Rather, without being bound by theory, it appears that the electroconduits allow certain types of ETMs, particularly hydrophobic ETMs, to penetrate sufficiently into the monolayer to allow detection. However, other types of redox active species, including some hydrophilic species, do not penetrate into the monolayer, even with electroconduits present. Thus, in general, redox active species that may be present in the sample do not give substantial signals as a result of the electroconduits. While the exact system will vary with the composition of the SAM and the choice of the ETM, in general, the test for a suitable SAM to reduce non-specific binding that also has sufficient electroconduits for ETM detection is to add either ferrocene or ferrocyanide to the SAM; the former should give a signal and the latter should not.

Accordingly, in mechanism-1 systems, the monolayer comprises a first species comprising a conductive oligomer comprising the capture binding ligand, as is more fully outlined below, and a second species comprising a monolayer forming species, including either or both insulators or conductive oligomers.

In a preferred embodiment, the monolayer comprises electroconduit-forming species. By "electroconduit-forming species" or "EFS" herein is meant a molecule that is capable of generating sufficient electroconduits in a monolayer, generally of insulators such as alkyl groups, to allow detection of ETMs at the surface. In general, EFS have one or more of the following qualities: they may be relatively rigid molecules, for example as compared to an alkyl chain; they may attach to the electrode surface with a geometry different from the other monolayer forming species (for example, alkyl chains attached to gold surfaces with thiol groups are thought to attach at roughly 45° angles, and phenyl-acetylene chains attached to gold via thiols are thought to go down at 90° angles); they may have a structure that sterically interferes or interrupts the formation of a tightly packed monolayer, for example through the inclusion of branching groups such as alkyl groups, or the inclusion of highly flexible species, such as polyethylene glycol units; or they may be capable of being activated to form electroconduits; for example, photoactivatable species that can be selectively removed from the surface upon photoactivation, leaving electroconduits.

Preferred EFS include conductive oligomers, as defined below, and phenyl-acetylene-polyethylene glycol species, as well as asymmetrical SAM-forming disulfide species such as depicted in FIG. 9 and the figures of U.S. Ser. No. 60/145,912 filed Jul. 27, 1999, hereby expressly incorporated by reference. However, in some embodiments, the EFS is not a conductive oligomer.

In a preferred embodiment, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping n-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons.

In a preferred embodiment, the conductive oligomers have a conductivity, S, of from between about $10^{-6}$ to about $10^4$ $\Omega^{-1}\text{cm}^{-1}$, with from about $10^{-5}$ to about $10^3$ $\Omega^{-1}\text{cm}^{-1}$ being preferred, with these S values being calculated for molecules ranging from about 20 Å to about 200 Å. As described below, insulators have a conductivity S of about $10^{-7}$ $\Omega^{-1}\text{cm}^{-1}$ or lower, with less than about $10^{-8}$ $\Omega^{-1}\text{cm}^{-1}$ being preferred. See generally Gardner et al., Sensors and Actuators A 51 (1995) 57-66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during nucleic acid synthesis (such that nucleosides containing the conductive oligomers may be added to a nucleic acid synthesizer during the synthesis of the compositions of the invention), ii) during the attachment of the conductive oligomer to an electrode, or iii) during hybridization assays. In addition, conductive oligomers that will promote the formation of self-assembled monolayers are preferred.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 1:

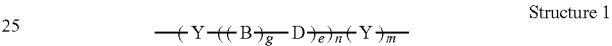

Structure 1

As will be understood by those in the art, all of the structures depicted herein may have additional atoms or structures; i.e. the conductive oligomer of Structure 1 may be attached to ETMs, such as electrodes, transition metal complexes, organic ETMs, and metallocenes, and to nucleic acids, or to several of these. Unless otherwise noted, the conductive oligomers depicted herein will be attached at the left side to an electrode; that is, as depicted in Structure 1, the left "Y" is connected to the electrode as described herein. If the conductive oligomer is to be attached to a nucleic acid, the right "Y", if present, is attached to the nucleic acid, either directly or through the use of a linker, as is described herein.

In this embodiment, Y is an aromatic group, n is an integer from 1 to 50, g is either 1 or zero, e is an integer from zero to 10, and m is zero or 1. When g is 1, B-D is a bond able to conjugate with neighboring bonds (herein referred to as a "conjugated bond"), preferably selected from acetylene, B-D is a conjugated bond, preferably selected from acetylene, alkene, substituted alkene, amide, azo, —C=N— (including —N=C—, —CR=N— and —N=CR—), —Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups.

The aromatic group may be substituted with a substitution group, generally depicted herein as R. R groups may be added as necessary to affect the packing of the conductive oligomers, i.e. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —$NH_2$, —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCHO groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —$(O—CH_2—CH_2)_n$— group, although each carbon atom of the ethylene group may also be singly or doubly substituted, i.e. —$(O—CR_2—CR_2)_n$—, with R as described above. Ethylene glycol derivatives with other heteroatoms in place of oxygen (i.e. —$(N—CH_2—CH_2)_n$— or —$(S—CH_2—CH_2)_n$—, or with substitution groups) are also preferred.

Preferred substitution groups include, but are not limited to, methyl, ethyl, propyl, alkoxy groups such as —O—$(CH_2)_2CH_3$ and O—$(CH_2)_4CH_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B-D is a bond linking two atoms or chemical moieties. In a preferred embodiment, B-D is a conjugated bond, containing overlapping or conjugated π-orbitals.

Preferred B-D bonds are selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly preferred B-D bonds are acetylene, alkene, amide, and substituted derivatives of these three, and azo. Especially preferred B-D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 1 conductive oligomer, e is preferably 1 and the D moiety may be carbonyl or a heteroatom moiety as defined above.

As above for the Y rings, within any single conductive oligomer, the B-D bonds (or D moieties, when g=0) may be all the same, or at least one may be different. For example, when m is zero, the terminal B-D bond may be an amide bond, and the rest of the B-D bonds may be acetylene bonds. Generally, when amide bonds are present, as few amide bonds as possible are preferable, but in some embodiments all the B-D bonds are amide bonds. Thus, as outlined above for the Y rings, one type of B-D bond may be present in the conductive oligomer within a monolayer as described below, and another type above the monolayer level, for example to give greater flexibility for nucleic acid hybridization when the nucleic acid is attached via a conductive oligomer.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, when a nucleic acid is attached via a conductive oligomer, as is more fully described below, the length of the conductive oligomer is such that the closest nucleotide of the nucleic acid is positioned from about 6 Å to about 100 Å (although distances of up to 500 Å may be used) from the electrode surface, with from about 15 Å to about 60 Å being preferred and from about 25 Å to about 60 Å also being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B-D bond or D moiety, i.e. the D atom is attached to the nucleic acid either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the nucleic acid or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®-like oligomers, such as —(CF$_2$)$_n$—, —(CHF)$_n$— and —(CFR)$_n$—. See for example, Schumm et al., Angew. Chem. Intl. Ed. Engl. 33:1361 (1994); Grosshenny et al., Platinum Metals Rev. 40(1):26-35 (1996); Tour, Chem. Rev. 96:537-553 (1996); Hsung et al., Organometallics 14:4808-4815 (1995; and references cited therein, all of which are expressly incorporated by reference.

Particularly preferred conductive oligomers of this embodiment are depicted below:

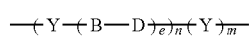

Structure 2

Structure 2 is Structure 1 when g is 1. Preferred embodiments of Structure 2 include: e is zero, Y is pyrole or substituted pyrole; e is zero, Y is thiophene or substituted thiophene; e is zero, Y is furan or substituted furan; e is zeros Y is phenyl or substituted phenyl; e is zero, Y is pyridine or substituted pyridine; e is 1, B-D is acetylene and Y is phenyl or substituted phenyl (see Structure 4 below). A preferred embodiment of Structure 2 is also when e is one, depicted as Structure 3 below:

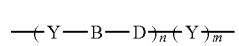

Structure 3

Preferred embodiments of Structure 3 are: Y is phenyl or substituted phenyl and B-D is azo; Y is phenyl or substituted phenyl and B-D is acetylene; Y is phenyl or substituted phenyl and B-D is alkene; Y is pyridine or substituted pyridine and B-D is acetylene; Y is thiophene or substituted thiophene and B-D is acetylene; Y is furan or substituted furan and B-D is acetylene; Y is thiophene or furan (or substituted thiophene or furan) and B-D are alternating alkene and acetylene bonds.

Most of the structures depicted herein utilize a Structure 3 conductive oligomer. However, any Structure 3 oligomers may be substituted with any of the other structures depicted herein, i.e. Structure 1 or 8 oligomer, or other conducting oligomer, and the use of such Structure 3 depiction is not meant to limit the scope of the invention.

Particularly preferred embodiments of Structure 3 include Structures 4, 5, 6 and 7, depicted below:

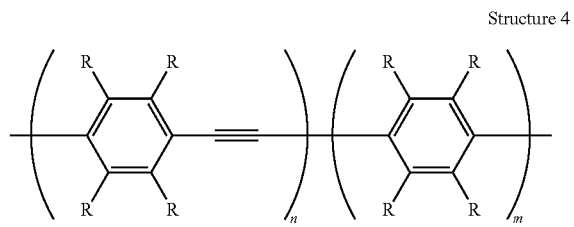

Structure 4

Particularly preferred embodiments of Structure 4 include: n is two, m is one, and R is hydrogen; n is three, m is zero, and R is hydrogen; and the use of R groups to increase solubility.

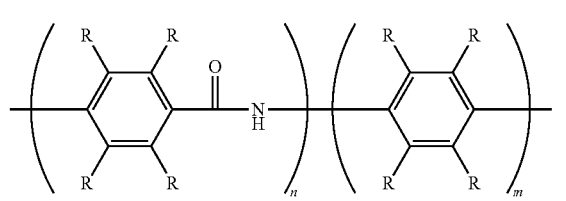

Structure 5

When the B-D bond is an amide bond, as in Structure 5, the conductive oligomers are pseudopeptide oligomers. Although the amide bond in Structure 5 is depicted with the carbonyl to the left, i.e. —CONH—, the reverse may also be used, i.e. —NHCO—. Particularly preferred embodiments of Structure 5 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

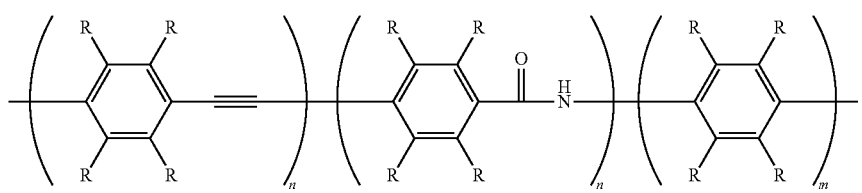

Structure 6

Preferred embodiments of Structure 6 include the first n is two, second n is one, m is zero, and all R groups are hydrogen, or the use of R groups to increase solubility.

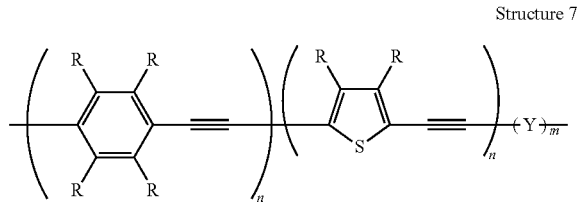

Structure 7

Preferred embodiments of Structure 7 include: the first n is three, the second n is from 1-3, with m being either 0 or 1, and the use of R groups to increase solubility.

In a preferred embodiment, the conductive oligomer has the structure depicted in Structure 8:

Structure 8

In this embodiment, C are carbon atoms, n is an integer from 1 to 50, m is 0 or 1, J is a heteroatom selected from the group consisting of oxygen, nitrogen, silicon, phosphorus, sulfur, carbonyl or sulfoxide, and G is a bond selected from alkane, alkene or acetylene, such that together with the two carbon atoms the C-G-C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In some embodiments, for example when ETMs are not present, if m=0 then at least one of the G bonds is not an alkane bond.

In a preferred embodiment, the m of Structure 8 is zero. In a particularly preferred embodiment, m is zero and G is an alkene bond, as is depicted in Structure 9:

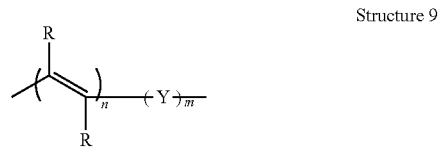

Structure 9

The alkene oligomer of structure 9, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 1 and 8.

In addition, the terminus of at least some of the conductive oligomers in the monolayer are electronically exposed. By "electronically exposed" herein is meant that upon the placement of an ETM in close proximity to the terminus, and after initiation with the appropriate signal, a signal dependent on the presence of the ETM may be detected. The conductive oligomers may or may not have terminal groups. Thus, in a preferred embodiment, there is no additional terminal group, and the conductive oligomer terminates with one of the groups depicted in Structures 1 to 9; for example, a B-D bond such as an acetylene bond. Alternatively, in a preferred embodiment, a terminal group is added, sometimes depicted herein as "Q". A terminal group may be used for several reasons; for example, to contribute to the electronic availability of the conductive oligomer for detection of ETMs, or to alter the surface of the SAM for other reasons, for example to prevent non-specific binding. For example, there may be negatively charged groups on the terminus to form a negatively charged surface such that when the nucleic acid is DNA or RNA the nucleic acid is repelled or prevented from lying down on the surface, to facilitate hybridization. Preferred terminal groups include —NH$_2$, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

It will be appreciated that the monolayer may comprise different conductive oligomer species, although preferably the different species are chosen such that a reasonably uniform SAM can be formed. Thus, for example, when nucleic acids are covalently attached to the electrode using conductive oligomers, it is possible to have one type of conductive oligomer used to attach the nucleic acid, and another type functioning to detect the ETM. Similarly, it may be desirable to have mixtures of different lengths of conductive oligomers in the monolayer, to help reduce non-specific signals. Thus, for example, preferred embodiments utilize conductive oligomers that terminate below the surface of the rest of the monolayer, i.e. below the insulator layer, if used, or below some fraction of the other conductive oligomers. Similarly, the use of different conductive oligomers may be done to facilitate monolayer formation, or to make monolayers with altered properties.

In a preferred embodiment, the monolayer forming species are "interrupted" conductive oligomers, containing an alkyl portion in the middle of the conductive oligomer.

Figure 11B:
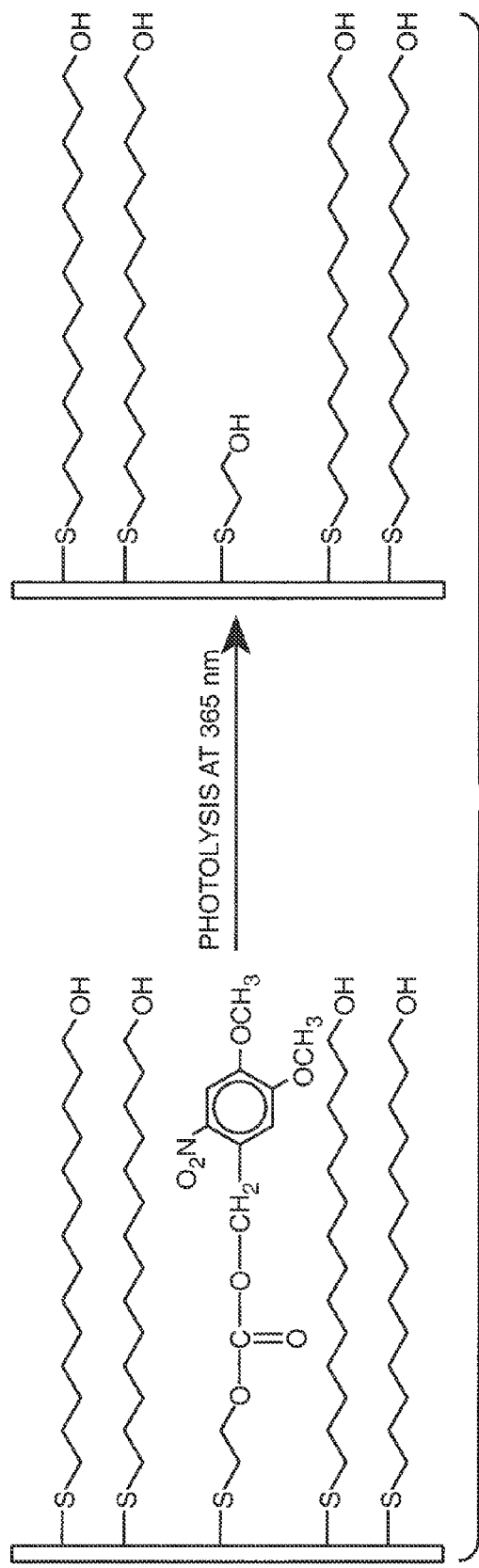
Figure 15A:
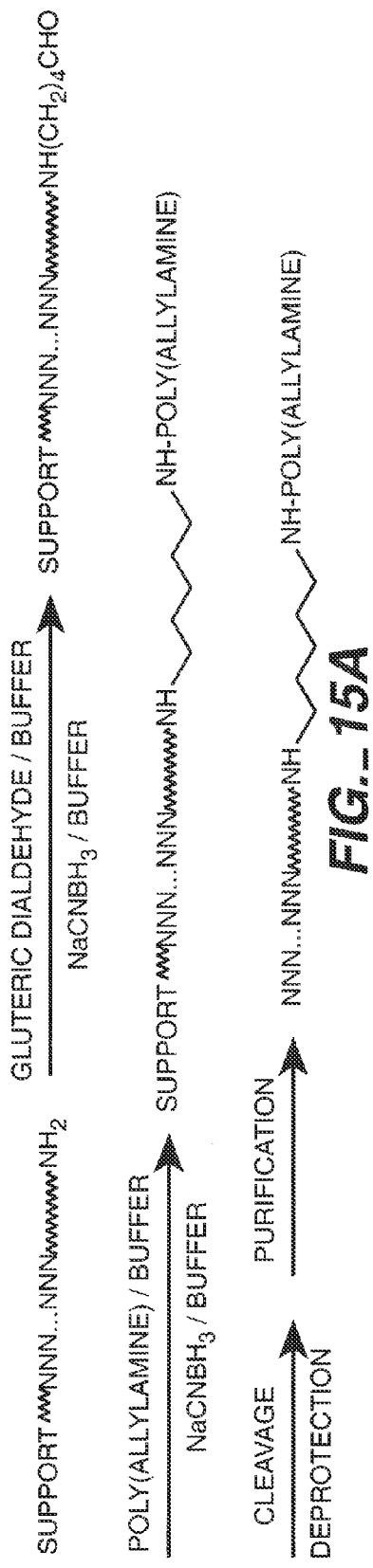
FIGS. 15A and 15B depict another post-synthesis reaction for the attachment of detectable labels, in this embodiment ETMs, to nucleic acids.
Figure 15B:
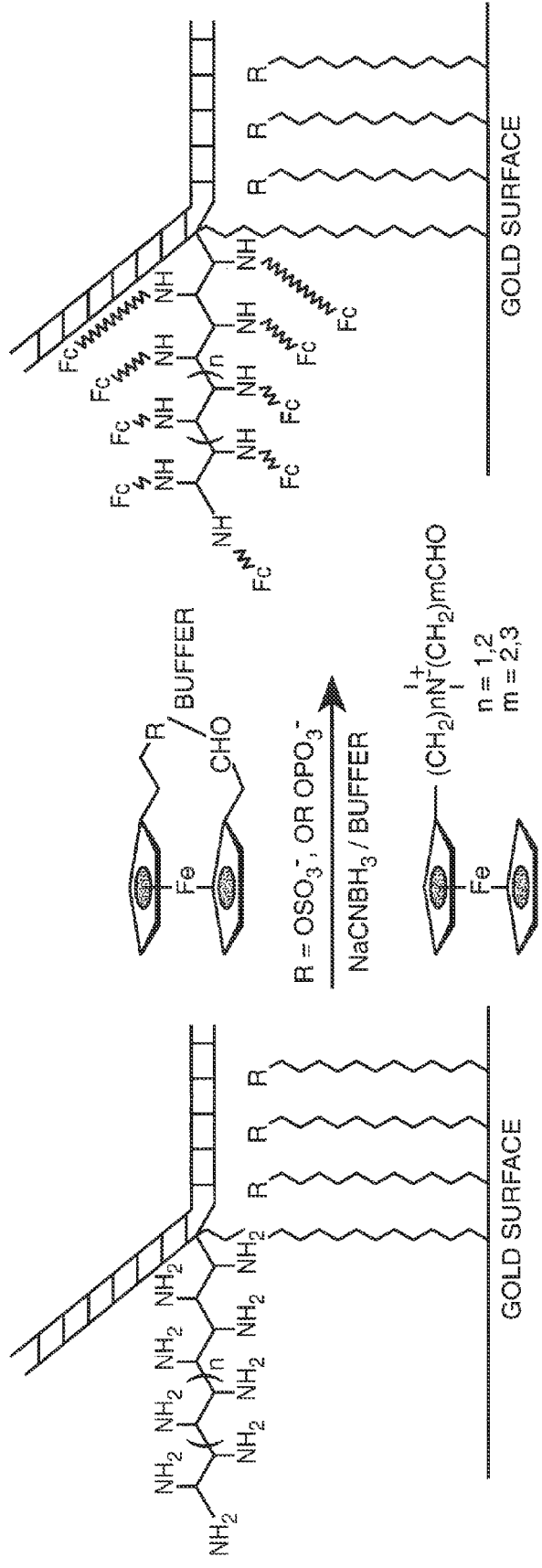

In a preferred embodiment, the monolayer comprises photoactivatable species as EFS. This general scheme is depicted in FIG. 11. Photoactivatable species are known in the art, and include 4,5-dimethoxy-2-nitrobenzyl ester, which can be photolyzed at 365 nm for 2 hours.

In a preferred embodiment, the monolayer may further comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferrably slower than the rate through the conductive oligomers described herein.

In a preferred embodiment, the insulators have a conductivity, S, of about $10^{-7}$ $\Omega^{-1}cm^{-1}$ or lower, with less than about $10^{-8}$ $\Omega^{-1}cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

Suitable insulators are known in the art, and include, but are not limited to, —$(CH_2)_n$—, —$(CRH)_n$—, and —$(CR_2)_n$—, ethylene glycol or derivatives using other heteroatoms in place of oxygen, i.e. nitrogen or sulfur (sulfur derivatives are not preferred when the electrode is gold).

As for the conductive oligomers, the insulators may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. Similarly, the insulators may contain terminal groups, as outlined above, particularly to influence the surface of the monolayer.

In a preferred embodiment, the insulator species included in the SAM utilizes novel methods and compositions comprising asymmetric disulfides. As outlined herein, the signals generated from label probes can be dependent on the behavior or properties of the SAM. SAMs comprising "nanoconduits" or "electroconduits", as outlined in U.S. Ser. No. 60/145,912, filed Jul. 27, 1999, hereby expressly incorporated herein by reference in its entirety, give good signals. Thus, the present invention provides asymmetric insulators based on disulfides, wherein one of the arms being a longer alkyl chain (or other SAM forming species) and the other arm comprising a bulky group, such as a branched alkyl group, that can be polar or nonpolar) for creating the nanoconduits. Two exemplary species are shown in FIGS. 31A and 31B, with data shown in FIG. 31C. A variety of synthetic schemes are shown in FIG. 32. See also Mukaiyama Tetrahedron Lett. 1968, 5907; Boustany Tetrahedron Lett. 1970 3547; Harpp Tetrahedron Lett. 1970 3551; and Oae, J. Chem. Soc. Chem. Commun, 1977, 407, all of which are expressly incorporated herein by reference.

The length of the species making up the monolayer will vary as needed. As outlined above, it appears that hybridization is more efficient at a distance from the surface. The species to which nucleic acids are attached (as outlined below, these can be either insulators or conductive oligomers) may be basically the same length as the monolayer forming species or longer than them, resulting in the nucleic acids being more accessible to the solvent for hybridization. In some embodiments, the conductive oligomers to which the nucleic acids are attached may be shorter than the monolayer.

As will be appreciated by those in the art, the actual combinations and ratios of the different species making up the monolayer can vary widely, and will depend on whether mechanism-1 or -2 is used. Generally, three component systems are preferred for mechanism-2 systems, with the first species comprising a capture probe containing species, attached to the electrode via either an insulator or a conductive oligomer. The second species are conductive oligomers, and the third species are insulators. In this embodiment, the first species can comprise from about 90% to about 1%, with from about 20% to about 40% being preferred. For nucleic acids, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. To achieve these approximate proportions, preferred ratios of first:second:third species in SAM formation solvents are 2:2:1 for short targets, 1:3:1 for longer targets, with total thiol concentration (when used to attach these species, as is more fully outlined below) in the 500 µM to 1 mM range, and 833 µM being preferred.

Alternatively, two component systems can be used. In one embodiment, for use in either mechanism-1 or mechanism-2 systems, the two components are the first and second species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred. Alternatively, for mechanism-1 systems, the two components are the first and the third species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred.

In a preferred embodiment, the deposition of the SAM is done using aqueous solvents. As is generally described in Steel et al., Anal. Chem. 70:4670 (1998), Herne et al., J. Am. Chem. Soc. 119:8916 (1997), and Finklea, Electrochemistry of Organized Monolayers of Thiols and Related Molecules on Electrodes, from A. J. Bard, *Electroanalytical Chemistry: A Series of Advances*, Vol. 20, Dekker N.Y. 1966-, all of which are expressly incorporated by reference, the deposition of the SAM-forming species can be done out of aqueous solutions, frequently comprising salt.

The covalent attachment of the conductive oligomers and insulators may be accomplished in a variety of ways, depending on the electrode and the composition of the insulators and conductive oligomers used. In a preferred embodiment, the attachment linkers with covalently attached nucleosides or nucleic acids as depicted herein are covalently attached to an electrode. Thus, one end or terminus of the attachment linker is attached to the nucleoside or nucleic acid, and the other is attached to an electrode. In some embodiments it may be desirable to have the attachment linker attached at a position other than a terminus, or even to have a branched attachment linker that is attached to an electrode at one terminus and to two or more nucleosides at other termini, although this is not preferred. Similarly, the attachment linker may be attached at two sites to the electrode, as is generally depicted in Structures 11-13. Generally, some type of linker is used, as depicted below as "A" in Structure 10, where "X" is the conductive oligomer, "I" is an insulator and the hatched surface is the electrode:

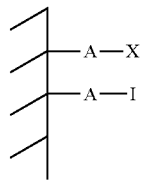

Structure 10

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the insulators and conductive oligomers may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 11, 12 and 13. As will be appreciated by those in the art, other such structures can be made. In Structures 11, 12 and 13, the A moiety is just a sulfur atom, but substituted sulfur moieties may also be used.

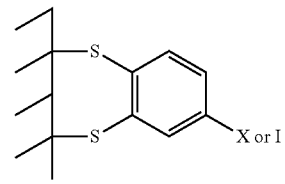

Structure 11

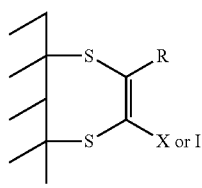

Structure 12

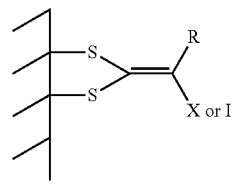

Structure 13

It should also be noted that similar to Structure 13, it may be possible to have a conductive oligomer terminating in a single carbon atom with three sulfur moieties attached to the electrode. Additionally, although not always depicted herein, the conductive oligomers and insulators may also comprise a "Q" terminal group.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 14, using the Structure 3 conductive oligomer, although as for all the structures depicted herein, any of the conductive oligomers, or combinations of conductive oligomers, may be used. Similarly, any of the conductive oligomers or insulators may also comprise terminal groups as described herein. Structure 14 depicts the "A" linker as comprising just a sulfur atom, although additional atoms may be present (i.e. linkers from the sulfur to the conductive oligomer or substitution groups). In addition, Structure 14 shows the sulfur atom attached to the Y aromatic group, but as will be appreciated by those in the art, it may be attached to the B-D group (i.e. an acetylene) as well.

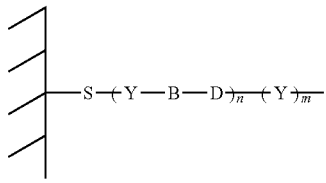

Structure 14

In a preferred embodiment, the electrode is a carbon electrode, i.e. a glassy carbon electrode, and attachment is via a nitrogen of an amine group. A representative structure is depicted in Structure 15. Again, additional atoms may be present, i.e. Z type linkers and/or terminal groups.

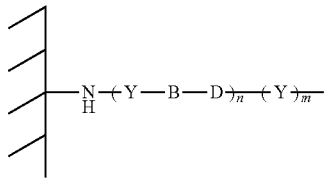

Structure 15

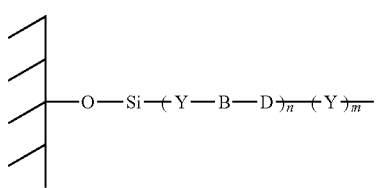

Structure 16

In Structure 16, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

The SAMs of the invention can be made in a variety of ways, including deposition out of organic solutions and deposition out of aqueous solutions. The methods outlined herein use a gold electrode as the example, although as will be appreciated by those in the art, other metals and methods may be used as well. In one preferred embodiment, indium-tin-oxide (ITO) is used as the electrode.

In a preferred embodiment, a gold surface is first cleaned. A variety of cleaning procedures may be employed, including, but not limited to, chemical cleaning or etchants (including Piranha solution (hydrogen peroxide/sulfuric acid) or aqua regia (hydrochloric acid/nitric acid), electrochemical methods, flame treatment, plasma treatment or combinations thereof.

Following cleaning, the gold substrate is exposed to the SAM species. When the electrode is ITO, the SAM species are phosphonate-containing species. This can also be done in a variety of ways, including, but not limited to, solution deposition, gas phase deposition, microcontact printing, spray deposition, deposition using neat components, etc. A preferred embodiment utilizes a deposition solution comprising a mixture of various SAM species in solution, generally thiol-containing species. Mixed monolayers that contain nucleic acids are usually prepared using a two step procedure. The thiolated nucleic acid is deposited during the first deposition step (generally in the presence of at least one other monolayer-forming species) and the mixed monolayer formation is completed during the second step in which a second thiol solution minus nucleic acid is added. The second step frequently involves mild heating to promote monolayer reorganization.

In a preferred embodiment, the deposition solution is an organic deposition solution. In this embodiment, a clean gold surface is placed into a clean vial. A binding ligand deposition solution in organic solvent is prepared in which the total thiol concentration is between micromolar to saturation; preferred ranges include from about 1 μM to 10 mM, with from about 400 uM to about 1.0 mM being especially preferred. In a preferred embodiment, the deposition solution contains thiol modified DNA (i.e. nucleic acid attached to an attachment linker) and thiol diluent molecules (either conductive oligomers or insulators, with the latter being preferred). The ratio of nucleic acid to diluent (if present) is usually between 1000:1 to 1:1000, with from about 10:1 to about 1:10 being preferred and 1:1 being especially preferred. The preferred solvents are tetrahydrofuran (THF), acetonitrile, dimethylformamide (DMF), ethanol, or mixtures thereof; generally any solvent of sufficient polarity to dissolve the capture ligand can be used, as long as the solvent is devoid of functional groups that will react with the surface. Sufficient nucleic acid deposition solution is added to the vial so as to completely cover the electrode surface. The gold substrate is allowed to incubate at ambient temperature or slightly above ambient temperature for a period of time ranging from seconds to hours, with 5-30 minutes being preferred. After the initial incubation, the deposition solution is removed and a solution of diluent molecule only (from about 1 μM to 10 mM, with from about 100 uM to about 1.0 mM being preferred) in organic solvent is added. The gold substrate is allowed to incubate at room temperature or above room temperature for a period of time (seconds to days, with from about 10 minutes to about 24 hours being preferred). The gold sample is removed from the solution, rinsed in clean solvent and used.

In a preferred embodiment, an aqueous deposition solution is used. As above, a clean gold surface is placed into a clean vial. A nucleic acid deposition solution in water is prepared in which the total thiol concentration is between about 1 uM and 10 mM, with from about 1 μM to about 200 uM being preferred. The aqueous solution frequently has salt present (up to saturation, with approximately 1M being preferred), however pure water can be used. The deposition solution contains thiol modified nucleic acid and often a thiol diluent molecule. The ratio of nucleic acid to diluent is usually between between 1000:1 to 1:1000, with from about 10:1 to about 1:10 being preferred and 1:1 being especially preferred. The nucleic acid deposition solution is added to the vial in such a volume so as to completely cover the electrode surface. The gold substrate is allowed to incubate at ambient temperature or slightly above ambient temperature for 1-30 minutes with 5 minutes usually being sufficient. After the initial incubation, the deposition solution is removed and a solution of diluent molecule only (10 uM-1.0 mM) in either water or organic solvent is added. The gold substrate is allowed to incubate at room temperature or above room temperature until a complete monolayer is formed (10 minutes-24 hours). The gold sample is removed from the solution, rinsed in clean solvent and used.

In a preferred embodiment, the deposition solution comprises a zwitterionic compound, preferably betaine. Preferred embodiments utilize betain and Tris-HCl buffers.

In a preferred embodiment, as outlined herein, a circuit board is used as the substrate for the gold electrodes. Formation of the SAMs on the gold surface is generally done by first cleaning the boards, for example in a 10% sulfuric acid solution for 30 seconds, detergent solutions, aqua regia, plasma, etc., as outlined herein. Following the sulfuric acid treatment, the boards are washed, for example via immersion in two Milli-Q water baths for 1 minute each. The boards are then dried, for example under a stream of nitrogen. Spotting of the deposition solution onto the boards is done using any number of known spotting systems, generally by placing the boards on an X-Y table, preferably in a humidity chamber. The size of the spotting drop will vary with the size of the electrodes on the boards and the equipment used for delivery of the solution; for example, for 250 µM size electrodes, a 30 nanoliter drop is used. The volume should be sufficient to cover the electrode surface completely. The drop is incubated at room temperature for a period of time (sec to overnight, with 5 minutes preferred) and then the drop is removed by rinsing in a Milli-Q water bath. The boards are then preferably treated with a second deposition solution, generally comprising insulator in organic solvent, preferably acetonitrile, by immersion in a 45° C. bath. After 30 minutes, the boards are removed and immersed in an acetonitrile bath for 30 seconds followed by a milli-Q water bath for 30 seconds. The boards are dried under a stream of nitrogen.

In a preferred embodiment, the electrode comprising the monolayer including conductive oligomers further comprises a nucleic acid capture probe. The capture probe nucleic acid is covalently attached to the electrode. This attachment can be via a conductive oligomer or via an insulator. By "capture probe" or "anchor probe" herein is meant a component of an assay complex as defined herein that allows the attachment of a target sequence to the electrode, for the purposes of detection. As is more fully outlined below, attachment of the target sequence to the capture probe may be direct (i.e. the target sequence hybridizes to the capture probe) or indirect (one or more capture extender probes are used). By "covalently attached" herein is meant that two moieties are attached by at least one bond, including sigma bonds, pi bonds and coordination bonds. In addition, as is more fully outlined below, the capture probes may have both nucleic and non-nucleic acid portions. Thus, for example, flexible linkers such as alkyl groups, including polyethylene glycol linkers, may be used to get the nucleic acid portion of the capture probe off the electrode surface. This may be particularly useful when the target sequences are large, for example when genomic DNA or rRNA is the target.

The capture probe nucleic acid is covalently attached to the electrode, via an "attachment linker", that can be either a conductive oligomer or via an insulator. Thus, one end of the attachment linker is attached to a nucleic acid, and the other end (although as will be appreciated by those in the art, it need not be the exact terminus for either) is attached to the electrode. Thus, any of structures depicted herein may further comprise a nucleic acid effectively as a terminal group. Thus, the present invention provides compositions comprising nucleic acids covalently attached to electrodes as is generally depicted below in Structure 17:

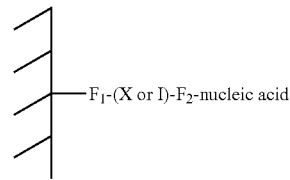

Structure 17

In Structure 17, the hatched marks on the left represent an electrode. X is a conductive oligomer and I is an insulator as defined herein. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator to the nucleic acid, and may be a bond, an atom or a linkage as is herein described. $F_2$ may be part of the conductive oligomer, part of the insulator, part of the nucleic acid, or exogeneous to both, for example, as defined herein for "Z".

In a preferred embodiment, the capture probe nucleic acid is covalently attached to the electrode via a conductive oligomer. The covalent attachment of the nucleic acid and the conductive oligomer may be accomplished in several ways. In a preferred embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occurring nucleic acids, although as will be appreciated by those in the art, similar techniques may be used with nucleic acid analogs.

In a preferred embodiment, the conductive oligomer is attached to the base of a nucleoside of the nucleic acid. This may be done in several ways, depending on the oligomer, as is described below. In one embodiment, the oligomer is attached to a terminal nucleoside, i.e. either the 3' or 5' nucleoside of the nucleic acid. Alternatively, the conductive oligomer is attached to an internal nucleoside.

The point of attachment to the base will vary with the base. Generally, attachment at any position is possible. In some embodiments, for example when the probe containing the ETMs may be used for hybridization, it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the conductive oligomer and the base. In this embodiment, for example, conductive oligomers with terminal acetylene bonds are attached directly to the base. Structure 18 is an example of this linkage, using a Structure 3 conductive oligomer and uridine as the base, although other bases and conductive oligomers can be used as will be appreciated by those in the art:

Structure 18

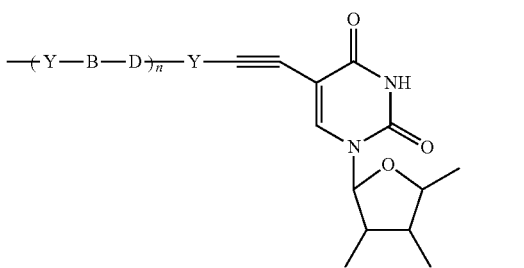

It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting groups, at any position, for example as needed during synthesis.

In addition, the base may contain additional modifications as needed, i.e. the carbonyl or amine groups may be altered or protected, for example as is depicted in FIG. 18A of PCT US97/20014. This may be required to prevent significant dimerization of conductive oligomers instead of coupling to the iodinating base. In addition, changing the components of the palladium reaction may be desirable also. R groups may be preferred on longer conductive oligomers to increase solubility.

In an alternative embodiment, the attachment is any number of different Z linkers, including amide and amine linkages, as is generally depicted in Structure 19 using uridine as the base and a Structure 3 oligomer:

Structure 19:

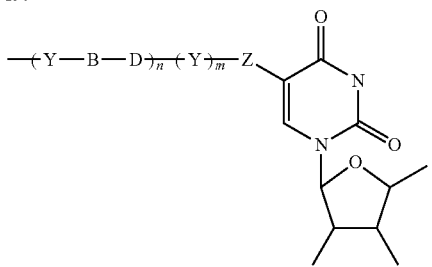

In this embodiment, Z is a linker. Preferably, Z is a short linker of about 1 to about 10 atoms, with from 1 to 5 atoms being preferred, that may or may not contain alkene, alkynyl, amine, amide, azo, imine, etc., bonds. Linkers are known in the art; for example, homo- or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the conductive oligomer is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the conductive oligomer is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Org. Chem. 36(2):250 (1971); McGee et al., J. Org. Chem. 61:781-785 (1996); Mikhailopulo et al., Liebigs. Ann. Chem. 513-519 (1993); McGee et al., Nucleosides & Nucleotides 14(6):1329 (1995), all of which are incorporated by reference). These modified nucleosides are then used to add the conductive oligomers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 1-3 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 20 (using the Structure 3 conductive oligomer):

Structure 20

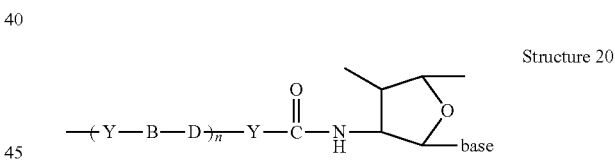

As will be appreciated by those in the art, Structure 20 has the terminal bond fixed as an amide bond.

In a preferred embodiment, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 3 conductive oligomer is used. Thus, for example, Structures 21 and 22 depict nucleosides with the Structures 3 and 9 conductive oligomers, respectively, using the nitrogen as the heteroatom, although other heteroatoms can be used:

Structure 21

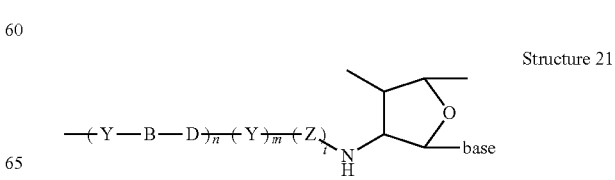

In Structure 21, preferably both m and t are not zero. A preferred Z here is a methylene group, or other aliphatic alkyl linkers. One, two or three carbons in this position are particularly useful for synthetic reasons; see PCT US97120014.

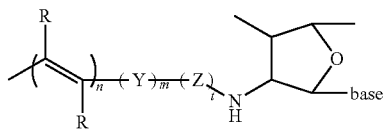

Structure 22

In Structure 22, Z is as defined above. Suitable linkers include methylene and ethylene.

In an alternative embodiment, the conductive oligomer is covalently attached to the nucleic acid via the phosphate of the ribose-phosphate backbone (or analog) of a nucleic acid. In this embodiment, the attachment is direct, utilizes a linker or via an amide bond. Structure 23 depicts a direct linkage, and Structure 24 depicts linkage via an amide bond (both utilize the Structure 3 conductive oligomer, although Structure 8 conductive oligomers are also possible). Structures 23 and 24 depict the conductive oligomer in the 3' position, although the 5' position is also possible. Furthermore, both Structures 23 and 24 depict naturally occurring phosphodiester bonds, although as those in the art will appreciate, nonstandard analogs of phosphodiester bonds may also be used.

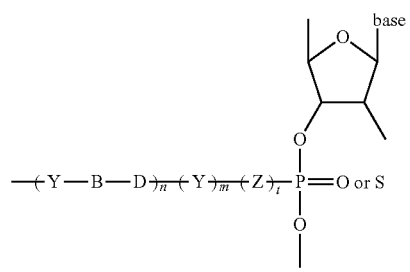

Structure 23

In Structure 23, if the terminal Y is present (i.e. m=1), then preferably Z is not present (i.e. t=0). If the terminal Y is not present, then Z is preferably present.

Structure 24 depicts a preferred embodiment, wherein the terminal B-D bond is an amide bond, the terminal Y is not present, and Z is a linker, as defined herein.

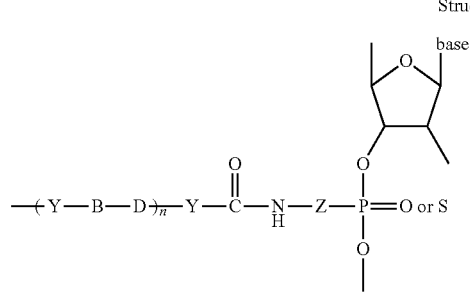

Structure 24

In a preferred embodiment, the conductive oligomer is covalently attached to the nucleic acid via a transition metal ligand. In this embodiment, the conductive oligomer is covalently attached to a ligand which provides one or more of the coordination atoms for a transition metal. In one embodiment, the ligand to which the conductive oligomer is attached also has the nucleic acid attached, as is generally depicted below in Structure 25. Alternatively, the conductive oligomer is attached to one ligand, and the nucleic acid is attached to another ligand, as is generally depicted below in Structure 26. Thus, in the presence of the transition metal, the conductive oligomer is covalently attached to the nucleic acid. Both of these structures depict Structure 3 conductive oligomers, although other oligomers may be utilized. Structures 25 and 26 depict two representative structures:

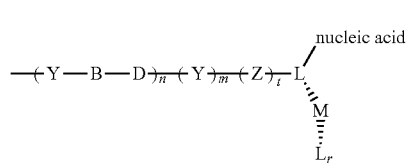

Structure 25

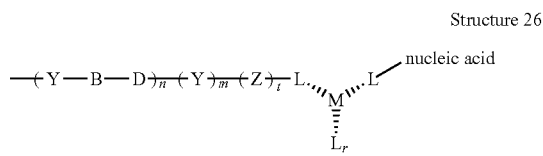

Structure 26

In the structures depicted herein, M is a metal atom, with transition metals being preferred. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron.

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ)

donors) and organometallic ligands such as metallocene ligands (generally referred to in the literature as pi (n) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c] phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetraazacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with n-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis(cyclopentadieyl) metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene $[(C_5H_5)_2Fe]$ and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic n-bonded ligands such as the allyl(−1) ion, or butadiene yield potentially suitable organometallic compounds, and all such ligands, in conjunction with other π-bonded and 6-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture. These combinations are depicted in representative structures using the conductive oligomer of Structure 3 are depicted in Structures 27 (using phenanthroline and amino as representative ligands), 28 (using ferrocene as the metal-ligand combination) and 29 (using cyclopentadienyl and amino as representative ligands).

Structure 27

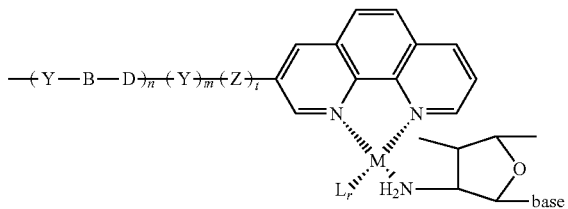

Structure 28

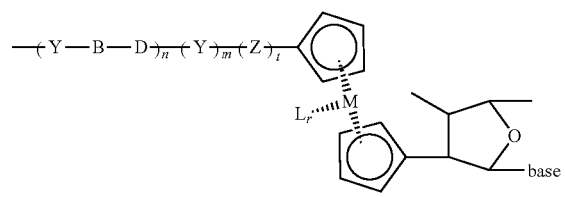

Structure 29

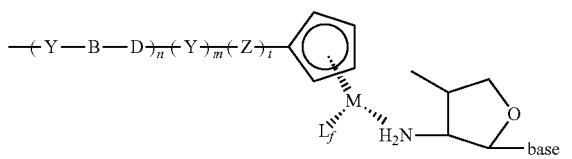

In addition to serving as attachments for conductive oligomers and electrodes, the above compositions can also be used as ETM labels. That is, as is outlined in FIGS. 19 and 20, transition metals (or other ETMs) attached to conductive oligomers can be added to the nucleic acids for detection. In this embodiment, without being bound by theory, the conductive oligomer, terminating preferably in an F1 linkage (a linkage that allows the attachment of the conductive oligomer to the surface), will penetrate the SAM and facilitate electron transfer between the ETM and the electrode. Without being bound by theory, this appears to allow rapid electron transfer, similar to a "mechanism-1" system, by providing a direct pathway for electrons; this is sometimes referred to herein as "hardwiring".

Surprisingly, as outlined in Example 3, the system appears to work whether or not the F1 moiety is protected; that is, a direct attachment may not be required to increase the frequency response of the ETM. Thus, the conductive oligomer can terminate either in an F1 moiety, an F1 moiety protected with a protecting group (see Greene, supra), or need not terminate in an F1 moiety at all; terminal groups such as are used on the surfaces of the SAMs may also be used. Alternatively, the bare terminus of the conductive oligomer may be sufficient.

In this embodiment, a plurality of ETMs per "branch" may be used. They may be attached as a group, e.g. as a metallocene polymer, terminating in the conductive oligomer, or may be substitution groups off of the conductive oligomer. In general, preferred embodiments utilize electronic conjugation between the ETMs and the conductive oligomer, to facilitate electron transfer.

In general, the length of the conductive oligomer in this embodiment will vary with the length of the SAM on the electrode, and preferred embodiments utilize two unit and three unit oligomers. Preferred conductive oligomers in this embodiment are the same as those outlined above for attachment of nucleic acids to electrodes, with phenyl-acetylene oligomers being the most preferred.

In this embodiment, the ETM with the attached conductive oligomer is generally synthesized, and then a phosphoramidite moiety is made, as is generally depicted in FIG. 20 of U.S. Ser. No. 60/145,912, filed Jul. 27, 1999, hereby expressly incorporated by reference.

In a preferred embodiment, the ligands used in the invention show altered fluorescent properties depending on the redox state of the chelated metal ion. As described below, this thus serves as an additional mode of detection of electron transfer between the ETM and the electrode.

In a preferred embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other preferred ligands include cyclopentadiene and phenanthroline.

The use of metal ions to connect the nucleic acids can serve as an internal control or calibration of the system, to evaluate the number of available nucleic acids on the surface. However, as will be appreciated by those in the art, if metal ions are used to connect the nucleic acids to the conductive oligomers, it is generally desirable to have this metal ion complex have a different redox potential than that of the ETMs used in the rest of the system, as described below. This is generally true so as to be able to distinguish the presence of the capture probe from the presence of the target sequence. This may be useful for identification, calibration and/or quantification. Thus, the amount of capture probe on an electrode may be compared to the amount of hybridized double stranded nucleic acid to quantify the amount of target sequence in a sample. This is quite significant to serve as an internal control of the sensor or system. This allows a measurement either prior to the addition of target or after, on the same molecules that will be used for detection, rather than rely on a similar but different control system. Thus, the actual molecules that will be used for the detection can be quantified prior to any experiment. This is a significant advantage over prior methods.

In a preferred embodiment, the capture probe nucleic acids are covalently attached to the electrode via an insulator. The attachment of nucleic acids to insulators such as alkyl groups is well known, and can be done to the base or the backbone, including the ribose or phosphate for backbones containing these moieties, or to alternate backbones for nucleic acid analogs.

In a preferred embodiment, there may be one or more different capture probe species on the surface, as is generally depicted in the Figures. In some embodiments, there may be one type of capture probe, or one type of capture probe extender, as is more fully described below. Alternatively, different capture probes, or one capture probes with a multiplicity of different capture extender probes can be used. Similarly, it may be desirable to use auxiliary capture probes that comprise relatively short probe sequences, that can be used to "tack down" components of the system, for example the recruitment linkers, to increase the concentration of ETMs at the surface.

Thus the present invention provides electrodes comprising monolayers comprising conductive oligomers and capture probes, useful in nucleic acid detection systems. In a preferred embodiment, the compositions further comprise a label probe. The label probe is nucleic acid, generally single stranded, although as more fully outlined below, it may contain double-stranded portions. The label probe comprises a first portion that is capable of hybridizing to a component of the assay complex, defined below, and a second portion that does not hybridize to a component of an assay complex and comprises at least one covalently attached ETM.

Thus, label probes with covalently attached ETMs are provided. The terms "electron donor moiety", "electron acceptor moiety", and "ETMs" (ETMs) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention are listed above.

The transition metals are complexed with a variety of ligands, L, defined above, to form suitable transition metal complexes, as is well known in the art.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2,1,9-def:6,5,10-d'e'f')diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis (dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and substituted derivatives of these compounds.

In one embodiment, the electron donors and acceptors are redox proteins as are known in the art. However, redox proteins in many embodiments are not preferred.

The choice of the specific ETMs will be influenced by the type of electron transfer detection used, as is generally outlined below. Preferred ETMs are metallocenes, with ferrocene being particularly preferred.

Without being bound by theory, it appears that in "mechanism-2" systems, electron transfer is facilitated when the ETM is able to penetrate ("snuggle") into the monolayer to some degree. That is, in general, it appears that hydrophobic ETMs used with hydrophobic SAMs give rise to better (greater) signals than ETMs that are charged or more hydrophilic. Thus, for example, ferrocene in solution can penetrate the monolayers of the examples and give a signal when electroconduits are present, while ferrocyanide in solution gives little or no signal. Thus, in general, hydrophobic ETMs are preferred in mechanism-2 systems; however, transition metal complexes, although charged, with one or more hydrophobic ligands, such as Ru and Os complexes, also give rise to good signals. Similarly, electron transfer between the ETM and the electrode is facilitated by the use of linkers or spacers that allow the ETM some flexibility to penetrate into the monolayer; thus the N6 compositions of the invention have a four carbon linker attaching the ETM to the nucleic acid. In addition, as outlined herein, the choice of the ETM/monolayer pair can be exploited during genotyping.

In a preferred embodiment, a plurality of ETMs are used. As is shown in the examples, the use of multiple ETMs provides signal amplification and thus allows more sensitive detection limits. As discussed below, while the use of multiple ETMs on nucleic acids that hybridize to complementary strands can cause decreases in $T_m$s of the hybridization complexes depending on the number, site of attachment and spacing between the multiple ETMs, this is not a factor when the ETMs are on the recruitment linker, since this does not hybridize to a complementary sequence. Accordingly, pluralities of ETMs are preferred, with at least about 2 ETMs per recruitment linker being preferred, and at least about 10 being particularly preferred, and at least about 20 to 50 being especially preferred. In some instances, very large numbers of ETMs (100 to 1000) can be used.

As will be appreciated by those in the art, the portion of the label probe (or target, in some embodiments) that comprises the ETMs (termed herein a "recruitment linker" or "signal carrier") can be nucleic acid, or it can be a non-nucleic acid linker that links the first hybridizable portion of the label probe to the ETMs. That is, since this portion of the label probe is not required for hybridization, it need not be nucleic acid, although this may be done for ease of synthesis. In some embodiments, as is more fully outlined below, the recruitment linker may comprise double-stranded portions. Thus, as will be appreciated by those in the art, there are a variety of configurations that can be used. In a preferred embodiment, the recruitment linker is nucleic acid (including analogs), and attachment of the ETMs can be via (1) a base; (2) the backbone, including the ribose, the phosphate, or comparable structures in nucleic acid analogs; (3) nucleoside replacement, described below; or (4) metallocene polymers, as described below. In a preferred embodiment, the recruitment linker is non-nucleic acid, and can be either a metallocene polymer or an alkyl-type polymer (including heteroalkyl, as is more fully described below) containing ETM substitution groups. These options are generally depicted in the Figures.

In a preferred embodiment, the recruitment linker is a nucleic acid, and comprises covalently attached ETMs. The ETMs may be attached to nucleosides within the nucleic acid in a variety of positions. Preferred embodiments include, but are not limited to, (1) attachment to the base of the nucleoside, (2) attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers, with the latter being preferred.

In addition, as is described below, when the recruitment linker is nucleic acid, it may be desirable to use secondary label probes, that have a first portion that will hybridize to a portion of the primary label probes and a second portion comprising a recruitment linker as is defined herein. This is generally depicted in FIG. 16H; this is similar to the use of an amplifier probe, except that both the primary and the secondary label probes comprise ETMs.

In a preferred embodiment, the ETM is attached to the base of a nucleoside as is generally outlined above for attachment of the conductive oligomer. Attachment can be to an internal nucleoside or a terminal nucleoside.

The covalent attachment to the base will depend in part on the ETM chosen, but in general is similar to the attachment of conductive oligomers to bases, as outlined above. Attachment may generally be done to any position of the base. In a preferred embodiment, the ETM is a transition metal complex, and thus attachment of a suitable metal ligand to the base leads to the covalent attachment of the ETM. Alternatively, similar types of linkages may be used for the attachment of organic ETMs, as will be appreciated by those in the art.

In one embodiment, the C4 attached amino group of cytosine, the C6 attached amino group of adenine, or the C2 attached amino group of guanine may be used as a transition metal ligand.

Ligands containing aromatic groups can be attached via acetylene linkages as is known in the art (see Comprehensive Organic Synthesis, Trost et al., Ed., Pergamon Press, Chapter 2.4: Coupling Reactions *Between* $sp^2$ and sp Carbon Centers, Sonogashira, pp 521-549, and pp 950-953, hereby incorporated by reference). Structure 30 depicts a representative structure in the presence of the metal ion and any other necessary ligands; Structure 30 depicts uridine, although as for all the structures herein, any other base may also be used.

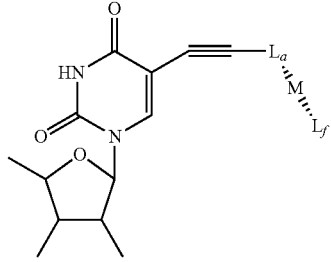

Structure 30

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. $L_r$ and M are as defined above. Again, it will be appreciated by those in the art, a linker ("Z") may be included between the nucleoside and the ETM.

Similarly, as for the conductive oligomers, the linkage may be done using a linker, which may utilize an amide linkage (see generally Telser et al., J. Am. Chem. Soc. 111:7221-7226 (1989); Telser et al., J. Am. Chem. Soc. 111:7226-7232 (1989), both of which are expressly incorporated by reference). These structures are generally depicted below in Structure 31, which again uses uridine as the base, although as above, the other bases may also be used:

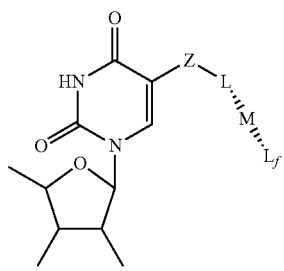

Structure 31

In this embodiment, L is a ligand as defined above, with $L_r$ and M as defined above as well. Preferably, L is amino, phen, byp and terpy.

In a preferred embodiment, the ETM attached to a nucleoside is a metallocene; i.e. the L and L, of Structure 31 are both metallocene ligands, $L_m$, as described above. Structure 32 depicts a preferred embodiment wherein the metallocene is ferrocene, and the base is uridine, although other bases may be used:

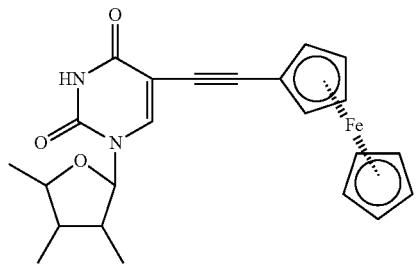

Structure 32

Preliminary data suggest that Structure 32 may cyclize, with the second acetylene carbon atom attacking the carbonyl oxygen, forming a furan-like structure. Preferred metallocenes include ferrocene, cobaltocene and osmiumocene.

In a preferred embodiment, the ETM is attached to a ribose at any position of the ribose-phosphate backbone of the nucleic acid, i.e. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the ETM. Preferred embodiments utilize attachment at the 2' or 3' position of the ribose, with the 2' position being preferred. Thus for example, the conductive oligomers depicted in Structure 13, 14 and 15 may be replaced by ETMs; alternatively, the ETMs may be added to the free terminus of the conductive oligomer.

In a preferred embodiment, a metallocene serves as the ETM, and is attached via an amide bond as depicted below in Structure 33. The examples outline the synthesis of a preferred compound when the metallocene is ferrocene.

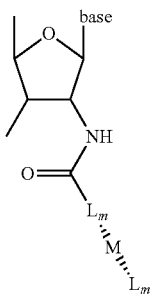

Structure 33

In a preferred embodiment, amine linkages are used, as is generally depicted in Structure 34.

Structure 34

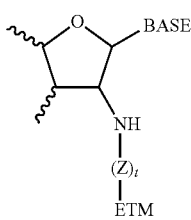

Z is a linker, as defined herein, with 1-16 atoms being preferred, and 2-4 atoms being particularly preferred, and t is either one or zero.

In a preferred embodiment, oxo linkages are used, as is generally depicted in Structure 35.

Structure 35

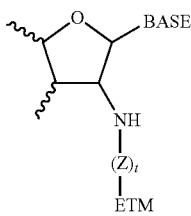

In Structure 35, Z is a linker, as defined herein, and t is either one or zero. Preferred Z linkers include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

Linkages utilizing other heteroatoms are also possible.

In a preferred embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (i.e. nitrogen) serves as a transition metal ligand (see PCT publication WO 95/15971, incorporated by reference). Alternatively, the conductive oligomers depicted in Structures 23 and 24 may be replaced by ETMs. In a preferred embodiment, the composition has the structure shown in Structure 36.

Structure 36

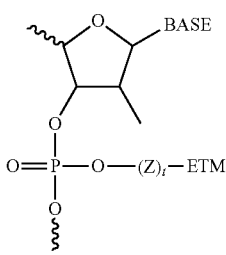

In Structure 361, the ETM is attached via a phosphate linkage, generally through the use of a linker, Z. Preferred Z linkers include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred.

When the ETM is attached to the base or the backbone of the nucleoside, it is possible to attach the ETMs via "dendrimer" structures, as is more fully outlined below. As is generally depicted in the Figures, alkyl-based linkers can be used to create multiple branching structures comprising one or more ETMs at the terminus of each branch (although internal ETMs can be used as well). Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions. The branch point can be an internal one or a terminal one, and can be a chemical branch point or a nucleoside branch point.

In a preferred embodiment, an ETM such as a metallocene is used as a "nucleoside replacement", serving as an ETM. For example, the distance between the two cyclopentadiene rings of ferrocene is similar to the orthogonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 37 (nucleic acid with a ribose-phosphate backbone) and Structure 38 (peptide nucleic acid backbone). Structures 37 and 38 depict ferrocene, although as will be appreciated by those in the art, other metallocenes may be used as well. In general, air stable metallocenes are preferred, including metallocenes utilizing ruthenium and cobalt as the metal.

Structure 37

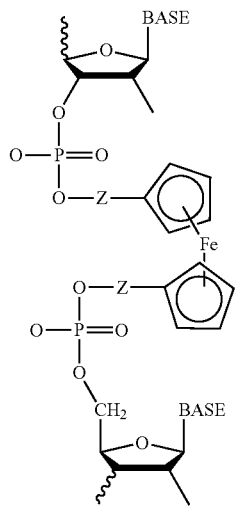

In Structure 37, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 37 depicts a ribose-phosphate backbone, although as will be appreciated by those in the art, nucleic acid analogs may also be used, including ribose analogs and phosphate bond analogs.

Structure 38

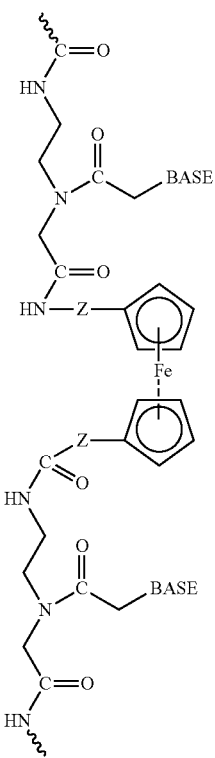

In Structure 38, preferred Z groups are as listed above, and again, each Z linker can be the same or different. As above, other nucleic acid analogs may be used as well.

In addition, although the structures and discussion above depicts metallocenes, and particularly ferrocene, this same general idea can be used to add ETMs in addition to metallocenes, as nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Particularly preferred in this embodiment are complexes comprising at least two ring (for example, aryl and substituted aryl) ligands, where each of the ligands comprises functional groups for attachment via phosphoramidite chemistry. As will be appreciated by those in the art, this type of reaction, creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

Thus, by inserting a metallocene such as ferrocene (or other ETM) into the backbone of a nucleic acid, nucleic acid analogs are made; that is, the invention provides nucleic acids having a backbone comprising at least one metallocene. This is distinguished from nucleic acids having metallocenes attached to the backbone, i.e. via a ribose, a phosphate, etc. That is, two nucleic acids each made up of a traditional nucleic acid or analog (nucleic acids in this case including a single nucleoside), may be covalently attached to each other via a metallocene. Viewed differently, a metallocene derivative or substituted metallocene is provided, wherein each of the two aromatic rings of the metallocene has a nucleic acid substitutent group.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers"; that is, there are areas of metallocene polymers within the backbone.

In addition to the nucleic acid substitutent groups, it is also desirable in some instances to add additional substitutent groups to one or both of the aromatic rings of the metallocene (or ETM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substitutent groups include, but are not limited to, amide groups, amine groups, carboxylic acids, and alcohols, including substituted alcohols. In addition, these substitutent groups can be attached via linkers as well, although in general this is not preferred.

In addition, substituent groups on an ETM, particularly metallocenes such as ferrocene, may be added to alter the redox properties of the ETM. Thus, for example, in some embodiments, as is more fully described below, it may be desirable to have different ETMs attached in different ways (i.e. base or ribose attachment), on different probes, or for different purposes (for example, calibration or as an internal standard). Thus, the addition of substitutent groups on the metallocene may allow two different ETMs to be distinguished.

In order to generate these metallocene-backbone nucleic acid analogs, the intermediate components are also provided. Thus, in a preferred embodiment, the invention provides phosphoramidite metallocenes, as generally depicted in Structure 39:

Structure 39

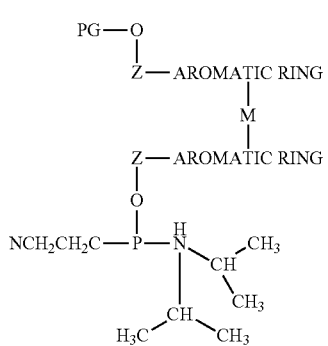

In Structure 39, PG is a protecting group, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein. Structure 40 depicts the ferrocene derivative:

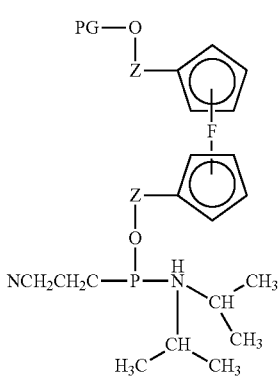

Structure 40

These phosphoramidite analogs can be added to standard oligonucleotide syntheses as is known in the art.

Structure 41 depicts the ferrocene peptide nucleic acid (PNA) monomer, that can be added to PNA synthesis as is known in the art and depicted within the Figures and Examples:

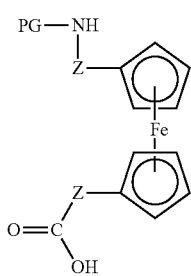

Structure 41

In Structure 41, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In a preferred embodiment, the ETMs are attached as polymers, for example as metallocene polymers, in a "branched" configuration similar to the "branched DNA" embodiments herein and as outlined in U.S. Pat. No. 5,124,246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in structures 39 and 40, ETMs, such as metallocene ETMs, are added. Additional phosphoramidite ETMs such as metallocenes can be added, to form "ETM polymers", including "metallocene polymers" as depicted herein, particularly for ferrocene. In addition, in some embodiments, it is desirable to increase the solubility of the polymers by adding a "capping" group to the terminal ETM in the polymer, for example a final phosphate group to the metallocene as is generally depicted in FIGS. 12A and 12B. Other suitable solubility enhancing "capping" groups will be appreciated by those in the art. It should be noted that these solubility enhancing groups can be added to the polymers in other places, including to the ligand rings, for example on the metallocenes as discussed herein A preferred embodiment of this general idea is outlined in the Figures. In this embodiment, the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a griming nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 41, peptide nucleic acid structures containing metallocene polymers could be generated.

Thus, the present invention provides recruitment linkers of nucleic acids comprising "branches" of metallocene polymers as is generally depicted in FIGS. 12 and 13. Preferred embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done.

In a preferred embodiment, the recruitment linker is not nucleic acid, and instead may be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contain functional groups for the covalent attachment of ETMs. In some embodiments coupling moieties are used to covalently link the subunits with the ETMs. Preferred functional groups for attachment are amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo- or hetero-bifunctional linkers as are well known (see 1994 Pierce Chemical Company catalog, technical section on cross-linkers, pages 155-200, incorporated herein by reference).

Suitable recruitment polymers include, but are not limited to, functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In a preferred embodiment, the recruitment linker comprises a metallocene polymer, as is described above.

The attachment of the recruitment linkers to the first portion of the label probe will depend on the composition of the recruitment linker, as will be appreciated by those in the art. When the recruitment linker is nucleic acid, it is generally formed during the synthesis of the first portion of the label probe, with incorporation of nucleosides containing ETMs as required. Alternatively, the first portion of the label probe and the recruitment linker may be made separately, and then attached. For example, there may be an overlapping section of complementarity, forming a section of double stranded nucleic acid that can then be chemically crosslinked, for example by using psoralen as is known in the art.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (i.e. nucleic acid segments linked together with alkyl linkers) or in branched forms (nucleic acids with alkyl "branches" that may contain ETMs and may be additionally branched).

In a preferred embodiment, it is the target sequence itself that carries the ETMs, rather than the recruitment linker of a label probe. For example, as is more fully described below, it is possible to enzymatically add triphosphate nucleotides comprising the ETMs of the invention to a growing nucleic acid, for example during a polymerase chain reaction (PCR). As will be recognized by those in the art, while several enzymes have been shown to generally tolerate modified nucleotides, some of the modified nucleotides of the invention, for example the "nucleoside replacement" embodiments and putatively some of the phosphate attachments, may or may not be recognized by the enzymes to allow incorporation into a growing nucleic acid. Therefore, preferred attachments in this embodiment are to the base or ribose of the nucleotide.

Thus, for example, PCR amplification of a target sequence, as is well known in the art, will result in target sequences comprising ETMs, generally randomly incorporated into the sequence. The system of the invention can then be configured to allow detection using these ETMs, as is generally depicted in FIGS. 16A, 16B and 16D.

Alternatively, as outlined more fully below, it is possible to enzymatically add nucleotides comprising ETMs to the terminus of a nucleic acid, for example a target nucleic acid. In this embodiment, an effective "recruitment linker" is added to the terminus of the target sequence, that can then be used for detection. Thus the invention provides compositions utilizing electrodes comprising monolayers of conductive oligomers and capture probes, and target sequences that comprises a first portion that is capable of hybridizing to a component of an assay complex, and a second portion that does not hybridize to a component of an assay complex and comprises at least one covalently attached electron transfer moiety. Similarly, methods utilizing these compositions are also provided.

It is also possible to have ETMs connected to probe sequences, i.e. sequences designed to hybridize to complementary sequences. Thus, ETMs may be added to non-recruitment linkers as well. For example, there may be ETMs added to sections of label probes that do hybridize to components of the assay complex, for example the first portion, or to the target sequence as outlined above. These ETMs may be used for electron transfer detection in some embodiments, or they may not, depending on the location and system. For example, in some embodiments, when for example the target sequence containing randomly incorporated ETMs is hybridized directly to the capture probe, as is depicted in FIG. 16A, there may be ETMs in the portion hybridizing to the capture probe. If the capture probe is attached to the electrode using a conductive oligomer, these ETMs can be used to detect electron transfer as has been previously described. Alternatively, these ETMs may not be specifically detected.

Similarly, in some embodiments, when the recruitment linker is nucleic acid, it may be desirable in some instances to have some or all of the recruitment linker be double stranded. In one embodiment, there may be a second recruitment linker, substantially complementary to the first recruitment linker, that can hybridize to the first recruitment linker. In a preferred embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, i.e. the $T_m$ may be decreased, depending on the site of attachment and the characteristics of the ETM. Thus, in general, when multiple ETMs are used on hybridizing strands, generally there are less than about 5, with less than about 3 being preferred, or alternatively the ETMs should be spaced sufficiently far apart that the intervening nucleotides can sufficiently hybridize to allow good kinetics.

In one embodiment, non-covalently attached ETMs may be used. In one embodiment, the ETM is a hybridization indicator. Hybridization indicators serve as an ETM that will preferentially associate with double stranded nucleic acid is added, usually reversibly, similar to the method of Millan et al., Anal. Chem. 65:2317-2323 (1993); Millan et al., Anal. Chem. 662943-2948 (1994), both of which are hereby expressly incorporated by reference. In this embodiment, increases in the local concentration of ETMs, due to the association of the ETM hybridization indicator with double stranded nucleic acid at the surface, can be monitored using the monolayers comprising the conductive oligomers.

Hybridization indicators include intercalators and minor and/or major groove binding moieties. In a preferred embodiment, intercalators may be used; since intercalation generally only occurs in the presence of double stranded nucleic acid, only in the presence of double stranded nucleic acid will the ETMs concentrate. Intercalating transition metal complex ETMs are known in the art. Similarly, major or minor groove binding moieties, such as methylene blue, may also be used in this embodiment.

Similarly, the systems of the invention may utilize non-covalently attached ETMs, as is generally described in Napier et al., Bioconj. Chem. 8:906 (1997), hereby expressly incorporated by reference. In this embodiment, changes in the redox state of certain molecules as a result of the presence of DNA (i.e. guanine oxidation by ruthenium complexes) can be detected using the SAMs comprising conductive oligomers as well.

Thus, the present invention provides electrodes comprising monolayers comprising conductive oligomers, generally including capture probes, and either target sequences or label probes comprising recruitment linkers containing ETMs. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

Generally, the nucleic acid compositions of the invention are useful as oligonucleotide probes. As is appreciated by those in the art, the length of the probe will vary with the length of the target sequence and the hybridization and wash conditions. Generally, oligonucleotide probes range from about 8 to about 50 nucleotides, with from about 10 to about 30 being preferred and from about 12 to about 25 being especially preferred. In some cases, very long probes may be used, e.g. 50 to 200-300 nucleotides in length. Thus, in the structures depicted herein, nucleosides may be replaced with nucleic acids.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. The hybridization conditions may also vary when a non-ionic backbone, i.e. PNA is used, as is known in the art. In addition, cross-linking agents may be added after target binding to cross-link, i.e. covalently attach, the two strands of the hybridization complex.

As will be appreciated by those in the art, the systems of the invention may take on a large number of different configurations, as is generally depicted in the Figures. In general, there are three types of systems that can be used: (1) systems in which the target sequence itself is labeled with ETMs (see FIGS. 16A, 16B and 16D); (2) systems in which label probes directly hybridize to the target sequences (see FIGS. 16C and 16H); and (3) systems in which label probes are indirectly hybridized to the target sequences, for example through the use of amplifier probes (see FIGS. 16E, 16F and 16G).

In all three of these systems, it is preferred, although not required, that the target sequence be immobilized on the electrode surface. This is preferably done using capture probes and optionally one or more capture extender probes. When only capture probes are utilized, it is necessary to have unique capture probes for each target sequence; that is, the surface must be customized to contain unique capture probes. Alternatively, capture extender probes may be used, that allow a "universal" surface, i.e. a surface containing a single type of capture probe that can be used to detect any target sequence. "Capture extender" probes are generally depicted in FIG. 14, and have a first portion that will hybridize to all or part of the capture probe, and a second portion that will hybridize to a portion of the target sequence. This then allows the generation of customized soluble probes, which as will be appreciated by those in the art is generally simpler and less costly. As shown herein (e.g. FIG. 14C), two capture extender probes may be used. This has generally been done to stabilize assay complexes (for example when the target sequence is large, or when large amplifier probes (particularly branched or dendrimer amplifier probes) are used.

In a preferred embodiment, the nucleic acids are added after the formation of the SAM ((4) above). This may be done in a variety of ways, as will be appreciated by those in the art.

In one embodiment, conductive oligomers with terminal functional groups are made, with preferred embodiments utilizing activated carboxylates and isothiocyanates, that will react with primary amines that are put onto the nucleic acid, as is generally depicted in FIG. 6 using an activated carboxylate. These two reagents have the advantage of being stable in aqueous solution, yet react with primary alkylamines. However, the primary aromatic amines and secondary and tertiary amines of the bases should not react, thus allowing site specific addition of nucleic acids to the surface. This allows the spotting of probes (either capture or detection probes, or both) using known methods (ink jet, spotting, etc.) onto the surface.

In addition, there are a number of non-nucleic acid methods that can be used to immobilize a nucleic acid on a surface. For example, binding partner pairs can be utilized; i.e. one binding partner is attached to the terminus of the conductive oligomer, and the other to the end of the nucleic acid. This may also be done without using a nucleic acid capture probe; that is, one binding partner serves as the capture probe and the other is attached to either the target sequence or a capture extender probe. That is, either the target sequence comprises the binding partner, or a capture extender probe that will hybridize to the target sequence comprises the binding partner. Suitable binding partner pairs include, but are not limited to, hapten pairs such as biotin/streptavidin; antigens/antibodies; NTA/histidine tags; etc. In general, smaller binding partners are preferred, such that the electrons can pass from the nucleic acid into the conductive oligomer to allow detection.

In a preferred embodiment, when the target sequence itself is modified to contain a binding partner, the binding partner is attached via a modified nucleotide that can be enzymatically attached to the target sequence, for example during a PCR target amplification step. Alternatively, the binding partner should be easily attached to the target sequence.

Alternatively, a capture extender probe may be utilized that has a nucleic acid portion for hybridization to the target as well as a binding partner (for example, the capture extender probe may comprise a non-nucleic acid portion such as an alkyl linker that is used to attach a binding partner). In this embodiment, it may be desirable to cross-link the double-stranded nucleic acid of the target and capture extender probe for stability, for example using psoralen as is known in the art.

In one embodiment, the target is not bound to the electrode surface using capture probes. In this embodiment, what is important, as for all the assays herein, is that excess label probes be removed prior to detection and that the assay complex (the recruitment linker) be in proximity to the surface. As will be appreciated by those in the art, this may be accomplished in other ways. For example, the assay complex may be present on beads that are added to the electrode comprising the monolayer. The recruitment linkers comprising the ETMs may be placed in proximity to the conductive oligomer surface using techniques well known in the art, including gravity settling of the beads on the surface, electrostatic or magnetic interactions between bead components and the surface, using binding partner attachment as outlined above. Alternatively, after the removal of excess reagents such as excess label probes, the assay complex may be driven down to the surface, for example by pulsing the system with a voltage sufficient to drive the assay complex to the surface.

However, preferred embodiments utilize assay complexes attached via nucleic acid capture probes.

In a preferred embodiment, the target sequence itself contains the ETMs. As discussed above, this may be done using target sequences that have ETMs incorporated at any number of positions, as outlined above. Representative examples are depicted in FIGS. 16A, 16B and 16D. In this embodiment, as for the others of the system, the 3'-5' orientation of the probes and targets is chosen to get the ETM-containing structures (i.e. recruitment linkers or target sequences) as close to the surface of the monolayer as possible, and in the correct orientation. This may be done using attachment via insulators or conductive oligomers as is generally shown in the Figures. In addition, as will be appreciated by those in the art, multiple capture probes can be utilized, either in a configuration such as depicted in FIG. 16D, wherein the 5-3' orientation of the capture probes is different, or where "loops" of target form when multiples of capture probes are used.

In a preferred embodiment, the label probes directly hybridize to the target sequences, as is generally depicted in FIG. 16C. In these embodiments, the target sequence is preferably, but not required to be, immobilized on the surface using capture probes, including capture extender probes. Label probes are then used to bring the ETMs into proximity of the surface of the monolayer comprising conductive oligomers. In a preferred embodiment, multiple label probes are used; that is, label probes are designed such that the portion that hybridizes to the target sequence (labeled 141 in the figures) can be different for a number of different label probes, such that amplification of the signal occurs, since multiple label probes can bind for every target sequence. Thus, as depicted in the figures, n is an integer of at least one. Depending on the sensitivity desired, the length of the target sequence, the number of ETMs per label probe, etc., preferred ranges of n are from 1 to 50, with from about 1 to about 20 being particularly preferred, and from about 2 to about 5 being especially preferred. In addition, if "generic" label probes are desired, label extender probes can be used as generally described below for use with amplifier probes.

As above, generally in this embodiment the configuration of the system and the label probes are designed to recruit the ETMs as close as possible to the monolayer surface.

In a preferred embodiment, the label probes are hybridized to the target sequence indirectly. That is, the present invention finds use in novel combinations of signal amplification technologies and electron transfer detection on electrodes, which may be particularly useful in sandwich hybridization assays, as generally depicted in FIG. 16. In these embodiments, the amplifier probes of the invention are bound to the target sequence in a sample either directly or indirectly. Since the amplifier probes preferably contain a relatively large number of amplification sequences that are available for binding of label probes, the detectable signal is significantly increased, and allows the detection limits of the target to be significantly improved. These label and amplifier probes, and the detection methods described herein, may be used in essentially any known nucleic acid hybridization formats, such as those in which the target is bound directly to a solid phase or in sandwich hybridization assays in which the target is bound to one or more nucleic acids that are in turn bound to the solid phase.

In general, these embodiments may be described as follows. An amplifier probe is hybridized to the target sequence, either directly (e.g. FIG. 16E), or through the use of a label extender probe (e.g. FIGS. 16F and 16G), which serves to allow "generic" amplifier probes to be made. The target sequence is preferably, but not required to be, immobilized on the electrode using capture probes. Preferably, the amplifier probe contains a multiplicity of amplification sequences, although in some embodiments, as described below, the amplifier probe may contain only a single amplification sequence. The amplifier probe may take on a number of different forms; either a branched conformation, a dendrimer conformation, or a linear "string" of amplification sequences. These amplification sequences are used to form hybridization complexes with label probes, and the ETMs can be detected using the electrode.

Accordingly, the present invention provides assay complexes comprising at least one amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single-stranded nucleic acid amplification sequence, with a multiplicity of amplification sequences being preferred.

Amplifier probes comprise a first probe sequence that is used, either directly or indirectly, to hybridize to the target sequence. That is, the amplifier probe itself may have a first probe sequence that is substantially complementary to the target sequence (e.g. FIG. 16E), or it has a first probe sequence that is substantially complementary to a portion of an additional probe, in this case called a label extender probe, that has a first portion that is substantially complementary to the target sequence (e.g. FIG. 16F). In a preferred embodiment, the first probe sequence of the amplifier probe is substantially complementary to the target sequence, as is generally depicted in FIG. 16E.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, as is depicted in FIG. 14, the amplifier probes, or any of the other probes of the invention, may form hairpin stem-loop structures in the absence of their target. The length of the stem double-stranded sequence will be selected such that the hairpin structure is not favored in the presence of target. The use of these type of probes, in the systems of the invention or in any nucleic acid detection systems, can result in a significant decrease in non-specific binding and thus an increase in the signal to noise ratio.

Generally, these hairpin structures comprise four components. The first component is a target binding sequence, i.e. a region complementary to the target (which may be the sample target sequence or another probe sequence to which binding is desired), that is about 10 nucleosides long, with about 15 being preferred. The second component is a loop sequence, that can facilitate the formation of nucleic acid loops. Particularly preferred in this regard are repeats of GTC, which has been identified in Fragile X Syndrome as forming turns. (When PNA analogs are used, turns comprising proline residues may be preferred). Generally, from three to five repeats are used, with four to five being preferred. The third component is a self-complementary region, which has a first portion that is complementary to a portion of the target sequence region and a second portion that comprises a first portion of the label probe binding sequence. The fourth component is substantially complementary to a label probe (or other probe, as the case may be). The fourth component further comprises a "sticky end", that is, a portion that does not hybridize to any other portion of the probe, and preferably contains most, if not all, of the ETMs. The general structure is depicted in FIG. 14. As will be appreciated by those in the art, the any or all of the probes described herein may be configured to form hairpins in the absence of their targets, including the amplifier, capture, capture extender, label and label extender probes.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

In a preferred embodiment, the amplifier probe does not hybridize to the sample target sequence directly, but instead hybridizes to a first portion of a label extender probe, as is generally depicted in FIG. 16F. This is particularly useful to allow the use of "generic" amplifier probes, that is, amplifier probes that can be used with a variety of different targets. This may be desirable since several of the amplifier probes require special synthesis techniques. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'-3' orientation of the target or probe sequences. For example, assuming a 5'-3' orientation of the complementary target sequence, the first portion may be located either 5' to the second portion, or 3' to the second portion. For convenience herein, the order of probe sequences are generally shown from left to right.

In a preferred embodiment, more than one label extender probe-amplifier probe pair may be used, that is, n is more than 1. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce non-specific binding, as is depicted in FIG. 16G and generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below. Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to which at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end either directly or with short intervening sequences to form a polymer. As with the other amplifier configurations, there may be additional sequences or moieties between the amplification sequences. In addition, as outlined herein, linear amplification probes may form hairpin stem-loop structures, as is depicted in FIG. 14.

In one embodiment, the linear amplifier probe has a single amplification sequence. This may be useful when cycles of hybridization/disassociation occurs, forming a pool of amplifier probe that was hybridized to the target and then removed to allow more probes to bind, or when large numbers of ETMs are used for each label probe. However, in a preferred embodiment, linear amplifier probes comprise a multiplicity of amplification sequences.

In addition, the amplifier probe may be totally linear, totally branched, totally dendrimeric, or any combination thereof.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have first portion that binds to the amplification sequence and a second portion that binds to the first portion of the label probe.

In addition, the compositions of the invention may include "preamplifier" molecules, which serves a bridging moiety between the label extender molecules and the amplifier probes. In this way, more amplifier and thus more ETMs are ultimately bound to the detection probes. Preamplifier molecules may be either linear or branched, and typically contain in the range of about 30-3000 nucleotides.

The reactions outlined below may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Generally, the methods are as follows. In a preferred embodiment, the target is initially immobilized or attached to the electrode. In one embodiment, this is done by forming a hybridization complex between a capture probe and a portion of the target sequence. A preferred embodiment utilizes capture extender probes; in this embodiment, a hybridization complex is formed between a portion of the target sequence and a first portion of a capture extender probe, and an additional hybridization complex between a second portion of the capture extender probe and a portion of the capture probe. Additional preferred embodiments utilize additional capture probes, thus forming a hybridization complex between a portion of the target sequence and a first portion of a second capture extender probe, and an additional hybridization complex between a second portion of the second capture extender probe and a second portion of the capture probe.

Alternatively, the attachment of the target sequence to the electrode is done simultaneously with the other reactions.

The method proceeds with the introduction of amplifier probes, if utilized. In a preferred embodiment, the amplifier probe comprises a first probe sequence that is substantially complementary to a portion of the target sequence, and at least one amplification sequence.

In one embodiment, the first probe sequence of the amplifier probe is hybridized to the target sequence, and any unhybridized amplifier probe is removed. This will generally be done as is known in the art, and depends on the type of assay. When the target sequence is immobilized on a surface such as an electrode, the removal of excess reagents generally is done via one or more washing steps, as will be appreciated by those in the aft. In this embodiment, the target may be immobilized on any solid support. When the target sequence is not immobilized on a surface, the removal of excess reagents such as the probes of the invention may be done by adding beads (i.e. solid support particles) that contain complementary sequences to the probes, such that the excess probes bind to the beads. The beads can then be removed, for example by centrifugation, filtration, the application of magnetic or electrostatic fields, etc.

The reaction mixture is then subjected to conditions (temperature, high salt, changes in pH, etc.) under which the amplifier probe disassociates from the target sequence, and the amplifier probe is collected. The amplifier probe may then be added to an electrode comprising capture probes for the amplifier probes, label probes added, and detection is achieved.

In a preferred embodiment, a larger pool of probe is generated by adding more amplifier probe to the target sequence and the hybridization/disassociation reactions are repeated, to generate a larger pool of amplifier probe. This pool of amplifier probe is then added to an electrode comprising amplifier capture probes, label probes added, and detection proceeds.

In this embodiment, it is preferred that the target sequence be immobilized on a solid support, including an electrode, using the methods described herein; although as will be appreciated by those in the art, alternate solid support attachment technologies may be used, such as attachment to glass, polymers, etc. It is possible to do the reaction on one solid support and then add the pooled amplifier probe to an electrode for detection.

In a preferred embodiment, the amplifier probe comprises a multiplicity of amplification sequences.

In one embodiment, the first probe sequence of the amplifier probe is hybridized to the target sequence, and any unhybridized amplifier probe is removed. Again, preferred embodiments utilize immobilized target sequences, wherein the target sequences are immobilized by hybridization with capture probes that are attached to the electrode, or hybridization to capture extender probes that in turn hybridize with immobilized capture probes as is described herein. Generally, in these embodiments, the capture probes and the detection probes are immobilized on the electrode, generally at the same "address".

In a preferred embodiment, the first probe sequence of the amplifier probe is hybridized to a first portion of at least one label extender probe, and a second portion of the label extender probe is hybridized to a portion of the target sequence. Other preferred embodiments utilize more than one label extender probe.

In a preferred embodiment, the amplification sequences of the amplifier probe are used directly for detection, by hybridizing at least one label probe sequence.

The invention thus provides assay complexes that minimally comprise a target sequence and a label probe. "Assay complex" herein is meant the collection of hybridization complexes comprising nucleic acids, including probes and targets, that contains at least one ETM and thus allows detection. The composition of the assay complex depends on the use of the different probe component outlined herein. Thus, in FIGS. 16A, 16B and 16C, the assay complex comprises the capture probe and the target sequence. The assay complexes may also include label probes, capture extender probes, label extender probes, and amplifier probes, as outlined herein, depending on the configuration used.

The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions; for example, when an initial hybridization step is done between the target sequence and the label extender and capture extender probes. Running this step at conditions which favor specific binding can allow the reduction of non-specific binding.

In a preferred embodiment, when all of the components outlined herein are used, a preferred method is as follows. Single-stranded target sequence is incubated under hybridization conditions with the capture extender probes and the label extender probes. A preferred embodiment does this reaction in the presence of the electrode with immobilized capture probes, although this may also be done in two steps, with the initial incubation and the subsequent addition to the electrode. Excess reagents are washed off, and amplifier probes are then added. If preamplifier probes are used, they may be added either prior to the amplifier probes or simultaneously with the amplifier probes. Excess reagents are washed off, and label probes are then added. Excess reagents are washed off, and detection proceeds as outlined below.

In one embodiment, a number of capture probes (or capture probes and capture extender probes) that are each substantially complementary to a different portion of the target sequence are used.

Again, as outlined herein, when amplifier probes are used, the system is generally configured such that upon label probe binding, the recruitment linkers comprising the ETMs are placed in proximity to the monolayer surface. Thus for example, when the ETMs are attached via "dendrimer" type structures as outlined herein, the length of the linkers from the nucleic acid point of attachment to the ETMs may vary, particularly with the length of the capture probe when capture extender probes are used. That is, longer capture probes, with capture extenders, can result in the target sequences being "held" further away from the surface than for shorter capture probes. Adding extra linking sequences between the probe nucleic acid and the ETMs can result in the ETMs being spatially closer to the surface, giving better results.

In addition, if desirable, nucleic acids utilized in the invention may also be ligated together prior to detection, if applicable, by using standard molecular biology techniques such as the use of a ligase. Similarly, if desirable for stability, cross-linking agents may be added to hold the structures stable.

The compositions of the invention are generally synthesized as outlined below, generally utilizing techniques well known in the art. As will be appreciated by those in the art, many of the techniques outlined below are directed to nucleic acids containing a ribose-phosphate backbone. However, as outlined above, many alternate nucleic acid analogs may be utilized, some of which may not contain either ribose or phosphate in the backbone. In these embodiments, for attachment at positions other than the base, attachment is done as will be appreciated by those in the art, depending on the backbone. Thus, for example, attachment can be made at the carbon atoms of the PNA backbone, as is described below, or at either terminus of the PNA.

The compositions may be made in several ways. A preferred method first synthesizes a conductive oligomer attached to a nucleoside, with addition of additional nucleosides to form the capture probe followed by attachment to the electrode. Alternatively, the whole capture probe may be made and then the completed conductive oligomer added, followed by attachment to the electrode. Alternatively, a monolayer of conductive oligomer (some of which have functional groups for attachment of capture probes) is attached to the electrode first, followed by attachment of the capture probe. The latter two methods may be preferred when conductive oligomers are used which are not stable in the solvents and under the conditions used in traditional nucleic acid synthesis.

In a preferred embodiment, the compositions of the invention are made by first forming the conductive oligomer covalently attached to the nucleoside, followed by the addition of additional nucleosides to form a capture probe nucleic acid, with the last step comprising the addition of the conductive oligomer to the electrode.

The attachment of the conductive oligomer to the nucleoside may be done in several ways. In a preferred embodiment, all or part of the conductive oligomer is synthesized first (generally with a functional group on the end for attachment to the electrode), which is then attached to the nucleoside. Additional nucleosides are then added as required, with the last step generally being attachment to the electrode. Alternatively, oligomer units are added one at a time to the nucleoside, with addition of additional nucleosides and attachment to the electrode. A number of representative syntheses are shown in the Figures of PCT US97/20014, expressly incorporated herein by reference.

The conductive oligomer is then attached to a nucleoside that may contain one (or more) of the oligomer units, attached as depicted herein.

In a preferred embodiment, attachment is to a ribose of the ribose-phosphate backbone. Thus, attachment via amide and amine linkages are possible (see FIGS. 1 and 2 of CPT US97/20014). In a preferred embodiment, there is at least a methylene group or other short aliphatic alkyl groups (as a Z group) between the nitrogen attached to the ribose and the aromatic ring of the conductive oligomer. A representative synthesis is shown in FIG. 16 of PCT US97/20014.

Alternatively, attachment is via a phosphate of the ribose-phosphate backbone. Examples of two synthetic schemes are shown in FIG. 4 and FIG. 5 of PCT US97/20014. Although both Figures show attachment at the 3' position of the ribose, attachment can also be made via the 2' position. In FIG. 5, Z is an ethylene linker, although other linkers may be used as well, as will be appreciated by those in the art.

In a preferred embodiment, attachment is via the base. A general scheme is depicted in FIG. 3 of PCT US97/20014, using uridine as the nucleoside and a phenylene-acetylene conductive oligomer. As will be appreciated in the art, amide linkages are also possible, using techniques well known in the art. In a preferred embodiment, protecting groups may be added to the base prior to addition of the conductive oligomers, as is generally outlined in FIGS. 10 and 11 of PCT US97/20014. In addition, the palladium cross-coupling reactions may be altered to prevent dimerization problems; i.e. two conductive oligomers dimerizing, rather than coupling to the base.

Alternatively, attachment to the base may be done by making the nucleoside with one unit of the oligomer, followed by the addition of others.

Once the modified nucleosides are prepared, protected and activated, prior to attachment to the electrode, they may be incorporated into a growing oligonucleotide by standard synthetic techniques (Gait, Oligonucleotide Synthesis: A Practical Approach, IRL Press, Oxford, UK 1984; Eckstein) in several ways.

In preferred embodiments, for example for the SBE methods outlined herein, one or more modified nucleosides are converted to the triphosphate form and incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105-118. Academic Press, San Diego, Calif. 1981). Thus, the present invention provides deoxyribonucleoside triphosphates comprising a covalently attached ETM. Preferred embodiments utilize ETM attachment to the base or the backbone, such as the ribose (preferably in the 2' position), as is generally depicted below in Structures 42 and 43:

Structure 42

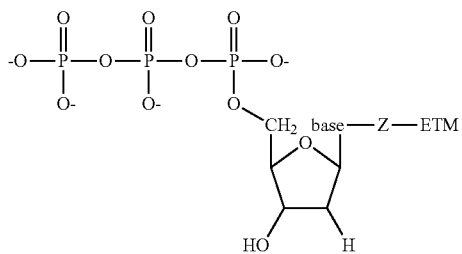

Structure 43

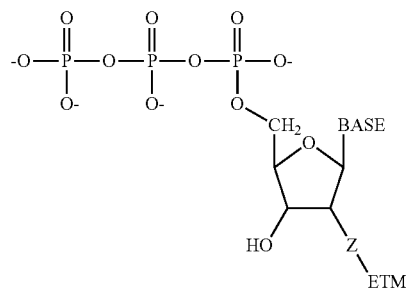

Thus, in some embodiments, it may be possible to generate the nucleic acids comprising ETMs in situ. For example, a target sequence can hybridize to a capture probe (for example on the surface) in such a way that the terminus of the target sequence is exposed, i.e. unhybridized. The addition of enzyme and triphosphate nucleotides labelled with ETMs allows the in situ creation of the label. Similarly, using labeled nucleotides recognized by polymerases can allow simultaneous PCR and detection; that is, the target sequences are generated in situ.

In a preferred embodiment, the modified nucleoside is converted to the phosphoramidite or H-phosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done in one of two ways. First, the 5' position of the ribose is protected with 4',4-dimethoxytrityl (DMT) followed by reaction with either 2-cyanoethoxy-bis-diisopropylaminophosphine in the presence of diisopropylammonium tetrazolide, or by reaction with chlorodiisopropylamino 2'-cyanoethyoxyphosphine, to give the phosphoramidite as is known in the art; although other techniques may be used as will be appreciated by those in the art. See Gait, supra; Caruthers, Science 230:281 (1985), both of which are expressly incorporated herein by reference.

For attachment of a group to the 3' terminus, 8 preferred method utilizes the attachment of the modified nucleoside (or the nucleoside replacement) to controlled pore glass (CPG) or other oligomeric supports. In this embodiment, the modified nucleoside is protected at the 5' end with DMT, and then reacted with succinic anhydride with activation. The resulting succinyl compound is attached to CPG or other oligomeric supports as is known in the art. Further phosphoramidite nucleosides are added, either modified or not, to the 5' end after deprotection. Thus, the present invention provides conductive oligomers or insulators covalently attached to nucleosides attached to solid oligomeric supports such as CPG, and phosphoramidite derivatives of the nucleosides of the invention.

The invention further provides methods of making label probes with recruitment linkers comprising ETMs. These synthetic reactions will depend on the character of the recruitment linker and the method of attachment of the ETM, as will be appreciated by those in the art. For nucleic acid recruitment linkers, the label probes are generally made as outlined herein with the incorporation of ETMs at one or more positions. When a transition metal complex is used as the ETM, synthesis may occur in several ways. In a preferred embodiment, the ligand(s) are added to a nucleoside, followed by the transition metal ion, and then the nucleoside with the transition metal complex attached is added to an oligonucleotide, i.e. by addition to the nucleic acid synthesizer. Alternatively, the ligand(s) may be attached, followed by incorporation into a growing oligonucleotide chain, followed by the addition of the metal ion.

In a preferred embodiment, ETMs are attached to a ribose of the ribose-phosphate backbone. This is generally done as is outlined herein for conductive oligomers, as described herein, and in PCT publication WO 95/15971, using amino-modified or oxo-modified nucleosides, at either the 2' or 3' position of the ribose. The amino group may then be used either as a ligand, for example as a transition metal ligand for attachment of the metal ion, or as a chemically functional group that can be used for attachment of other ligands or organic ETMs, for example via amide linkages, as will be appreciated by those in the art. For example, the examples describe the synthesis of nucleosides with a variety of ETMs attached via the ribose.

In a preferred embodiment, ETMs are attached to a phosphate of the ribose-phosphate backbone. As outlined herein, this may be done using phosphodiester analogs such as phosphoramidite bonds, see generally PCT publication WO 95/15971, or can be done in a similar manner to that depicted in FIGS. 4 and 5 of PCT US97/20014, where the conductive oligomer is replaced by a transition metal ligand or complex or an organic ETM, as well as is outlined in the Examples.

Attachment to alternate backbones, for example peptide nucleic acids or alternate phosphate linkages will be done as will be appreciated by those in the art.

In a preferred embodiment, ETMs are attached to a base of the nucleoside. This may be done in a variety of ways. In one embodiment, amino groups of the base, either naturally occurring or added as is described herein (see the figures, for example), are used either as ligands for transition metal complexes or as a chemically functional group that can be used to add other ligands, for example via an amide linkage, or organic ETMs. This is done as will be appreciated by those in the art. Alternatively, nucleosides containing halogen atoms attached to the heterocyclic ring are commercially available. Acetylene linked ligands may be added using the halogenated bases, as is generally known; see for example, Tzalis et al., Tetrahedron Lett. 36(34):6017-6020 (1995); Tzalis et al., Tetrahedron Lett. 36(2):3489-3490 (1995); and Tzalis et al., Chem. Communications (in press) 1996, all of which are hereby expressly incorporated by reference. See also the figures and the examples, which describes the synthesis of metallocenes (in this case, ferrocene) attached via acetylene linkages to the bases.

In one embodiment, the nucleosides are made with transition metal ligands, incorporated into a nucleic acid, and then the transition metal ion and any remaining necessary ligands are added as is known in the art. In an alternative embodiment, the transition metal ion and additional ligands are added prior to incorporation into the nucleic acid.

Once the nucleic acids of the invention are made, with a covalently attached attachment linker (i.e. either an insulator or a conductive oligomer), the attachment linker is attached to the electrode. The method will vary depending on the type of electrode used. As is described herein, the attachment linkers are generally made with a terminal "A" linker to facilitate attachment to the electrode. For the purposes of this application, a sulfur-gold attachment is considered a covalent attachment.

In a preferred embodiment, conductive oligomers, insulators, and attachment linkers are covalently attached via sulfur linkages to the electrode. However, surprisingly, traditional protecting groups for use of attaching molecules to gold electrodes are generally not ideal for use in both synthesis of the compositions described herein and inclusion in oligonucleotide synthetic reactions. Accordingly, the present invention provides novel methods for the attachment of conductive oligomers to gold electrodes, utilizing unusual protecting groups, including ethylpyridine, and trimethylsilylethyl as is depicted in the Figures. However, as will be appreciated by those in the art, when the conductive oligomers do not contain nucleic acids, traditional protecting groups such as acetyl groups and others may be used. See Greene et al., supra.

This may be done in several ways. In a preferred embodiment, the subunit of the conductive oligomer which contains the sulfur atom for attachment to the electrode is protected with an ethyl-pyridine or trimethylsilylethyl group. For the former, this is generally done by contacting the subunit containing the sulfur atom (preferably in the form of a sulfhydryl) with a vinyl pyridine group or vinyl trimethylsilylethyl group under conditions whereby an ethylpyridine group or trimethylsilylethyl group is added to the sulfur atom.

This subunit also generally contains a functional moiety for attachment of additional subunits, and thus additional subunits are attached to form the conductive oligomer. The conductive oligomer is then attached to a nucleoside, and additional nucleosides attached. The protecting group is then removed and the sulfur-gold covalent attachment is made. Alternatively, all or part of the conductive oligomer is made, and then either a subunit containing a protected sulfur atom is added, or a sulfur atom is added and then protected. The conductive oligomer is then attached to a nucleoside, and additional nucleosides attached. Alternatively, the conductive oligomer attached to a nucleic acid is made, and then either a subunit containing a protected sulfur atom is added, or a sulfur atom is added and then protected. Alternatively, the ethyl pyridine protecting group may be used as above, but removed after one or more steps and replaced with a standard protecting group like a disulfide. Thus, the ethyl pyridine or trimethylsilylethyl group may serve as the protecting group for some of the synthetic reactions, and then removed and replaced with a traditional protecting group.

By "subunit" of a conductive polymer herein is meant at least the moiety of the conductive oligomer to which the sulfur atom is attached, although additional atoms may be present, including either functional groups which allow the addition of additional components of the conductive oligomer, or additional components of the conductive oligomer. Thus, for example, when Structure 1 oligomers are used, a subunit comprises at least the first Y group.

A preferred method comprises 1) adding an ethyl pyridine or trimethylsilylethyl protecting group to a sulfur atom attached to a first subunit of a conductive oligomer, generally done by adding a vinyl pyridine or trimethylsilylethyl group to a sulfhydryl; 2) adding additional subunits to form the conductive oligomer; 3) adding at least a first nucleoside to the conductive oligomer; 4) adding additional nucleosides to the first nucleoside to form a nucleic acid; 5) attaching the conductive oligomer to the gold electrode. This may also be done in the absence of nucleosides, as is described in the Examples.

The above method may also be used to attach insulator molecules to a gold electrode.

In a preferred embodiment, a monolayer comprising conductive oligomers (and optionally insulators) is added to the electrode. Generally, the chemistry of addition is similar to or the same as the addition of conductive oligomers to the electrode, i.e. using a sulfur atom for attachment to a gold electrode, etc. Compositions comprising monolayers in addition to the conductive oligomers covalently attached to nucleic acids may be made in at least one of five ways: (1) addition of the monolayer, followed by subsequent addition of the attachment linker-nucleic acid complex; (2) addition of the attachment linker-nucleic acid complex followed by addition of the monolayer; (3) simultaneous addition of the monolayer and attachment linker-nucleic acid complex; (4) formation of a monolayer (using any of 1, 2 or 3) which includes attachment linkers which terminate in a functional moiety suitable for attachment of a completed nucleic acid; or (5) formation of a monolayer which includes attachment linkers which terminate in a functional moiety suitable for nucleic acid synthesis, i.e. the nucleic acid is synthesized on the surface of the monolayer as is known in the art. Such suitable functional moieties include, but are not limited to, nucleosides, amino groups, carboxyl groups, protected sulfur moieties, or hydroxyl groups for phosphoramidite additions. The examples describe the formation of a monolayer on a gold electrode using the preferred method (1).

In a preferred embodiment, the nucleic acid is a peptide nucleic acid or analog. In this embodiment, the invention provides peptide nucleic acids with at least one covalently attached ETM or attachment linker. In a preferred embodiment, these moieties are covalently attached to an monomeric subunit of the PNA. By "monomeric subunit of PNA" herein is meant the —NH—$CH_2CH_2$—N($COCH_2$-Base)-$CH_2$—CO— monomer, or derivatives (herein included within the definition of "nucleoside") of PNA. For example, the number of carbon atoms in the PNA backbone may be altered; see generally Nielsen et al., Chem. Soc. Rev. 1997 page 73, which discloses a number of PNA derivatives, herein expressly incorporated by reference. Similarly, the amide bond linking the base to the backbone may be altered; phosphoramide and sulfuramide bonds may be used. Alternatively, the moieties are attached to an internal monomeric subunit. By "internal" herein is meant that the monomeric subunit is not either the N-terminal monomeric subunit or the C-terminal monomeric subunit. In this embodiment, the moieties can be attached either to a base or to the backbone of the monomeric subunit. Attachment to the base is done as outlined herein or known in the literature. In general, the moieties are added to a base which is then incorporated into a PNA as outlined herein. The base may be either protected, as required for incorporation into the PNA synthetic reaction, or derivatized, to allow incorporation, either prior to the addition of the chemical substituent or afterwards. Protection and derivatization of the bases is shown in FIGS. 24-27 of PCT US97/20014. The bases can then be incorporated into monomeric subunits as shown in FIG. 28 of PCT US97/20014. FIGS. 29 and 30 of PCT US97/20014 depict two different chemical substituents, an ETM and a conductive oligomer, attached at a base. FIG. 29 depicts a representative synthesis of a PNA monomeric subunit with a ferrocene attached to a uracil base. FIG. 30 depicts the synthesis of a three unit conductive oligomer attached to a uracil base.

In a preferred embodiment, the moieties are covalently attached to the backbone of the PNA monomer. The attachment is generally to one of the unsubstituted carbon atoms of the monomeric subunit, preferably the $\alpha$-carbon of the backbone, as is depicted in FIGS. 31 and 32, although attachment at either of the carbon 1 or 2 positions, or the $\alpha$-carbon of the amide bond linking the base to the backbone may be done. In the case of PNA analogs, other carbons or atoms may be substituted as well. In a preferred embodiment, moieties are added at the $\alpha$-carbon atoms, either to a terminal monomeric subunit or an internal one.

In this embodiment, a modified monomeric subunit is synthesized with an ETM or an attachment linker, or a functional group for its attachment, and then the base is added and the modified monomer can be incorporated into a growing PNA chain. FIG. 31 of PCT US97/20014 depicts the synthesis of a conductive oligomer covalently attached to the backbone of a PNA monomeric subunit, and FIG. 32 of PCT US97/20014 depicts the synthesis of a ferrocene attached to the backbone of a monomeric subunit.

Once generated, the monomeric subunits with covalently attached moieties are incorporated into a PNA using the techniques outlined in Will et al., Tetrahedron 51(44):12069-12082 (1995), and Vanderlaan et al., Tett. Let. 38:2249-2252 (1997), both of which are hereby expressly incorporated in their entirety. These procedures allow the addition of chemical substituents to peptide nucleic acids without destroying the chemical substituents.

As will be appreciated by those in the art, electrodes may be made that have any combination of nucleic acids, conductive oligomers and insulators.

The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporated by reference.

Once made, the compositions find use in a number of applications, as described herein. In particular, the compositions of the invention find use in hybridization assays. As will be appreciated by those in the art, electrodes can be made that have a single species of nucleic acid, i.e. a single nucleic acid sequence, or multiple nucleic acid species.

In addition, as outlined herein, the use of a solid support such as an electrode enables the use of these gene probes in an array form. The use of oligonucleotide arrays are well known in the art. In addition, techniques are known for "addressing" locations within an electrode and for the surface modification of electrodes. Thus, in a preferred embodiment, arrays of different nucleic acids are laid down on the electrode, each of which are covalently attached to the electrode via a conductive linker. In this embodiment, the number of different probe species of oligonucleotides may vary widely, from one to thousands, with from about 4 to about 100,000 being preferred, and from about 10 to about 10,000 being particularly preferred.

Once the assay complexes of the invention are made, that minimally comprise a target sequence and a label probe, detection proceeds with electronic initiation. Without being limited by the mechanism or theory, detection is based on the transfer of electrons from the ETM to the electrode.

Detection of electron transfer, i.e. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the conductive oligomer used, the composition and integrity of the monolayer, and what type of reference electrode is used. As described herein, ferrocene is a preferred ETM.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochimica Acta 36:1799 (1991); and Alleman et al., J. Phys. Chem 100:17050 (1996); all of which are incorporated by reference.

In a preferred embodiment, an input electron source in solution is used in the initiation of electron transfer, preferably when initiation and detection are being done using DC current or at AC frequencies where diffusion is not limiting. In general, as will be appreciated by those in the art, preferred embodiments utilize monolayers that contain a minimum of "holes", such that short-circuiting of the system is avoided. This may be done in several general ways. In a preferred embodiment, an input electron source is used that has a lower or similar redox potential than the ETM of the label probe. Thus, at voltages above the redox potential of the input electron source, both the ETM and the input electron source are oxidized and can thus donate electrons; the ETM donates an electron to the electrode and the input source donates to the ETM. For example, ferrocene, as a ETM attached to the compositions of the invention as described in the examples, has a redox potential of roughly 200 mV in aqueous solution (which can change significantly depending on what the ferrocene is bound to, the manner of the linkage and the presence of any substitution groups). Ferrocyanide, an electron source, has a redox potential of roughly 200 mV as well (in aqueous solution). Accordingly, at or above voltages of roughly 200 mV, ferrocene is converted to ferricenium, which then transfers an electron to the electrode. Now the ferricyanide can be oxidized to transfer an electron to the ETM. In this way, the electron source (or co-reductant) serves to amplify the signal generated in the system, as the electron source molecules rapidly and repeatedly donate electrons to the ETM attached to the nucleic acid. The rate of electron donation or acceptance will be limited by the rate of diffusion of the co-reductant, the electron transfer between the co-reductant and the ETM, which in turn is affected by the concentration and size, etc.

Alternatively, input electron sources that have lower redox potentials than the ETM are used. At voltages less than the redox potential of the ETM, but higher than the redox potential of the electron source, the input source such as ferrocyanide is unable to be oxidized and thus is unable to donate an electron to the ETM; i.e. no electron transfer occurs. Once ferrocene is oxidized, then there is a pathway for electron transfer.

In an alternate preferred embodiment, an input electron source is used that has a higher redox potential than the ETM of the label probe. For example, luminol, an electron source, has a redox potential of roughly 720 mV. At voltages higher than the redox potential of the ETM, but lower than the redox potential of the electron source, i.e. 200-720 mV, the ferrocene is oxidized, and transfers a single electron to the electrode via the conductive oligomer. However, the ETM is unable to accept any electrons from the luminol electron source, since the voltages are less than the redox potential of the luminol. However, at or above the redox potential of luminol, the luminol then transfers an electron to the ETM, allowing rapid and repeated electron transfer. In this way, the electron source (or co-reductant) serves to amplify the signal generated in the system, as the electron source molecules rapidly and repeatedly donate electrons to the ETM of the label probe.

Luminol has the added benefit of becoming a chemiluminiscent species upon oxidation (see Jirka et al., Analytica Chimica Acta 284:345 (1993)), thus allowing photo-detection of electron transfer from the ETM to the electrode. Thus, as long as the luminol is unable to contact the electrode directly, i.e. in the presence of the SAM such that there is no efficient electron transfer pathway to the electrode, luminol can only be oxidized by transferring an electron to the ETM on the label probe. When the ETM is not present, i.e. when the target sequence is not hybridized to the composition of the invention, luminol is not significantly oxidized, resulting in a low photon emission and thus a low (if any) signal from the luminol. In the presence of the target, a much larger signal is generated. Thus, the measure of luminol oxidation by photon emission is an indirect measurement of the ability of the ETM to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the ETM such as a metallocene receiving an electron from the electrode, converting it to the metallicenium, with the output electron acceptor then accepting the electron rapidly and repeatedly. In this embodiment, cobalticenium is the preferred ETM.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedence. These methods include time or frequency dependent methods based on AC or DC currents, pulsed methods, lock-in techniques, filtering (high pass, low pass, band pass), and time-resolved techniques including time-resolved fluorescence.

In one embodiment, the efficient transfer of electrons from the ETM to the electrode results in stereotyped changes in the redox state of the ETM. With many ETMs including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp 197-202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with $Ru(4,7-biphenyl_2-phenanthroline)_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85-277, 1988). Preferred examples display efficient fluorescence (reasonably high quantum yields) as well as low reorganization energies. These include Ru(4,7-biphenyl$_2$-phenanthroline)$_3^{2+}$, Ru(4,4'-diphenyl-2,2'-bipyridine)$_3^{2+}$ and platinum complexes (see Cummings et al., J. Am. Chem. Soc. 118:1949-1960 (1996), incorporated by reference). Alternatively, a reduction in fluorescence associated with hybridization can be measured using these systems.

In a further embodiment, electrochemiluminescence is used as the basis of the electron transfer detection. With some ETMs such as Ru$^{2+}$(bpy)$_3$, direct luminescence accompanies excited state decay. Changes in this property are associated with nucleic acid hybridization and can be monitored with a simple photomultiplier tube arrangement (see Blackburn, G. F. Clin. Chem. 37: 1534-1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capicitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that ETMs, bound to an electrode, generally respond similarly to an AC voltage across a circuit containing resistors and capacitors. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV) and relatively large numbers of molecules. That is, the AC current (1) is not accurately described by Laviron's equation. This may be due in part to the fact that this theory assumes an unlimited source and sink of electrons, which is not true in the present systems.

The AC voltametry theory that models these systems well is outlined in O'Connor et al., J. Electroanal. Chem. 466(2): 197-202 (1999), hereby expressly incorporated by reference. The equation that predicts these systems is shown below as Equation 1:

$$i_{avg} = 2nfFN_{total} \cdot \frac{\sinh\left[\frac{nF}{RT} \cdot E_{AC}\right]}{\cosh\left[\frac{nF}{RT} \cdot E_{AC}\right] + \cosh\left[\frac{nF}{RT}(E_{DC} - E_O)\right]} \quad \text{Equation 1}$$

In Equation 1, n is the number of electrons oxidized or reduced per redox molecule, f is the applied frequency, F is Faraday's constant, $N_{total}$ is the total number of redox molecules, $E_O$ is the formal potential of the redox molecule, R is the gas constant, T is the temperature in degrees Kelvin, and $E_{DC}$ is the electrode potential. The model fits the experimental data very well. In some cases the current is smaller than predicted, however this has been shown to be caused by ferrocene degradation which may be remedied in a number of ways.

In addition, the faradaic current can also be expressed as a function of time, as shown in Equation 2:

$$I_f^*(t) = \frac{q_e N_{total} nF}{2RT\left(\cosh\left[\frac{nF}{RT}(V(t) - E_0)\right] + 1\right)} \cdot \frac{dV(t)}{dt} \quad \text{Equation 2}$$

$I_F$ is the Faradaic current and $q_e$ is the elementary charge.

However, Equation 1 does not incorporate the effect of electron transfer rate nor of instrument factors. Electron transfer rate is important when the rate is close to or lower than the applied frequency. Thus, the true $i_{AC}$ should be a function of all three, as depicted in Equation 3.

$$i_{AC} = f(\text{Nernst factors}) f(k_{ET}) f(\text{instrument factors}) \quad \text{Equation 3}$$

These equations can be used to model and predict the expected AC currents in systems which use input signals comprising both AC and DC components. As outlined above, traditional theory surprisingly does not model these systems at all, except for very low voltages.

In general, non-specifically bound label probes/ETMs show differences in impedance (i.e. higher impedances) than when the label probes containing the ETMs are specifically bound in the correct orientation. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Once the assay complex including the target sequence and label probe is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the sample and counter electrodes is swept through the electrochemical potential of the ETM (for example, when ferrocene is used, the sweep is generally from 0 to 500 mV) (or alternatively, the working electrode is grounded and the reference electrode is swept from 0 to −500 mV). The sweep is used to identify the DC voltage at which the maximum response of the system is seen. This is generally at or about the electrochemical potential of the ETM. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM.

For defined systems, it may be sufficient to apply a single input signal to differentiate between the presence and absence of the ETM (i.e. the presence of the target sequence) nucleic acid. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are Used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In a preferred embodiment, measurements of the system are taken at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input high frequency, and any changes in frequency response is an indication that the ETM is present, and thus that the target sequence is present.

In addition, the use of AC techniques allows the significant reduction of background signals at any single frequency due to entities other than the ETMs, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at least two separate frequencies, with measurements at a plurality of frequencies being preferred. A plurality of frequencies includes a scan. For example, measuring the output signal, e.g., the AC current, at a low input frequency such as 1-20 Hz, and comparing the response to the output signal at high frequency such as 10-100 kHz will show a frequency response difference between the presence and absence of the ETM. In a preferred embodiment, the frequency response is determined at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting baged detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In a preferred embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not effect the bulk impedance, and vice versa. Thus, the assay complexes comprising the nucleic acids in this system have a certain faradaic impedance, that will depend on the distance between the ETM and the electrode, their electronic properties, and the composition of the intervening medium, among other things. Of importance in the methods of the invention is that the faradaic impedance between the ETM and the electrode is signficantly different depending on whether the label probes containing the ETMs are specifically or non-specifically bound to the electrode.

Accordingly, the present invention further provides apparatus for the detection of nucleic acids using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In a preferred embodiment, the first measuring electrode comprises a single stranded nucleic acid capture probe covalently attached via an attachment linker, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected, for example using ribosomal RNA (rRNA) as the target sequences.

In a preferred embodiment, the nucleic acids of the invention find use as probes for toxic bacteria in the screening of water and food samples. For example, samples may be treated to lyse the bacteria to release its nucleic acid (particularly rRNA), and then probes designed to recognize bacterial strains, including, but not limited to, such pathogenic strains as, *Salmonella, Campylobacter, Vibrio cholerae, Leishmania,* enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labelled with a ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends, as is generally depicted in FIG. 7 of PCT US97/20014. By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^6$ molecules are detected, with less than about $10 \times 10^5$ being preferred, less than $10 \times 10^4$ being particularly preferred, less than about $10 \times 10^3$ being especially preferred, and less than about $10 \times 10^2$ being most preferred. As will be appreciated by those in the art, this assumes a 1:1 correlation between target sequences and reporter molecules; if more than one reporter molecule (i.e. electron transfer moeity) is used for each target sequence, the sensitivity will go up.

While the limits of detection are currently being evaluated, based on the published electron transfer rate through DNA, which is roughly $1 \times 10^6$ electrons/sec/duplex for an 8 base pair separation (see Meade et al., Angw. Chem. Eng. Ed., 34:352 (1995)) and high driving forces, AC frequencies of about 100 kHz should be possible. As the preliminary results show, electron transfer through these systems is quite efficient, resulting in nearly $100 \times 10^3$ electrons/sec, resulting in potential femtoamp sensitivity for very few molecules.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

General Methods of Making Substrates and Monolayers

SAM Formation on Substrates—General Procedure

The self-assembled monolayers were formed on a clean gold surface. The gold surface can be prepared by a variety of different methods: melted or polished gold wire, sputtered or evaporated gold on glass or mica or silicon wafers or some other substrate, electroplated or electroless gold on circuit board material or glass or silicon or some other substrate. Both the vacuum deposited gold samples (evaporated and sputtered) and the solution deposited gold samples (electroless and electroplated) often require the use of an adhesion layer between the substrate and the gold in order to insure good mechanical stability. Chromium, Titanium, Titanium/Tungsten or Tantalum is frequently employed with sputtered and evaporated gold. Electroplated nickel is usually employed with electroplated and electroless gold, however other adhesion materials can be used.

The gold substrate is cleaned prior to monolayer formation. A variety of different procedures have been employed. Cleaning with a chemical solution is the most prevalent. Piranha solution (hydrogen peroxide/sulfuric acid) or aqua regia cleaning (Hydrochloric acid/Nitric acid) is most prevalent, however electrochemical methods, flame treatment and plasma methods have also been employed.

Following cleaning, the gold substrate is incubated in a deposition solution. The deposition solution consists of a mixture of various thiols in a solvent. A mixture of alkane thiols in an organic solvent like ethanol is the most prevalent procedure, however numerous variations have been developed. Alternative procedures involve gas phase deposition of the alkane thiol, microcontact printing, deposition using neat thiol, deposition from aqueous solvent and two step procedures have been developed. The concentration of the alkane thiol in the deposition solution ranges from molar to submicromolar range with 0.5-2.0 millimolar being the most prevalent. The gold substrate is incubated/placed in contact with the deposition solution for less than a second to days depending on the procedure. The most common time is 1 hr to overnight incubation. The incubation is usually performed at room temperature, however temperatures up to 50° C. are common.

Mixed monolayers that contain DNA are usually prepared using a two step procedure. The thiolated DNA is deposited during the first deposition step and the mixed monolayer formation is completed during the second step in which a second thiol solution minus DNA is added. The second step frequently involves mild heating to promote monolayer reorganization.

General Procedure for SAM Formation-Deposited from Organic Solution

A clean gold surface was placed into a clean vial. A DNA deposition solution in organic solvent was prepared in which the total thiol concentration was between 400 uM and 1.0 mM. The deposition solution contained thiol modified DNA and thiol diluent molecules. The ratio of DNA to diluent was usually between 10:1 and 1:10 with 1:1 being preferred. The preferred solvents are tetrahydrofuran (THF), acetonitrile, dimethylforamide (DMF) or mixtures thereof. Sufficient DNA deposition solution is added to the vial so as to completely cover the electrode surface. The gold substrate is allowed to incubate at ambient temperature or slightly above ambient temperature for 5-30 minutes. After the initial incubation, the deposition solution is removed and a solution of diluent molecule only (100 uM-1.0 mM) in organic solvent is added. The gold substrate is allowed to incubate at room temperature or above room temperature until a complete monolayer is formed (10 minutes-24 hours). The gold sample is removed from the solution, rinsed in clean solvent and used.

General Procedure for SAM Formation-Deposited from Aqueous Solution

A clean gold surface is placed into a clean vial. A DNA deposition solution in water is prepared in which the total thiol concentration is between 1 uM and 200 uM. The aqueous solution frequently has salt present (approximately 1M), however pure water can be used. The deposition solution contains thiol modified DNA and often a thiol diluent molecule. The ratio of DNA to diluent is usually between 10:1 and 1:10 with 1:1 being preferred. The DNA deposition solution is added to the vial in such a volume so as to completely cover the electrode surface. The gold substrate is allowed to incubate at ambient temperature or slightly above ambient temperature for 1-30 minutes with 5 minutes usually being sufficient. After the initial incubation, the deposition solution is removed and a solution of diluent molecule only (10 uM-1.0 mM) in either water or organic solvent is added. The gold substrate is allowed to incubate at room temperature or above room temperature until a complete monolayer is formed (10 minutes-24 hours). The gold sample is removed from the solution, rinsed in clean solvent and used.

Monolayers on Au Ball Electrodes

Creating Au Ball Electrodes: Use a razor blade to cut 10 cm lengths of gold wire (127 μm diameter, 99.99% pure; e.g. from Aldrich). Use a 16 gauge needle to pass the wire through a #4 natural rubber septum (of the size to fit over a ½ mL PCR eppendorf tube). (This serves to support the wire and seal the tubes during deposition. See below.) Use a clean-burning flame (methane or propane) to melt one centimeter of the wire and form a sphere attached to the wire terminus. Adjust the wire length such that when sealed in a PCR tube the gold ball would be positioned near the bottom, able to be submerged in 20 μL of liquid. On the day of use, dip the electrodes in aqua regia (4:3:1 $H_2O:HCl:HNO_3$) for 20 seconds and then rinse thoroughly with water.

Derivatization: For 5 minutes, heat 20 μL aliquots of deposition solutions (2:2:1 DNA/H6/M44 at 833 μM total in DMF) in PCR tubes on a PCR block at 50° C. Then put each electrode into a tube of deposition solution (submerging just the gold ball—as little of the wire "stem" as possible) and remove to room temperature. Incubate for fifteen minutes before transferring the electrodes into PCR tubes with 200 μL of 400 μM M44 in DMF (submerging much of the wire stem as well). Let sit in M44 at room temperature for 5 minutes, then put on the PCR block and run HCLONG. Take electrodes out of the M44 solution, dip in 6×SSC, and place in PCR tubes with 20 μL of hybridization solution. Dip electrodes in 6×SSC prior to ACV measurement.

HCLONG: 65° C. 2', −0.3° C./s to 40° C., 40° C. 2', +0.3° C./s to 55° C., 55° C. 2', −0.3° C./s to 30° C., 30° C. 2', +0.3° C./s to 35° C., 35° C. 2', −0.3° C./s to 22° C.

Manufacture of Circuit Boards

An 18"×24"×0.047" panel of FR-4 (General Electric) with a half-ounce copper foil on both sides was drilled according to specifications (Gerber files). The FR-4 panel is plated with electroless copper (500 microinches) to make the specified drill-holes conductive and then panel is plated with an additional 500 microinches of electroplated copper. Following copper plating, the panel is etched according to specifications via cupric chloride etching (acid etching). The etched panel is then plated with 400 microinches of electroplated nickel with brightner followed by 50 microinches of soft gold (99.99% purity). The gold panel is coated with liquid photoimagable solder mask (Probimer 52, Ciba-Geigy Co.) on both sides of the panel. The imaging is done according to specifications. 14 sensor electrodes that are 250 micron in diameter and 2 larger electrodes (500 microns in diameter) are created with insulated leads leading to gold plated contacts at the edge of the board. The solder masked panel is then scored according to specifications to create individual wafers that are 1"×1". A silver/silver chloride paste is applied to one of the two larger electrodes (ERCON R-414). The panel is then plasma cleaned with an Argon/Oxygen Plasma mixture. Following cleaning, the panel is stored in a foil-lined bag until use.

Monolayer Deposition on Circuit Boards

The circuit boards are removed from the foil-lined bags and immersed in a 10% sulfuric acid solution for 30 seconds. Following the sulfuric acid treatment, the boards are immersed in two Milli-Q water baths for 1 minute each. The boards are then dried under a stream of nitrogen. The boards are placed on a X-Y table in a humidity chamber and a 30 nanoliter drop of DNA deposition solution is placed on each of the 14 electrodes. The DNA deposition solution consists of 33 uM thiolated DNA, 33 uM 2-unit phenylacetylene wire (H6), and 16 uM M44 in 6×SSC (900 mM sodium chloride, 90 mM sodium Citrate, pH 7) w/1% Triethylamine. The drop is incubated at room temperature for 5 minutes and then the drop is removed by rinsing in a Milli-Q water bath. The boards are immersed in a 45° C. bath of M44 in acetonitrile. After 30 minutes, the boards are removed and immersed in an acetonitrile bath for 30 seconds followed by a milli-Q water bath for 30 seconds. The boards are dried under a stream of nitrogen.

Example 2

Detection of Target Sequences

Monolayer Deposition on Circuit Boards

As above, the circuit boards were removed from the foil-lined bags and immersed in a 10% sulfuric acid solution for 30 seconds. Following the sulfuric acid treatment, the boards were immersed in two Milli-Q water baths for 1 minute each. The boards were then dried under a stream of nitrogen. The boards were placed on a X-Y table in a humidity chamber and a 30 nanoliter drop of DNA deposition solution was placed on each of the 14 electrodes. The DNA deposition solution consisted of 33 uM thiolated DNA, 33 uM 2-unit phenylacetylene wire (H6), and 16 uM undec-1-en-11yltri(ethylene glycol)

(HS—CH$_2$)$_{11}$—(OCH$_2$CH$_2$)$_3$—OH) in 6×SSC (900 mM sodium chloride, 90 mM sodium Citrate, pH 7) w/1% Triethylamine. 3 electrodes were spotted with a solution containing DNA 1 (5'-ACCATGGACACAGAT(CH$_2$)$_{16}$SH-3'). 4 electrodes were spotted with a solution containing DNA 2 (5'TCATTGATGGTCTCTTTTAACA((CH$_2$)$_{16}$SH-3'). 4 electrodes were spotted with DNA 3 (5'CACAGTGGGGG-GACATCAAGCAGCCATGCAAA(CH$_2$)$_{16}$SH-3'). 3 electrodes were spotted with DNA 4 (5'-TGTGCAGT-TGACGTGGAT(CH$_2$)$_{16}$SH-3'). The deposition solution was allowed to incubate at room temperature for 5 minutes and then the drop was removed by rinsing in a Milli-Q water bath. The boards were immersed in a 45° C. bath of M44 in acetonitrile. After 30 minutes, the boards were removed and immersed in an acetonitrile bath for 30 seconds followed by a milli-Q water bath for 30 seconds. The boards were dried under a stream of nitrogen and stored in foiled-lined bags flushed with nitrogen until use.

Hybridization and Measurement

The modified boards were removed from the foil-lined bags and fitted with an injection molded sample chamber (cartridge). The chamber was adhered to the board using double-sided sticky tape and had a total volume of 250 microliters. A hybridization solution was prepared. The solution contains 10 nM DNA target (5'-TGTGCAGTTGACGTG-GATTGTTAAAAGAGACCATCAATGAGGAAGCTGCA GAATGGGATAGAGTCATCCAGT-3' (D-998), 30 nM signaling probe (D-1055) and 10 nm 5'-TCTACAG(N6)C(N6)ATCTGTGTCCATGGT-3' (N6 is shown in FIG. 1D of PCTUS99/01705; it comprises a ferrocene connected by a 4 carbon chain to the 2' oxygen of the ribose of a nucleoside). The signalling probe is as follows:

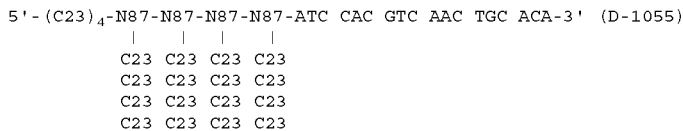

N87 is a branch point comprising a ring structure. C23 is shown in FIG. 1F of PCTUS99/01705. In a solution containing 25% Qiagen lysis buffer AL, 455 mM NaClO$_4$, 195 mM NaCl, 1.0 mM mercaptohexanol and 10% fetal calf serum. 250 microliters of hybrid solution was injected into the cartridge and allowed to hybridize for 12 hours. After 12 hours, the hybridized chip was plugged into a homemade transconductance amplifier with switching circuitry. The transconductance amplifier was equipped with summing circuitry that combines a DC ramp from the computer DAQ card and an AC sine wave from the lock-in amplifier (SR830 Stanford Instruments). Each electrode was scanned sequentially and the data was saved and manipulated using a homemade program designed using Labview (National Instruments). The chip was scanned at between –100 mV and 500 mV (pseudo Ag/Ag/Cl reference electrode) DC with a 25 mV (50 mV peak to peak), 1000 Hz superimposed sine wave. The output current was fed into the lock-in amplifier and the 1000 Hz signal was recorded (ACV technique). The data for each set of pads was compiled and averaged.

|  | Ip | Relative Intensity Ip |
|---|---|---|
| DNA 1 (Positive 2 Fc) | 34 nA | 0.11 |
| DNA 2 (Positive Sandwich Assay) | 218 nA | 0.7 |

|  | Ip | Relative Intensity Ip |
|---|---|---|
| DNA 3 (Negative) | 0.3 nA | 0.001 |
| DNA 4 (Positive Sandwich Assay) | 317 nA | 1 |

The results are shown in FIG. 14 of U.S. Ser. No. 09/338,726.

Example 2

The Use of Temperature and Competimers to Determine Sequence

The ability to discriminate single nucleotide polymorphisms (SNPs) is an important goal. We tested for the ability to discriminate single nucleotide mutations in the Hereditary Hemochromatosis gene (HFE), in which an abnormal protein product results in iron overload. We first established a sandwich assay for mismatch detection in the surface probe binding domain of the target. The 76-mer oligonucleotide model sequence for HIV served as the initial target and subsequently model oligos mimicking HFE amplicons were used. Finally we tested asymmetric PCR (A-PCR) products from HH (hereditary hemochromatosis) patients to confirm the utility of arrayed sandwich assays to genotype patient samples with respect to two prevalent mutations. We also developed a model OLA assay that reveals our ability to detect a single backbone bond cleavage.

Discrimination of Point Mismatch in HIV or HFE 76 bp Model Oligos within the Surface Probe Binding Domain Using a Sandwich Assay Introduction: The 76-mer HIV model oligo (D765) and its corresponding 22-mer surface probe (D761) as well as a modified target with a single nulceotide substitution and a modified capture probe with a complementary substitution were used in an HIV sandwich assay (see Material and Methods). The original, unmodified target oligo was designated as the wild type (D765) target, while the one nucleotide modified target oligo was designated the mutant (D941) target. A 21-mer surface probe (D1182), one base shorter than D761 was designated as wild type and the one nucleotide modified surface probe oligo was designated as mutant (D1181).

A 76-mer HFE oligo (D1117) was prepared to serve as a wild type model target for the CYS282Y location as well as its corresponding 21-mer surface probe (D1183) and their signal oligo (D1138). Oligo D1118 serves as mutant model target and its corresponding 21-mer surface probe is D1184. Signaling oligo D1138 is compatible with both wild type C282 and mutant Y282 target sequences.

The second most common mutation associated with HH is located at position 63 (H63D mutation, a C to G transversion). D1121 is the wild type model target for H63, and D1122 is the mutant model target for D63 (Beutler et al. Mutation analysis in hereditary hemochromatosis. Blood Cells, Molecules, and Diseases 22: 187-194, 1996) (Bulaj et al. Clinical and biochemical abnormalities in people heterozygotes for hemochromatosis. N. Engl. J. Med. 335: 1799-1805, 1996) (Feder et al. A novel MHC Class I-like gene is mutated in patients with hereditary hemochromatosis. Nature Genetica 13: 399-408, 1996) (Witte et al. Hereditary hemochromatosis. Practice Guideline Development Task Force of the College of American Pathologists. Clin. Chem. Acta 245: 139-2000, 1996). The corresponding capture and signaling probes for H63D model targets are designated as D1185 (wild-type capture), D1186 (mutant capture) and D1139 (common signaling) as shown in Material and Methods.

Thermodynamic considerations lead us to speculate that wild type and mutant targets will be differentially associated with perfectly matched and mismatched target probes after hybridization and subsequent exposure to elevated temperature. Melting point, Tm, is defined as the temperature at which 50% of sister strands in solution are in the duplex state and 50% are single-stranded. The Tm of mismatched pair (wild type target hybridized with mutant probe or mutant target hybridized with wild type probe) is lower than that of the perfectly matched pair (wild type-target with wild type-probe or mutant-target with mutant-probe).

We predicted that perfectly matched targets and mismatched targets would show a similar disparity in the stability to temperature increase on the sensor as seen in solution. Specifically, we predicted that the mismatched pair would dissociate and the electrochemical signaling would decrease, while the matched pair would remain annealed and continue to produce an electrochemical signal. However, we considered that the best temperature for observing the difference on the surface might differ from the Tm in solution.

Material and Methods
1: DNA Oligos Prepared
(D765): WT-Target
5'GACATCAAGCAGCCATGCAAATGT-TAAAAGAGACCATCAATGAGGAAGCTG-CAGAATGGGATA GAGTGCATCCAGT-3'
(D941): D765 mut-Target
5'GACATCAAGCgGCtATGCAAATGTTAAAAGAGACCATCAATGAGGAAGCTGCAGAATGGGATAGAGTGCATCCAGT-3'
D772): WT-Signal
[N6]C[N6]G[N6]C[N6]GCTTA[N6]C[N6]G[N6]C[N6]G[C131]TTTGCATGGCTGCTTGATGTC-3'
(D761): WT-Surface
5'-TCATTGATGGTCTCTTTTAACA(P282)-3'
(D1181): mut_D761
5'-CATTGATGGTGTCTTTTAACA(P282)-3'
(D1182): WT_D761
5'-CATTGATGGTCTCTTTTAACA(P282)-3'
(D1183): HFE surface WT1_C
5'-AGATATACGTGCCAGGTGGAGp(282)-3'
(D1184): HFE surface mut1_C
5'-AGATATACGTACCAGGTGGAGp(282)-3'
(D1138): HFE signal1_C
5'-(N6)C(N6)G(N6)C(N6)GCTTA(N6)C(N6)G(N6)C(N6)G(C131)CACCCAGGCCTGGATCAGC-3'
(D1117): HFE target WT1_C
5'GCTGATCCAGGCCTGGGTGCTCCACCTG-GCACGTATATCTCTGCTCTTCCCCAGGGGGTACA GCCAAGGTTATCCA-3'
(D1118): HFE target mut1_C
5'GCTGATCCAGGCCTGGGTGCTCCACCTG-GTACGTATATCTCTGCTCTTCCCCAGGGGGTACA GCCAAGGTTATCCA-3'
(D1185): HFE surface WT2_H
5'-GTTCTATGATCATGAGAGTCGp(282)-3'
(D1186): HFE surface mut2_H
5'-GTTCTATGATGATGAGAGTCGp(282)-3'
(D1139): HFE signal_H
5'-(N6)C(N6)G(N6)C(N6)GCTTA(N6)C(N6)G(N6)C(N6)G(C131)CCGTGTGGAGCCCCGAACT-3'
(D1121): HFE target WT2_H
5'AGTTCGGGGCTCCACACGGCGACTCT-CATGATCATAGAACACGAACAGCTGGT-CATCCACGTA GCCCAAAGCTTCA-3'
(D1122): HFE target mut2_H
5'AGTTCGGGGCTCCACACGGCGACTCT-CATCATCATAGAACACGAACAGCTGGT-CATCCACGTA GCCCAAAGCTTCA-3'
PCR HFE primerF1_C
5'-TGGCAAGGGTAAACAGATCC-3'
PCR HFE primerR1_C
5'-CTCAGGCACTCCTCTCAACC-3'
PCR HFE primerF2_H
5'-ACATGGTTAAGGCCTGTTGC-3'
PCR HFE primerR2_H
5'-GCCACATCTGGCTTGAAATT-3'

2: Chips Prepared:
The deposition solutions were mixed with surface probes as described above. The DNA probes were deposited onto chips as above as follows: D1183 (HFE-C,WT), D1184 (HFE-C mut), D1185 (HFE_H WT), D1186 (HFE_H, mut), D761/D1182 (HIV,WT), and D1181 (HIV,mut) onto chips, followed by post-treatment of chips with M44/Acetonitrile/Heat as above. The chips were mounted in cartridges.

3: Prepare Hybridization Buffer with Target and Signaling Oligos:
Human whole blood was combined with an equal volume of AL (from Qiagen) lysis buffer and 1/8 blood vol. of Proteinase K (20 mg/ml) and then incubated at 70° C. for 10 minutes. Target and Signaling oligos at 0.5 uM and 1.25 uM respectively were added to the lysed blood along with 2M NaClO4 (1/1 in volume) and hybridization was conducted for 20 minutes at room temperature. The electrode arrays were placed in a thermal cycler and the desired temperature was achieved through monitoring a separate array that had been filled with glycerol and contained a thermometer probe. The electrochemical signal for each electrode pad was measured using the DAQ-o-Matic system (at different temperatures).

Results and Discussion: The electrochemical response was examined as a function of temperature for matches and mismatches using wild type (D765) or mutated HIV targets (D1095) and the D772 signaling oligo. The analyses were conducted with 0.5 uM of target and 1.25 uM signaling oligo hybridizing with wild type electrode arrays for 20 minutes at 25° C. The chips were then moved to a thermal cycler to reach a desired temperature for 2 minutes and the electrochemical signals were measured. (FIG. 19). According to the graph in FIG. 19, the perfectly matched wild-type target/wild-type surface oligo pair exhibits a Tm of about 54° C., and the mismatched mutant target/wild-type surface oligo pair exhibits Tm about 38° C. At 45° C., the perfectly matched and mismatched complexes exhibit significant differences in electrochemical signaling relative to the starting point (defined as 100% for the initial output at 25° C.).

The results presented in FIG. 19 suggested that genotyping of the wild-type and mutant HIV oligos could be achieved by comparison of the signal output for homogeneous and heterogeneous samples at 25° C. and 45° C. When the hybridization solution contains only wild-type or mutant HIV target, the electrochemical signal from the perfectly matched pairs exhibit 2 to 20 folds higher signal than that of mismatched pairs, under stringent temperature (FIG. 20, three chips shown for each condition). Note that maximal discrimination of the wild-type target on the mutant capture probe was achieved at 45° C., while maximal discrimination of the mutant target on the wild-type probe required analysis at 55° C. The latter observation is likely a consequence of the specific nature of the mismatched base pair, since mismatches are known to vary in their destabilizing effects.

Our ability to discriminate mismatched duplexes when arrays were challenged with a homogeneous target, wild-type or mutant, suggested that we might be able to genotype with the array. Specifically, we hypothesized that arrays hybridized with equimolar amounts of wild-type and mutant targets would generate similar output on both wild-type and mutant capture probe containing electrodes at elevated temperatures. FIG. 21 graphically presents the results from three separate arrays (Mix-1 through -3) challenged with such a mixture of wild-type and mutant HIV oligos. The electrochemical signal is greatest at 25° C. similar to the results obtained with homogeneous targets. However, in contrast to the results seen with homogeneous targets, the electrochemical signal from pads containing wild-type or mutant capture probes are within two-fold of one another at 45° C. and 55° C. (FIG. 21). We interpret these findings to indicate that each electrode was initially hybridized with both perfectly matched and mismatched targets and each retain the perfectly matched targets and thus continue to signal at equal intensity at elevated temperatures.

We noted that signal output from the perfect matches decreases, in general, as the array is heated from 45° C. to 55° C. We reasoned, however, that if sufficient signal remained on the electrode housing perfect matches, a single temperature might facilitate genotyping. In order to test our hypothesis, a stringent hybridization condition (52° C.) was used in an attempt to differentiate samples containing wild type, mutant, or a mixture of wild-type and mutant oligos. FIG. 22 shows the results obtained from such an analysis. The results clearly show that the samples can be genotypes after 3 minutes at 52° C. Specifically, samples containing a homogeneous target typically exhibit 10-fold or greater difference between electrode types at elevated temperature, while the sample containing a heterogeneous target load generates signals of less than 2-fold difference between electrode types. Note that absolute signal is reported on the left and normalized output is reported on the right.

Given our success in genotyping the HIV samples, we proceeded to analyze the HFE model target oligos. The Tm of each oligo was determined theoretically and elevated temperatures were chosen that were predicted to facilitate discrimination of mismatches for the two different targets (C2828Y and H63D) under study. FIG. 5 presents the results graphically. The percent G+C of the C282Y capture probe is higher (52%) than that of H63D (43%). Thus, the temperature was used to differentiate mutant from wild type for model C282Y is 52° C. and the temperature used for model H63D is 46° C. The electrochemical signal is reduced at elevated temperature for mismatches between 4 and 20-fold depending on which target and capture probe pair are considered. In contrast, samples containing both targets in equimolar concentrations result in less than 2-fold differences between electrode types at the elevated temperature. Thus, the array of sensors can be used to genotype model HFE oligos that represent the two most common mutations in the gene.

Example 3

Genotype Determination of Hereditary Hemochromatosis by Detecting Single Nucleotide Mismatch in Asymmetric PCR (A-PCR) Products Purpose: To confirm that the sandwich assay that was developed for mismatch detection of HFE model targets can be used to detect the same mutation in A-PCR product.

Introduction Hereditary Hemochromatosis is the most prevalent identified inheritable disease. HH often goes undiagnosed and is frequently the root cause of many metabolic disorders.

The most common mutation of HH is a cysteine-to-tyrosine mutation at position 282 (C282Y mutation), resulting from a guanine-to-adenine transition. PrimerF1_C and PrimerR1_C, listed in Materials and Methods, were originally designed for PCR diagnosis of the HH mutation at 282. The original method uses this primer pair to amplify a 388 bp fragment by PCR and genotype is determined by subsequent Rsa I restriction digestion and agarose gel electrophoresis. The mutated PCR product has an extra Rsa I site and will generate an extra fragment of 11 bp after Rsa I treatment.

The second most common mutation associated with HH occurs at position 63 (H63D mutation, a G to C mutation). PrimerF1_H and PrimerR1_H, listed in Materials and Methods, were originally designed for PCR diagnosis of the HH mutation at position 63. The original method uses this primer pair to amplify a 209 bp fragment by PCR and the genotype is determined after Dpn II digestion. The wild-type PCR product has one Dpn II site and will result in fragments of 139 bp and 70 bp after Dpn II treatment, while the mutant PCR product, lacking a Dpn II site will retain the intact 209 bp fragment after Dpn II treatment.

In our experiments, we used the pairs of primers in an asymmetric ratio (Primer_R to Primer_F was 5 to 1) to produce the PCR products that contain single-stranded DNA. After confirming the correct identity of the PCR products by restriction digestion, we mixed the A-PCR products and signaling oligos (D1138 or D1139) in hybridization buffer as described in Materials and Methods. The A-PCR products were then detected in an HFE sandwich assay.

Material and Methods

1: DNA Oligos Prepared
PCR HFE primerF1_C
5'-TGGCAAGGGTAAACAGATCC-3'
PCR HFE primerR1_C
5'-CTCAGGCACTCCTCTCAACC-3'
PCR HFE primerF2_H
5'-ACATGGTTAAGGCCTGTTGC-3'
PCR HFE primerR2_H
5'-GCCACATCTGGCTTGAAATT-3'
2: Chips as Used for Hfe Model Sandwich Assay (Above)

PCR conditions are: 50 to 100 ng genomic DNA in 50 ul PCR reaction with 1 mM dNTP, 2 mM MgCl2, 1×PCR buffer, 600 nM of Primer_R, 120 nM of Primer_F, denatured at 95° C., annealing at 53° C., and elongating at 72° C., 50 seconds for each step for 42 cycles.

10 ul of PCR product is restriction digested to confirm the genotype of individual samples. Rsa I (C_Fragment) or Dpn II (H_Fragment) was incubated with PCR products at 37° C. for one hour and the samples fragments were subjected to electrophoresis in 2% agarose gels and subsequently stained with ethidium bromide.

20 ul of PCR product was mixed with 125 nM signaling oligo (D1138 for C_fragment, D1139 for H_fragment), heated to 100° C. for 1 minute, cooled on ice for 3 minutes, and then mixed with hybridization buffer (lysed blood with sodium perchlorate). The hybridizing buffer containing the A-PCR products was injected to HFE chips at room temperature and allowed to hybridize for 4 hours.

Measurement of the electrochemical signal in DAQ-o-Matic at 25, 45 and 50° C.

If the signal detected after 4 hours hybridization was lower than 10 nA, we purified the PCR product with the Qiagen PCR purification Kit and then used one-tenth of this purified product as DNA template to produce second A-PCR product with only a single primer. The products of the second A-PCR were then analyzed on the HH genotyping chip.

Results:

A-PCR products of C_Fragment (388 bp) or H_Fragment (209 bp) were hybridized separately over electrodes containing the surfaces probe for HFE model sandwich assay. As was the case for the model target oligos, the temperature at which discrimination was afforded differed between the two targets, 45° C. for H_Fragment and 50° C. for C_Fragment. We analyzed the electrochemical signal at 25° C. and subsequently at elevate temperature. The results are presented graphically in FIG. 24. While signal output declines on all pads at the elevated temperatures, the signal output from the mismatched complexes shows a greater decline. Specifically, signal output from the perfectly matched sandwich complexes is 3 to 30-fold higher than that from the mismatched pads at the elevated temperature (e.g. 50WT-C and 45mut-D). As was observed with the model oligos, samples containing heterogeneous targets resulted in signal output that differed by less than 2-fold between the two types of electrodes at elevated temperature (50mix-CY and 45mix-HD).

Our success in genotyping the two HFE amplicons individually encouraged us to attempt a multiplex PCR reaction followed by a single array analysis of the A-PCR products for a complete genotyping with respect to C282Y and H63D in a single chip. A previously characterized patient sample was subjected to two rounds of A-PCR as described above. The A-PCR products were hybridized over two electrode arrays for 4 hours and then electrochemical signaling was measured at 25° C. and 43° C. (after 2 minutes heating). The results are presented graphically in FIG. 25. At 43° C., electrodes that are a perfect match to the 282Y mutation exhibit signal output less than 113 of the electrodes containing the perfect match for the wild-type allele. The observation suggests that the genome is homozygous wild-type at the 282 position. In contrast, at the elevated temperature, the H63D electrodes exhibit signal outputs that are within 2-fold of one another. The latter observation suggests that the genome analyzed is heterozygous at the 63 position. Our genotyping results are in agreement with the previous characterization of this patient sample.

Example 4

Addressing Oligonucleotides to Electrodes by Virtue of Single Base Mismatches

Purpose: To establish a protocol for the selective localization of oligonucleotides to specific electrodes by virtue of single nucleotide variation.

Introduction: Two different Ferrocene molecules N6 and W97 as depicted in FIG. 1 were used to label wild type or mutant HIV oligonucleotides respectively. The "two colors", i.e. two different redox potentials, provide a means of distinguishing the two oligos during analysis of electrochemical signaling. When the labeled molecules are captured at surfaces by hybridizing with the pre-deposited capture probes, N6-wild type HIV gives signal at about 160 mV, and W97- mutant HIV gives signal at about 350 mV. Based on the peak heights resulting from ferrocene signaling at 160 or 350 mV, we could determine the ratio of hybridization from perfectly-matched pairs and mismatched pairs. We predicted that as the hybridization condition was made more stringent, the mismatched oligo pair would denature in preference to the perfectly matched oligo. Moreover, we speculated that we might drive the oligos exclusively to electrodes where they are perfectly matched through repeated rounds of temperature fluctuation.

Material and Methods

1: DNA Oligos Prepared
2(N6) Direct Capture, binding to D761:
D1102 (HIV wild Type):
5'-TCTACAG(N6)C(N6)TGTTAAAAGA
GACCATCAATGAGGAAGCTGCAGAATGGGATA-3'
2‾(W97) Direct Capture, binding to mutD761 (D1181):
D1250: D1102 mut: (HIV mutant)
5'-TCTACAG(W97)C(W97)TGTTAAAAGA
CACCATCAATGAGGAAGCTGCAGAATGGGATA-3'
2: Chip Preparation: The two deposition solutions were mixed, and the probes were deposited as follows: D1181 for pads 4, 6, 9; D1182 for pads 8, 10, 14 (HIV); D365 for pads 3, 5, 7; D660 for 11, 13, 12, 15, 16. on the 500 nm chips. Post-treatment of chips with M44/Acetonitrile/Heat. Mounted the chips with small cartridges.

3: Prepared Hybridization Buffer with Target and Signal Oligos

Treated human whole blood with an equal volume of AL (from Qiagen) lysis buffer and 1/8 blood vol. of Proteinase K (20 mg/ml) and incubated at 70° C. for 10 minutes. Hybridize 0.25 uM D1102 or D1250 with surface probe oligos in blood lysate with NaClO4 at room temperature for 20 minutes. Measured electrochemical signal.

Results and Discussion:

We introduced the differentially labeled oligos alone, or in combination, and analyzed their distribution with respect to electrodes containing perfectly matched capture probes and electrodes containing mismatched capture probes.

When the oligos were introduced alone, they bound and signaled at electrodes where they were perfectly matched and electrodes where they were mismatched. In contrast, when the oligos were introduced in combination, the oligos segregated to their perfectly matched capture probes without temperature manipulation.

These results show that the oligos compete for hybridization to the capture probes when simultaneously introduced. Without being bound by theory, we speculate that the off-rates are significantly higher on saturated electrodes.

We examined the potential competition between targets in the context of their sequential addition to the array; the results are shown in FIG. 26. 0.25M of D1102 was first hybridized to an array of wild type and mutant surface probes. After 20 minutes of hybridization, a mixture of D1250 and D1102 at 0.25 uM was injected into the cartridge after the first volume had been removed. After the addition of the solution containing heterogeneous targets, the electrochemical signal was recorded at various time points. Within 10 minutes after the change, the electrochemical signal at 160 mV (the label on the wild-type oligo) has dropped, while a signal at 375 mV (the label on the mutant oligo) has emerged. The data are consistent with the replacement of mismatched oligos on capture probes with perfectly matched targets. After 2 hours, ¾ of the signal output on the electrodes containing mutant capture probes is derived from mutant oligos. In the same array, the signal output from the electrodes containing wild-type capture probes is largely unchanged and correlates with the exclusive presence of wild-type oligo throughout the two hour period. Our findings suggest that oligos compete, at least at high concentrations, for binding to electrode immobilized, capture probes. The results suggest that addressing oligos to specific electrodes through hybridization-based discrimination of single nucleotide differences may be achieved on the sensor array.

Example 5

Model Study for the Detection of Oligonucleotide Ligation Assay (OLA) Products Purpose: To develop methodologies for the discrimination of substrates and products of the OLA reaction on the sensor.

Introduction: Two N6 labeled DNA oligos systems were designed to mimic the substrate and product of an OLA reaction. D1102, a 50-mer oligo that corresponds to a portion of the HIV genome was used to represent an OLA product. Two additional oligos were made to represent substrates of the 50-mer product. D1274 (D1102_short.a) corresponds to the N6-labeled half of the substrate, while D1275 (D1102_short.b) corresponds to the unlabeled half. D1102 (product) hybridizes along the entire length of D1182 (wild-type surface probe of HIV), while D1274 and D1275 (substrates) hybridize with half of the capture probe each. Based upon our mismatch discrimination, we predicted that we could identify a temperature at which the full-length product would remain hybridized and generate signal but the substrate halves would dissociate and not signal.

Material and Methods
1: DNA Oligos Prepared
2(N6) Direct Capture, binding to D761 and D1182:
D1102 (HIV wild Type):
5'-TCTACAG(N6)C(N6)TGTTAAAAGA
GACCATCAATGAGGAAGCTGCAGAATGGGATA-3'
(D1274): D1102 short.a:
5'-TCTACAG(N6)C(N6)TGTTAAAAGAG
(D1275): D1102 short.b:
5'-ACCATCAATGAGGAAGCTGCAGAATGGGATA-3'
(D1182): WT_D761
5'-CATTGATGGTCTCTTTTAACA(P282)-3'
2: Chips Prepared as above.

Results and Discussion

D1102, a ligated whole piece, or D1274+D1275, the unligated (substrate) oligos were hybridized with lysed blood and Sodium Perchlorate for 20 minutes in room temperature above electrode arrays containing HIV capture probes. Electrochemical signals were measured as a function of temperature in two chips, three D1182 pads for every chip at 25, 15, or 10 and 40° C. The average of the measurements is presented in FIG. 27. Note: the value reported for the substrates at 40° C. is predicted and was not measured. However, after heating to 25° C. a second time, the value for the substrates was "0".

Example 6

Genotyping of a Variety of Samples

Genotyping of Multiple Systems in the Same Reaction:

Experiments were done to do multiple genotyping assays in one system: PIC1, Hfe-H63D, and Hfe-C282Y. Hybridization was preformed on DC237 SNP optimization arrays according to the FIG. 33A.

In attempting to genotype Hfe-C282Y, two different signal probe/target mimic combinations were used (long and short). The original system was comprised of a 19 base pair signal probe ("short") and 76 base pair target mimics for both WT and mut containing one base mismatch between the two. The "long" type refers to a 28 base pair signal probe and corresponding 69 base pair target mimics (shifted 9 bases towards the 5' end) for both WT and mut containing one base mismatch between the two. Due to the varying capture probe melting temperatures between the different systems, the chips were heated to two different temperatures to achieve the maximum differentiation between allele A/G (PIC1) and between WT/mut (Hfe-H63D, Hfe-C282Y). Measurement and heating occurred in the following manner:
1. All pads measured at 25° C.
2. Hfe-H63D pads (6, 8, 9, 14) measured at 48° C.
3. PIC1 (3, 4, 7, 11) and Hfe-C282Y pads (10, 12, 13, 15) measured at 56° C.

Results represent data from chips hybridized for 2 hours prior to measurement and are shown in FIGS. 33B, 33C and 33D. Four chips were hybridized with target mimic PIC1A, three chips were hybridized with PIC1G and three chips were hybridized with the heterozygote (PIC1A/PIC1G). These genotypes are clearly distinguishable from each other, and give ratio values comparable to the ratio values seen when chips are hybridized only with the PIC1 system targets. In the Hfe-H63D system, WT, heterozygous, and mut genotypes segregate to positions in which they can be characterized.

Attempting to genotype Hfe-C282Y was more difficult than in the above systems. Multiplex results for both the shorter and the longer type signaling probes and corresponding targets are displayed below. In both the longer and shorter probes, the WT genotypes segregates from the heterozygous and mut genotypes, with the exception of one chip containing large standard deviations. However, the longer signaling probe and corresponding target show no separation between the heterozygous and mut genotypes. The shorter signaling probe and corresponding target show greater separation between the heterozygous and mut, but large standard deviations prevent definitive genotyping. Genotyping Hfe-C282Y without any other target or signaling molecules present has yielded the same results as seen in the graph above.

Conclusion: Multiplexing several different SNPs onto one chip does not affect the genotyping of individual SNPs. While genotyping PIC1 and Hfe-H63D was relatively easy, Hfe-C282Y was unable to be genotyped. On the Hfe-C282Y_mut pads, the mismatch represents a G-T hybridization. This binding is almost as strong as the perfect match, and makes the mut genotype very difficult to distinguish from the heterozygote. However, the difficulty in genotyping Hfe-C282Y was not increased by multiplexing with other SNPs.

Using Two Potential System

The Two Potential SNP detection system was used to genotype HIV, HFE C282Y, HFE H63D, and PIC1 gene fragments accurately. A standard monolayer, which consists of H6, M44, and N152-tagged capturing, provides an extraordinary environment for probe competition. In addition, both the ferrocene-containing and the oligo motifs of the signaling probes (SP) play a role in the competition. The N6 and W97, used in this assay are different in signaling efficiency, frequency response, and hydrophilicity. Adjustments were made according to those differences to balance their activities. The optimized probes for the Two Potential System have the following two features: 1. One of the probes is labeled with a 4 N6 motif while the other one is labeled with a 8 W97 motif. 2. They are 17mers with a SNP identification base located in the middle of the sequences. The assay can be carried out with a simple hybridization at room temperature without applying any stringency such as temperature ramping or washing. Yet, the assay noise is near zero. The assay can also be carried out at slightly elevated temperature (35° C.) where assay kinetics is hastened and assay noise is further reduced.

I. Genotyping HIV, HFE, and PIC DNA Target Mimics were Achieved Using the Two Potential System 1. Genotyping of HIV Target Mimics For the Two Potential assay, target and SP ratio was always kept at a ratio of 1 to 5. In genotyping the HIV, a cocktail of the wild type (WT) 4-N6-labeled SP (D1864) and the mutant (mut) 8-W97-labeled SP (D1835) were hybridized to each WT D765 (50 nM), mut D999 (50 nM), and D765+D999 targets (25 nM each) in C6 buffer. After 20 minutes of hybridization at room temperature, genotyping these HIV targets correctly was achieved (FIG. 1). The $\log_2$ of the WT to mut signal ratio of homozygous WT HIV sample was 0.96, −0.65 for the homozygous mut, and 0.24 for the heterozygous HIV sample. Those ratios improved to 1.36, −2.43, and −0.06 respectively over the 2 hour time course incubation. Further studies were done with decreased target and SP concentrations. Correct genotyping for 1 nM target(s) and 5 nM of each SP occurred after the $7^{th}$ hour (470 min) of incubation (FIG. 2). The $\log_2$ of the WT to mut signal ratio of homozygous WT target was 2.11, of homozygous mut target was −1.15, and that of the heterozygous targets was 1.15. Extended incubation (up to 24 hours) allowed the probe competition to proceed for a longer time and achieved even better distinction of the genotypes.

The attempt to get higher signal level of genotyping 1 nM HIV targets through using higher concentration of SPs was not successful, but it did allow us to genotype earlier. Using 1 nM target(s) and 20 nM of each SP allowed us to genotype at the 5th hour of hybridization (FIG. 3). The $\log_2$ of the WT to mut signal ratio was 2.01 for homozygous WT, −0.87 for homozygous mut, and 0.032 for heterozygous targets. But in terms of peak height and signal ratios, 1:20 of target to SP ratio didn't seem to have any advantage over that of 1:5 ratio just described above. So we planned to keep the target to SP ratio at 1:5 for the Two Potential assays for the time being.

2. Detection of Emerging HFE C282Y Mutants

The 2-potential system allowed us to detect minor presence (10%) of mut HFE C282Y population in a large population of the WT target. A cocktail of the WT 8-W97-labeled SP D1954 and the mut 4-N6-labeled SP D1955 were hybridized to samples that contained WT (D1749) and mut HFE (D1750) at a combined total concentration of 50 nM. These samples contained mut HFE in 10% increment of concentration relative to that of the WT. So our targets range from 100% homozygous WT to 50%/50% heterozygous, and to 100% homozygous. In corresponding to the increase of emerging mut, there was an increase in mut N6 and a decrease in WT W97 signals (FIG. 4). Thus there is an increase in mut to WT signal ratio. As low as 10% mut species can be detected using the 2-potential system; and, differentiation between 0, 10, and 20% mut HFE species was possible.

This study was repeated with 5 nM of total targets and 25 nM of each SP (LC087). The ratios did not let us distinguish the varying degrees of mut population as well. Instead of having a 1:1 N6/W97 ratio when there was 50% WT and 50% mut targets, the 1:1 ratio occurred when there was about 60-70% mut target; but, the expected trend of increasing mut to WT ratio was observed. Also, there was a lot of chip to chip and pad to pad variations. While many of the N6/W97 ratios fell into the expected trend, the real signal heights between the chips varied. And when there was 100% mut target, a few pads showed increasing WT W97 signals after the $4^{th}$ hour. Silver degradation may be the cause of this increase in W97 signal. Once we get the chip variation problem resolved, we would be able to detect emerging mutants in a quantitative fashion using the Two Potential system 3. Genotyping of HFE H63D After genotyping of HIV and HFE C282Y target mimics were achieved using the 2-potential system, we proceeded to test the system with HFE H63D and PIC 1 targets (described in Section 4). A SP cocktail solution of the WT 8-W97-labeled D2004 and the mut 4-N6-labeled D2005 were added to C6 hybridization buffer containing each HFE H63D WT D1121 (50 nM), mut D1122 (50 nM), and D1121+D1122 targets (25 nM each). They were hybridized and then incubated at 35° C. First ACV run occurred at 2.5 hr of the hybridization and resulted in match/mismatch ratios of 209 for homozygous WT and 195 for homozygous mut. The N6/W97 ratio for the heterozygous targets was 2.32. Differentiating the three different samples was unmistakably achieved (FIG. 5).

4. Genotyping of PIC1

SP cocktail of the WT 8-W97-labeled D1875 and mut 4-N6-labeled D2006 were combined with each 50 nM PIC1A (D1775), 50 nM PIC1G (D1776), and heterozygous D1775+ D1776 targets (5 nM each) in hybridization buffer. First ACV was taken at 2.5 hr. Unlike HFE-H, we were unable to differentiate the three different targets. In all three situations, only the PIC1G N6 signal appeared with hardly any sign of PIC1A signals (FIG. 6). Even in the case where there were no PIC1G targets, we only see the PIC1G signal. A similar experiment in which the targets and buffer were first added to the chips, allowed to hybridize to the capture probes for 2 hours, and then SPs were added still had the same outcome (LC096).

Unsuccessful PIC1 genotyping may be due to that the SNP identification base Guanine (G) of the PIC1G SP bound to the Thymine (T) of the PIC1A target with an affinity that was as good as the PIC1A SP bound to the PIC1A target (an A, T pairing). In addition, the N6 appeared to have advantage over W97 in stablizing the SP over the monolayer, which may explain why the PIC1 genotyping failed. To balance all the factors that are influencing the outcome of probe competition, the probe (17mer) that is perfect match to PIC1G is to be labeled with N6 while the PIC1A probe (17mer) to be labeled with W97.

Before getting those new probes, we have used Bruce's PIC 1 probes (D1890 and D1876, 19mers) which have exactly the same ferrocene motifs attached as we desired. A SP cocktail of PIC1A 4-N6-labeled (D1890) and PIC1G 8-W97-labeled (D1876) was added to each homozygous PIC1A and PIC1G, and heterozygous targets. Although there was an unintended drawback that the first base of the SP 5' ends competed with the base of the capture probe's 3' end for hybridizing to the target, genotyping was achieved in 70 minutes because the $\log_2$ WT to mut ratio was 1.64 for homozygous WT, −1.11 for homozygous mut, and 0.74 for heterozygous targets (FIG. 7). This experiment will be repeated with 17mer signaling probes without the competition of the capture probe and signaling probe for the target.

II. Assay Optimization

1. Hybridization Methods

The next step after genotyping HIV and HFE target oligo mimics is to genotype A-PCR amplicons of patient samples. In order to genotype accurately, we need to test which hybridization method would work best and thus would give the best signals. Three methods were compared. For the first two methods, an APCR heterozygous HFE C282Y target control was allowed to hybridize to a cocktail of WT 8-W97-labeled SP (D1954) and mut 4-N6-labeled SP (D1955) and then heated to 100° C. for 3 minutes. One was put on ice for 10 minutes while the other was allowed to cool on the benchtop for 10 min. The samples were then mixed with C6 buffer and applied to the chips for further hybridization. For the third method, the target, SP cocktail, and buffer were combined; heated to 100° C.; and cooled on the benchtop. Based on the signals (LC091), the two methods where the components were cooled on the benchtop worked better. The third method was the most robust in which the targets, SPs, and buffer were combined before the heating step, and it will be used for the future experiments. There were silver problem experienced in this experiment. For a few pads of all three methods, N6 signals were similar to those of W97 in 60 minutes into hybridization; but, over time N6 signals remain the same (or increased a little) while those of W97 increased. Caution will be taken for this potential implication in the further experiments.

2. Hastening Hybridization Kinetics with Elevated Incubation Temperature

A-PCR product of HFE C282Y mutant was allowed to hybridize to a cocktail of WT 8-W97-labeled SP (D1954) and mut 4-N6-labeled SP (D1955). Hybridization was carried out at three different temperatures, 25° C., 30° C., and 35° C. Scanning was performed after 2 hours of incubation. As shown in FIG. 8, 35° C. incubation yield the highest signal (17 nA) followed by 30° C. (11 nA) and 25° C. (5.5 nA), an indication that higher hybridization temperature hastened the kinetics.

3. A-PCR Primer Ratios

In order to genotype accurately, we need to find the best A-PCR method from which we can derive the most single-stranded targets. Eleven solutions of antisense HFE C282Y amplicons each produced from different concentrations of nested primers were each combined with C6 hybridization buffer and a SP cocktail of WT 8-W97-labeled D2007 and mut 4-N4-labeled D2008 (each SP=250 nM). They were hybridized and scanned at 35° C. Nine were genotyped as WT HFE C (FIG. 9). One of the two that had no signals (#5) was a solution of double-stranded genomic DNA and the other (#11) was a blank control of A-PCR product. Of the nine that were genotyped as WT targets, the one which used 24 pmol of each forward and reverse primer making double-stranded DNA from genomic DNA and then amplified with 2 pmol forward and 100 reverse nested primers on purified double stranded DNA (#4), and another that used 48 pmol of each primer making double-stranded DNA from genomic DNA and then amplified with 2 pmol forward and 100 pmol reverse nested primers (#10) gave signals that were among the best. These two (#4 and #10) had very high signals (~18 nA) in 30 minutes, and reached saturation in 3 hours. Many of the other A-PCR targets (#1, 2, 7) started with very low signals (less than 5 nA) in 30 minutes and didn't reach saturation until after the 13$^{th}$ hour of hybridization. Those clearly had low concentrations of single-stranded targets to begin with and took a much longer time to saturate the pads, while #4 and #10 had high concentrations of single-stranded targets (almost as high as the 50 nM WT target mimic control #12 of 22 nA in 30 minutes) and reached saturation much earlier. A-PCR procedure #10 will be used in future experiments because it does not require a purification step before the A-PCR steps, which was used in #6.

Materials and Methods

Oligos used in these experiments are listed in the following table.

| Code | Sequence 5' to 3' |
|---|---|
| D765 | GAC ATC AAG CAG CCA TGC AAA TGT TAA AAG AGA CCA TCA ATG AGG AAG CTG CAG AAT GGG ATA GA |
| D999 | GAC ATC AAG CTG CCA TGC AAA TGT TAA AAG AGA CCA TCA ATG AGG AAG CTG CAG AAT GGG ATA GA |
| D1117 | GCT GAT CCA GGC CTG GGT GCT CCA CCT GGC ACG TAT ATC TCT GCT CTT CCC CAG GGG GTA CAG CC |
| D1118 | GCT GAT CCA GGC CTG GGT GCT CCA CCT GGT ACG TAT ATC TCT GCT CTT CCC CAG GGG GTA CAG CC |
| D1121 | AGT TCG GGG CTC CAC ACG GCG ACT CTC ATG ATC ATA GAA CAC GAA CAG CTG GTC ATC CAC GTA GCC CAA ACT TCA |
| D1122 | AGT TCG GGG CTC CAC ACG GCG ACT CTC ATC ATC ATA GAA CAC GAA CAG CTG GTC ATC CAC GTA GCC CAA ACT TCA |
| D1749 | CCC CCT GGG GAA GAG CAG AGA TAT ACG TGC CAG GTG GAG CAC CCA GGC CTG GAT CAG CCC CTC ATT GTG ATC TG |
| D1750 | CCC CCT GGG GAA GAG CAG AGA TAT ACG TAC CAG GTG GAG CAC CCA GGC CTG GAT CAG CCC CTC A |
| D1775 | TGT CTG CAG TGG CCC GGG GCC GTG GTG AAG CTG GCC AGG TCT TTC GCA GCT GGA TTC TGC GGC C |
| D1776 | TGT CTG CAG TGG CCC GGG GCC GTG GTG AAG CCG GCC AGG TCT TTC GCA GCT GGA TTC TGC GGC CGG GAT GGC GGG |
| D1835 | (W97) C(W97) G(W97) C(W97) GCT TA(W97) C(W97) G(W97) C(W97) G(C131) TGC ATG GCA GCT TGA TG |
| D1864 | (N6) C(N6) G(N6) C(N6) G(C131) TGC ATG GCT GCT TGA TG |
| D1875 | (W97) C(W97) G(W97) C(W97) GCT TA(W97) C(W97) G(W97) C(W97) G(C131) ACC TGG CCA GCT TCA CC |
| D1876 | (W97) C(W97) G(W97) C(W97) GCT TA(W97) C(W97) G(W97) C(W97) G(C131) GAC CTG GCC GGC TTC ACC A |
| D1890 | (N6) C(N6) G(N6) C(N6) G(C131) GAC CTG GCC AGC TTC ACC A |
| D1954 | (W97) C(W97) G(W97) C(W97) GCT TA(W97) C(W97) G(W97) C(W97) G(C131) CCA CCT GGC ACG TAT AT |
| D1955 | (N6) C(N6) G(N6) C(N6) G(C131) CCA CCT GGT ACG TAT AT |
| D2004 | (W97) C(W97) G(W97) C(W97) GCT TA(W97) C(W97) G(W97) C(W97) G(C131) TCT ATG ATC ATG AGA GT |
| D2005 | (N6) C(N6) G(N6) C(N6) G(C131) TCT ATG ATG ATG AGA GT |
| D2006 | (N6) C(N6) G(N6) C(N6) G(C131) ACC TGG CCG GCT TCA CC |
| D2007 | (W97) C(W97) G(W97) C(W97) GCT TA(W97) C(W97) G(W97) C(W97) G(C131) ATA TAC GTG CCA GGT GG |
| D2008 | (N6) C(N6) G(N6) C(N6) G(C131) ATA TAC GTA CCA GGT GG |

Chips: DC213, DC225, DC236, DC273

Hybridization: Cocktail solutions of the WT and mut signaling probes are added to targets and C6 hybridization buffer, and were allowed to hybridize at room temperature (unless otherwise noted). Small cartridges were used in these experiments. Results are shown in FIG. 34.

Additional experiments were done to titrate the detectable ratios.

| % mutant | Signal Ratio (WT:Mutant) at 35oC |
| --- | --- |
| 12 | 7 |
| 8.3% | 11 |
| 6.6% | 12.6 |
| 4.7% | 17.5 |
| 2.6% | 30 |
| 0* | 77 |

*mutant specific signal in absence of mutant target was 0.1 nA

Example 7

Displacement of a First SAM with a Second SAM to Increase Signalling

Without being bound by theory, it appears that electron transfer from an ETM to the electrode surface is facilitated through electroconduits. Theoretically, the more available the electrode surface, the better the signalling. Based on this hypothesis, methods were created to make the surface more available for signalling, using short hydroxy-terminated alkylthiols (C2 to C6) to replace short aromatic-terminated (such as 4,5-dimethoxy-2-nitrobenzyl groups) alkylthiols. The latter will block the leakage of potassium ferricyanide(III). An example is W150 that is synthesized and used to make a SAM, using standard techniques. This results in a monolayer that is not permeable to potassium ferricyanide(III); however, the addition of mercaptoethanol for short periods of time results in an electrochemical signal from the potassium ferricyanide(III).

Accordingly, a model system was tested. Using SAMs comprising either M44 (the standard alkyl insulator) or W150, in conjunction with either a positive capture probe, or two different negative capture probes (i.e. these probes are not complementary to the target sequence), the following results were obtained. As a preliminary matter, as compared to M44, W150 always provided higher positive signals and lower negative signals; for example, using a target sequence comprising 20 ferrocenes, at an AC frequency of 10,000 Hz, the monolayers comprising M44 gave Ip of 67.2 nA, while the W150 monolayers gave Ip of 1700 nA. The positive signals could be further boosted at high frequency (1000 Hz or greater) after the chips were soaked in 1 mM mercaptoethanol in 6×SSC buffer: before soaking, the Ip at 10,000 Hz was 1700 nA, and after soaking was 8740 nA. However, at low frequency, the soaking had no effect on signalling.

We claim:

1. A method of determining the identification of nucleotide(s) at a first detection position in a first domain of a target sequence, said target sequence comprising said first domain and a second domain, said method comprising:
   a. providing an electrode with a covalently attached capture probe, wherein said capture probe has a sequence substantially complementary to said second domain of said target sequence;
   b. contacting said electrode with:
      (i) said target sequence;
      (ii) a first label probe substantially complementary to said first domain, comprising a first nucleotide at an interrogation position and a first electron transfer moiety (ETM) with a first redox potential;
      (iii) a second label probe substantially complementary to said first domain, comprising a second nucleotide at said interrogation position and a second ETM with a second redox potential;
      under conditions wherein if said nucleotide at said interrogation position is perfectly complementary to said detection position, hybridization of said probe(s) occurs; and
   c. detecting the presence of said first and/or second ETM to determine the nucleotide(s) at said detection position.

2. The method of claim 1 wherein said method further comprises contacting said electrode with a third label probe substantially complementary to said first domain, comprising a third nucleotide at said interrogation position and a third ETM with a third redox potential.

3. The method of claim 2 wherein said method further comprises contacting said electrode with a fourth label probe substantially complementary to said first domain, comprising a fourth nucleotide at said interrogation position and a fourth ETM with a fourth redox potential.

4. The method of claim 1 wherein said electrode comprises an array of capture probes, each substantially complementary to a second domain of a different target sequence.

5. The method of claim 1 wherein said first label probe contains a plurality of first ETMs.

6. The method of claim 1 wherein said second label probe contains a plurality of second ETMs.

7. The method of claim 1 wherein said electron transfer moieties comprise a transition metal complex.

8. The method of claim 7 wherein said transition metal complex comprises a metallocene.

9. The method of claim 8 wherein said metallocene is a ferrocene.

10. The method of claim 8 wherein said metallocene is a ferrocene derivative.

* * * * *